US012391955B2

(12) United States Patent
Umemoto et al.

(10) Patent No.: US 12,391,955 B2
(45) Date of Patent: Aug. 19, 2025

(54) PLANT HAVING ENHANCED RESISTANCE AGAINST COLORADO POTATO BEETLE AND METHOD FOR PRODUCING SAME, AND METHOD FOR EVALUATING RESISTANCE AGAINST COLORADO POTATO BEETLE IN PLANT

(71) Applicants: KANEKA CORPORATION, Osaka (JP); NATIONAL UNIVERSITY CORPORATION KOBE UNIVERSITY, Hyogo (JP); NATIONAL AGRICULTURE AND FOOD RESEARCH ORGANIZATION, Ibaraki (JP); RIKEN, Saitama (JP)

(72) Inventors: Naoyuki Umemoto, Saitama (JP); Masaharu Mizutani, Hyogo (JP); Ryota Akiyama, Hyogo (JP); Kenji Asano, Hokkaido (JP); Haruyasu Hamada, Hyogo (JP); Yozo Nagira, Hyogo (JP); Akira Endo, Hyogo (JP); Kazuki Saito, Saitama (JP)

(73) Assignees: KANEKA CORPORATION, Osaka (JP); NATIONAL UNIVERSITY CORPORATION KOBE UNIVERSITY, Hyogo (JP); NATIONAL AGRICULTURE AND FOOD RESEARCH ORGANIZATION, Ibaraki (JP); RIKEN, Saitama (JP)

( * ) Notice: Subject to any disclaimer, the term of this patent is extended or adjusted under 35 U.S.C. 154(b) by 0 days.

(21) Appl. No.: 17/905,518

(22) PCT Filed: Mar. 3, 2020

(86) PCT No.: PCT/JP2020/008910

§ 371 (c)(1),
(2) Date: Sep. 2, 2022

(87) PCT Pub. No.: WO2021/176557

PCT Pub. Date: Sep. 10, 2021

(65) Prior Publication Data

US 2024/0209389 A1 Jun. 27, 2024

(51) Int. Cl.

*C12N 15/82* (2006.01)
*A01H 1/00* (2006.01)
*A01H 6/82* (2018.01)
*C12N 15/11* (2006.01)

(52) U.S. Cl.

CPC ......... *C12N 15/8286* (2013.01); *A01H 1/127* (2021.01); *A01H 6/827* (2018.05); *C12N 15/11* (2013.01)

(58) Field of Classification Search

None
See application file for complete search history.

(56) References Cited

U.S. PATENT DOCUMENTS

2019/0367940 A1* 12/2019 Aharoni ............ C12N 15/8279

FOREIGN PATENT DOCUMENTS

JP 2020-036591 3/2020
WO 2018/146678 8/2018

OTHER PUBLICATIONS

Jansky et al 1999 (HortScience 34:5, p. 922-927) (Year: 1999).*
McClean 1998 (https://www.ndsu.edu/pubweb/~mcclean/plsc731/dna/dna6.htm) (Year: 1998).*
Maharijaya and Vosman, “Managing the Colorado potato beetle; the need for resistance breeding”, Euphytica (2015) 204: 487-501.
Liu et al. “Invasion of Colorado potato beetle, Leptinotarsa decemlineata, in China: dispersal, occurrence, and economic impact”, Entomologia Experimentalis et Applicata 143: 207-217, 2012.
Stürckow and Löw, “Die Wirkung Einiger Solanum-Alkaoidglykoside Auf Den Kartoffelkäfer, Leptinotarsa Decemlineata Say’)”, Entomologia Experimentalis et Applicata 4 (1961):133-142.
Sinden et al., “Leptine Glycoalkaloids and Resistance to the Colorad Potato Beetle (Coleoptera: Chrysomelidae) in Solanum chacoense”, Environmental Entomology vol. 15, No. 5 (1986):1057-1062.
Ronning et al., “Identification of molecular markers associated with leptine production in a population of Solanum chacoense Bitter”, Theor Appl Genet. (1999) 98:39-46.
Sagredo et al., “Mapping of genes associated with leptine content of tetraploid potato”, Theor Appl Genet. (2006) 114:131-42.
Pablo D. Cardenas et al., “Pathways to defense metabolites and evading fruit bitterness in genus Solanum evolved through 2-oxoglutarate-dependent dioxygenases”, Nature Communications, Nov. 14, 2019, vol. 10, No. 5169, pp. 1-13.
James H. Lorenzen et al., “Resistant Potato Selections Contain Leptine and Inhibit Development of the Colorado Potato Beetle (Coleoptera: Chrysomelidae)”, Journal of Economic Entomology, vol. 94, Issue 5, Oct. 1, 2001, pp. 1260-1267.

* cited by examiner

*Primary Examiner* — Matthew R Keogh
(74) *Attorney, Agent, or Firm* — IPUSA, PLLC

(57) ABSTRACT

The spirosolane skeleton 23-position hydroxylase gene and the spirosolane skeleton 23-position acetyltransferase gene derived from *S. chacoense, S. tuberosum*, and *S. lycopersicum* are found to be involved with the biosynthesis of leptine, which achieves resistance against Colorado potato beetle.

6 Claims, 19 Drawing Sheets

Specification includes a Sequence Listing.

FIG.17D

```
Sc PromoterA : SEQ ID NO. 44           1405 TGATATATAGACCACATATTTCCTCATTTTTAAAGTAAAAATCTTGAT------------ 1452
Sc PromoterB : SEQ ID NO. 45           1406 TGATATATAGACCACATATTTCCTCATTTTTAAAGTAAAAATCTTGAT------------ 1453
M6 TPromoter : SEQ ID NO. 41           1159 --ATATATAGACCACATATTTCCTCATTTTTAAAGTAAAAATCTTGAT------------ 1204
Sassy PromoterA : SEQ ID NO. 47         358 ------------------------------------------------GTTAGGGTTTTG 369
Konafubuki PromoterA : SEQ ID NO. 49    358 ------------------------------------------------GTTAGGGTTTTG 369
Sassy PromoterB : SEQ ID NO. 48         358 ------------------------------------------------GTTAGGGTTTTG 369

Sc PromoterA : SEQ ID NO. 44           1452 ------------------------------------------------------------ 1452
Sc PromoterB : SEQ ID NO. 45           1453 ------------------------------------------------------------ 1453
M6 TPromoter : SEQ ID NO. 41           1204 ------------------------------------------------------------ 1204
Sassy PromoterA : SEQ ID NO. 47         370 CCCTGGTTTTCTTACCATAATTTGAGATTTATTTTTTCTTAAAGAAAAGACAAAACACTA 429
Konafubuki PromoterA : SEQ ID NO. 49    370 CCCTGGTTTTCTTACCATAATTTGAGATTTATTTTTTCTTAAAGAAAAGACAAAACACTA 429
Sassy PromoterB : SEQ ID NO. 48         370 CCCTGGTTTTCTTACCATAATTTAAGATTTATTTTTTCTTAAAGAAAAGACAAAACACTA 429

Sc PromoterA : SEQ ID NO. 44           1452 ------------------------------------------------------------ 1452
Sc PromoterB : SEQ ID NO. 45           1453 ------------------------------------------------------------ 1453
M6 TPromoter : SEQ ID NO. 41           1204 ------------------------------------------------------------ 1204
Sassy PromoterA : SEQ ID NO. 47         430 CCATAAATGTTTTTACTTTTTCTGAAAGAAAAATATAATATTCTTTCATATTTGGTTTAT 489
Konafubuki PromoterA : SEQ ID NO. 49    430 CCATAAATGTTTTTACTTTTTCTGAAAGAAAAATATAATATTCTTTCATATTTGGTTTAT 489
Sassy PromoterB : SEQ ID NO. 48         430 CCATAAATGTTTTTACTTTTTCTGAAAGAAAAATATAATATTCTTTCATATTTGGTTTAT 489

Sc PromoterA : SEQ ID NO. 44           1452 ------------------------------------------------------------ 1452
Sc PromoterB : SEQ ID NO. 45           1453 ------------------------------------------------------------ 1453
M6 TPromoter : SEQ ID NO. 41           1204 ------------------------------------------------------------ 1204
Sassy PromoterA : SEQ ID NO. 47         490 TCTTTCCTTTTAGGAAAATGTTTATGGAGTAGCTAGTTCTTTTCTAGTAGGAAAGGTTTT 549
Konafubuki PromoterA : SEQ ID NO. 49    490 TCTTTCCTTTTAGGAAAATGTTTATGGAGTAGCTAGTTCTTTTCTAGTAGGAAAGGTTTT 549
Sassy PromoterB : SEQ ID NO. 48         490 TCTTTCCTTTTAGGAAAATGTTTATGGAGTAGCTAGTTCTTTTCTAGTAGGAAAGGTTTT 549

Sc PromoterA : SEQ ID NO. 44           1452 ------------------------------------------------------------ 1452
Sc PromoterB : SEQ ID NO. 45           1453 ------------------------------------------------------------ 1453
M6 TPromoter : SEQ ID NO. 41           1204 ------------------------------------------------------------ 1204
Sassy PromoterA : SEQ ID NO. 47         550 AGGACTCTATAAATATAGGTTTGTTTCTTCTAACACAATAATAACAATAACATCCACAAT 609
Konafubuki PromoterA : SEQ ID NO. 49    550 AGGACTCTATAAATATAGGTTTGTTTCTTCTAACACAATAATAACAATAACATCCACAAT 609
Sassy PromoterB : SEQ ID NO. 48         550 AGGACTCTATAAATATAGGTTTGTTTCTTCTAACACAATAATAACAATAACATCCACAAT 609

Sc PromoterA : SEQ ID NO. 44           1452 ------------------------------------------------------------ 1452
Sc PromoterB : SEQ ID NO. 45           1453 ------------------------------------------------------------ 1453
M6 TPromoter : SEQ ID NO. 41           1204 ------------------------------------------------------------ 1204
Sassy PromoterA : SEQ ID NO. 47         610 GTAGTTTTTTAAGAATTTAGTTTATGAGGAGATTTTCTCCTAAACATATTTATGCTTTTT 669
Konafubuki PromoterA : SEQ ID NO. 49    610 GTAGTTTTTTAAGAATTTAGTTTATGAGGAGATTTTCTCCTAAACATATTTATGCTTTTT 669
Sassy PromoterB : SEQ ID NO. 48         610 GTAGTTTTTTAAGAATTTAGTTTATGGGGAGATTTTCTCCTAAACATATTTATGCTTTTT 669

Sc PromoterA : SEQ ID NO. 44           1452 ------------------------------------------------------------ 1452
Sc PromoterB : SEQ ID NO. 45           1453 ------------------------------------------------------------ 1453
M6 TPromoter : SEQ ID NO. 41           1204 ------------------------------------------------------------ 1204
Sassy PromoterA : SEQ ID NO. 47         670 AATAGTAGTTTTCAATATGTAGGTCGTTTGACCAAACCATATTAATAATATATCTTTAGT 729
Konafubuki PromoterA : SEQ ID NO. 49    670 AATAGTAGTTTTCAATATGTAGGTCGTTTGACCAAACCATATTAATAATATATCTTTAGT 729
Sassy PromoterB : SEQ ID NO. 48         670 AATAGTAGTTTTCAATATGTAGGTCGTTTGACCAAACCATATTAATAATATATCTTTAGT 729

Sc PromoterA : SEQ ID NO. 44           1452 ------------------------------------------------------------ 1452
Sc PromoterB : SEQ ID NO. 45           1453 ------------------------------------------------------------ 1453
M6 TPromoter : SEQ ID NO. 41           1204 ------------------------------------------------------------ 1204
Sassy PromoterA : SEQ ID NO. 47         730 ATGTTTTTATTTATCGTCTGTTTTGTCAACCATATGATTTGCAATTGTACGCTTCCGCAT 789
Konafubuki PromoterA : SEQ ID NO. 49    730 ATGTTTTTATTTATCGTCTGTTTTGTCAACCATATGATTTGCAATTGTACGCTTCCGCAT 789
Sassy PromoterB : SEQ ID NO. 48         730 GTGTTTTTATTTATCGTCTGATTTGTCAACCATATGATTTGCAATTGTACGCTTCCGCAT 789
```

PLANT HAVING ENHANCED RESISTANCE AGAINST COLORADO POTATO BEETLE AND METHOD FOR PRODUCING SAME, AND METHOD FOR EVALUATING RESISTANCE AGAINST COLORADO POTATO BEETLE IN PLANT

INCORPORATION BY REFERENCE

The 57,264-byte text file titled "22KC-001SequenceListing4.txt" (Creation Date: Sep. 20, 2024 is hereby incorporated by reference.

TECHNICAL FIELD

The present invention relates to a plant having increased resistance against Colorado potato beetle and to a plant cell that is capable of regenerating the plant. Also, the present invention relates to a method for producing the plant and to a composition used for increasing resistance of a plant against Colorado potato beetle. Further, the present invention relates to a method for determining resistance against Colorado potato beetle in a plant. Also, the present invention relates to a composition used for introducing a hydroxy group or an acetoxy group to position 23 of a spirosolane skeleton, or to a composition used for increasing an amount of leptinines or leptines accumulated in a plant.

BACKGROUND ART

The Colorado potato beetle (scientific name; *Leptinotarsa decemlineata*, common name: Colorado potato beetle) is an insect of the Family Chrysomelidae of the Suborder *Polyphaga* (*Polyphaga*) of the Order Coleoptera. The Colorado potato beetle is a pest that parasitizes plants of the Family Solanaceae and eats their leaves. It is also reported that Colorado potato beetle causes the most serious insect damage especially in potatoes (e.g., *Solanum tuberosum*) and that without any agricultural chemical that is an insecticide, the loss of 40 to 80% of the amount of production can occur (NPL 1). Colorado potato beetle (CPB) has not come to Japan, but is spreading its habitat to various areas in the world, including from North America to Europe, and Asia (NPL 1). In recent years, CPB inhabits also in China, and in 2010, it is distributed in an area of 270,000 $km^2$. In an area having a large habitat, CPB is spreading at 45 km/year (NPL 2). Therefore, breeding CPB-resistant potatoes and other products is an urgent need also in Japan and also a globally important issue.

In this regard, as a potato having resistance against CPB, *Solanum chacoense* (wild species) is known. Also, it is revealed that CPB-resistant potatoes derived from *S. chacoense* can exhibit this resistance by accumulating leptines (NPLs 3 and 4). Further, it is expected that these leptines are biosynthesized, via a 2-step reaction, from solanine and chaconine accumulated in usual cultivated species, potatoes (e.g., *S. tuberosum*) (NPL 5). It is suggested that genes responsible for the biosynthesis of these leptines are located in Chromosomes 2 and 8 derived from *S. chacoense* (NPL 6).

However, this *S. chacoense* is a wild species that has not been domesticated. The yield and cultivation performance thereof are much lower than those of usual edible potatoes. This is why *S. chacoense* is not suitable for agricultural production, which is problematic. Therefore, an attempt has been made to interbreed a line derived from *S. chacoense* with usual potatoes (e.g., *S. tuberosum*) to obtain a progeny line having CPB resistance. In order to breed a potato as an excellent commercial variety, it is necessary to remove a *S. chacoense*-derived genome region that is unnecessary for CPB resistance. Removal of that region is usually performed by back-crossing with, for example, *S. tuberosum*. As described above, however, genes responsible for leptine biosynthesis have not been identified, and also the loci information of the genes has been only roughly revealed; i.e., Chromosomes 2 and 8. Therefore, selection of individuals cannot be performed using as an indicator, for example, the presence of those genes, and a commercial variety having CPB resistance has not been obtained yet.

Meanwhile, as a method for imparting CPB resistance against plants such as potatoes or the like, conceivable is a method of introducing genes responsible for leptine biosynthesis into, for example, potatoes through gene recombination, genome editing, or other techniques. As described above, however, the above genes have not been identified, and CPB-resistant plants have not been produced yet also by such a method.

This time, we have identified, from tomatoes, S123DOX gene encoding an enzyme that hydroxylates position 23 of a spirosolane compound. Based on this information, we have identified Sc23DOX from *Solanum chacoense* that accumulates leptines. Further, surprisingly, we have identified and discovered St23DOX that is not usually expressed, also in *Solanum tuberosum*. We have revealed that by introducing them into potatoes in the form that they can be expressed, leptinines, precursors of leptines which are CPB-resistant factors, can be produced.

In recent years, the same gene as the S123DOX gene was reported as GAME31 (PTL1 and NPL 7). According to these reports, GAME31 is identified from tomatoes, eggplants, and *Solanum chacoense*, but as described in PTL 1, the presence of GAME31 in *Solanum tuberosum* was not able to be found.

Regarding enzymatic activities, the reports demonstrate that the enzyme hydroxylates position 23 of a spirosolane compound (PTL 1 and NPL 7) but cannot hydroxylate solanidane (NPL 7). That is, although GAME31 of potatoes was expected to hydroxylate chaconine and solanine, precursors of leptinines I and II (PTL 1), GAME32 different from GAME31 was reported to be necessary for the hydroxylation (NPL 7, FIG. 7*b*) and the above expectation was denied. In view thereof, the authors of PTL 1 and NPL 7 do not suggest that leptinines, precursors of leptines can be produced by introducing 23DOX/GAME31 into potatoes.

This time, the present inventors have identified gene 23ACT encoding an enzyme that acetylates a 23-hydroxylated spirosolane compound. These gene and enzyme reaction are new that have never been reported in related art documents, including PTL 1 and NPL 7.

CITATION LIST

Patent Literature

PTL 1: International Publication No. WO2018146678A1 IL2018050142W GLYCOALKALOID METABOLISM ENZYMES (GAMES) AND USES THEREOF Non-Patent Literature NPL 1: Maharijaya and Vosman (2015) Euphytica 4:133-142

NPL 2: Liu et al. (2012) Entomologia Experimentalis et Applicata 143:207-217

NPL 3: Sturckow and Low (1961) Entomologia Experimentalis et Applicata 4:133-142

NPL 4: Sinden et al. (1986) Environmental Entomology 15:1057-1062

NPL 5: Ronning et al. (1999) Theor Appl Genet. 98:39-46

NPL 6: Sagredo et al. (2006) Theor Appl Genet. 114:131-42

NPL 7: Cardenas et al. (2019) NATURE COMMUNICATIONS 10:5169

SUMMARY OF INVENTION

Technical Problem

The present invention has been made in view of the above problems in the art. An object of the present invention is to identify a gene responsible for imparting CPB resistance to a plant; i.e., a gene responsible for biosynthesis of leptines. Another object of the present invention is to provide a method for efficiently producing a plant having increased resistance against CPB by using a gene identified. Still another object of the present invention is to provide a method for efficiently determining resistance against CPB in a plant by using an indicator, for example, the presence of the gene.

Solution to Problem

As described above, in *S. chacoense* that is a CPB-resistant potato, leptines that impart the resistance are assumed to be biosynthesized from solanine and chaconine (compounds having a solanidane skeleton). Regarding this biosynthesis, the present inventors focused on the metabolic process of α-tomatine (a compound having a spirosolane skeleton) in a tomato (*S. lycopersicum*), which is a plant of the same Family Solanaceae (see the upper part of FIG. 1). We assumed that in *S. chacoense*, position-23 hydroxylase (hereinafter referred to also as "23DOX") and position-23 acetyltransferase (hereinafter referred to also as "23ACT") similar to those in the metabolic process of α-tomatine in the tomato would be involved with biosynthesis of leptines through production of leptinines using α-solanine and α-chaconine as substrates (see the lower part of FIG. 1).

Then, the present inventors first tried to identify genes encoding these enzymes for the respective *S. lycopersicum* and *S. chacoense*. Although it has been revealed that the 23DOX and the 23ACT were involved with the metabolic process of α-tomatine, these sequences have not been revealed. Therefore, we first selected, from the expression database of the tomato, gene sequences that would be assumed to be involved with the metabolic process, and determined the full-length ORF sequences thereof. Then, based on the sequence of *S. lycopersicum* obtained, we screened for homologous genes in *S. chacoense* and also determined the full-length ORF sequences thereof through RACE method.

Then, enzymes encoded by the respective genes of *S. lycopersicum* and *S. chacoense* that we were able to obtain in such a manner were synthesized in *Escherichia coli*, and were analyzed for their enzymatic activity in vitro. As a result, it is revealed that 23DOX of *S. lycopersicum* and 23DOX of *S. chacoense* (which may also be referred to as "S123DOX" and "Sc23DOX", respectively) were able to each introduce a hydroxy group to position 23 of α-tomatine, and 23ACT of *S. lycopersicum* and 23ACT of *S. chacoense* (which may also be referred to as "S123ACT" and "Sc23ACT", respectively) were able to acetylate the hydroxy group.

Contrary to previous expectations, however, when α-solanine and other compounds were used also as a substrate, a hydroxy group was not introduced by the 23DOX to position 23 of the above compound, nor was the hydroxy group acetylated by the 23ACT, failing to produce leptines.

Meanwhile, production of leptinines was detected in a potato (*S. tuberosum*) to which the 23DOX gene had been introduced, and production of leptines was confirmed in the potato to which the 23DOX gene and the 23ACT gene had been introduced.

In view of the above, it is revealed that in *S. chacoense*, leptines are not biosynthesized from compounds having a solanidane skeleton (α-solanine and α-chaconine) differing from the previous expectations, but leptines are biosynthesized through the process including introducing a hydroxy group to position 23 of compounds having a spirosolane skeleton, followed by introduction of an acetoxy group, and further converting the spirosolane skeletons of these compounds to a solanidane skeleton.

Also, we produced primer sets that recognized the Sc23DOX gene and the Sc23ACT gene. We further produced crosses between *S. chacoense* and diploid potatoes that do not produce leptines. These crosses were analyzed through PCR using the primer sets and were analyzed for the amount of leptines generated. As a result, it was confirmed that the presence of the DNA markers (the 23DOX gene and the 23ACT gene of *S. chacoense*) was in agreement to the accumulation of leptines in terms of genetic behaviors.

When we further analyzed the presence or absence of the 23DOX gene and the 23ACT gene in *S. tuberosum* having no CPB resistance, surprisingly, it was revealed that the *S. tuberosum* had genes encoding proteins having high sequence identities to the 23DOX and the 23ACT (St23DOX and St23ACT).

Also, proteins encoded by these genes were synthesized in *Escherichia coli* and were analyzed for their enzymatic activities in vitro. As a result, it was revealed that, similarly with the above-described S123DOX and Sc23DOX, the St23DOX was able to introduce a hydroxy group to position 23 of α-tomatine. Further, it was also revealed that similar to the above-described S123ACT and Sc23ACT, the St23ACT was able to acetylate the hydroxy group.

On the basis of the above findings, the present invention has been completed. That is, the present invention provides the followings in detail.

<1> A composition that is used for introducing a hydroxy group to position 23 of a spirosolane skeleton, the composition including:

at least one DNA selected from the group consisting of (a) to (d) below:

(a) DNA encoding a protein that consists of an amino acid sequence as set forth in SEQ ID NO: 2, 4, or 6;

(b) DNA encoding a protein that consists of an amino acid sequence having 80% or higher identity to an amino acid sequence as set forth in SEQ ID NO: 2, 4, or 6, and has an activity to hydroxylate position 23 of a spirosolane skeleton;

(c) DNA encoding a protein that consists of an amino acid sequence identical to the amino acid sequence as set forth in SEQ ID NO: 2, 4, or 6 except that one or two or more amino acids are substituted, deleted, added, and/or inserted, and has the activity to hydroxylate the position 23 of the spirosolane skeleton; and (d) DNA that hybridizes under stringent conditions with DNA consisting of a complementary sequence to a nucleotide sequence as set forth in SEQ ID NO: 1, 3, or 5, and encodes a protein having an activity to hydroxylate position 23 of a spirosolane skeleton.

<2> A composition that is used for introducing an acetoxy group to position 23 of a spirosolane skeleton, the composition including:

at least one DNA selected from the group consisting of the (a) to (d) above and at least one DNA selected from the group consisting of (e) to (h) below:

(e) DNA encoding a protein that consists of an amino acid sequence as set forth in SEQ ID NO: 8, 10, or 12;

(f) DNA encoding a protein that consists of an amino acid sequence having 80% or higher identity to an amino acid sequence as set forth in SEQ ID NO: 8, 10, or 12, and has an activity to acetylate a hydroxy group of position 23 of a spirosolane skeleton;

(g) DNA encoding a protein that consists of an amino acid sequence identical to the amino acid sequence as set forth in SEQ ID NO: 8, 10, or 12 except that one or two or more amino acids are substituted, deleted, added, and/or inserted, and has an activity to acetylate a hydroxy group of the position 23 of the spirosolane skeleton; and (h) DNA that hybridizes under stringent conditions with DNA consisting of a complementary sequence to a nucleotide sequence as set forth in SEQ ID NO: 7, 9, or 11, and encodes a protein having an activity to acetylate a hydroxy group of position 23 of a spirosolane skeleton.

<3> A composition that is used for increasing an accumulation amount of leptinine in a plant, the composition including:

at least one DNA selected from the group consisting of the (a) to (d) above.

<4> A composition that is used for increasing an accumulation amount of leptine in a plant, the composition including:

at least one DNA selected from the group consisting of the (a) to (h) above.

<5> A composition that is used for increasing resistance of a plant against Colorado potato beetle, the composition including:

at least one DNA selected from the group consisting of the (a) to (h) above.

<6> A transformed plant cell that is capable of regenerating a plant body having increased resistance against Colorado potato beetle, the transformed plant cell including:

at least one DNA selected from the group consisting of the (a) to (h) above, the at least one DNA being introduced to the transformed plant cell.

<7> A transformed plant having increased resistance against Colorado potato beetle, wherein the transformed plant is regenerated from the transformed plant cell according to <6>.

<8> A method for producing a plant having increased resistance against Colorado potato beetle, the method including:

introducing at least one DNA selected from the group consisting of the (a) to (h) above, to a plant cell; and regenerating a plant from a transformed plant cell to which the DNA is introduced in the introducing.

<9> A method for determining resistance against Colorado potato beetle in a plant, the method including:

detecting, in a plant to be tested, presence or expression of at least one DNA selected from the group consisting of the (a) to (d) above and at least one DNA selected from the group consisting of the (e) to (h) above; and when the presence or expression of the DNAs is detected in the detecting, determining that the plant to be tested has resistance against Colorado potato beetle.

<10> A method for producing a plant having resistance against Colorado potato beetle, the method including:

crossing a plant having resistance against Colorado potato beetle, with an arbitrary plant;

determining the resistance against Colorado potato beetle in a plant obtained in the crossing, by the method according to <9>, and selecting a plant that is determined to have the resistance against Colorado potato beetle.

<11> A method for producing a plant having resistance against Colorado potato beetle, the method including:

crossing a plant having at least one DNA selected from the group consisting of the (a) to (d) above, with a plant having at least one DNA selected from the group consisting of the (e) to (h) above;

determining the resistance against Colorado potato beetle in a plant obtained in the crossing, by the method according to <9>, and selecting a plant that is determined to have the resistance against Colorado potato beetle.

The nucleotide sequence of the 23DOX gene derived from *S. chacoense* and the amino acid sequence of the protein encoded by the aforementioned sequence are shown in SEQ ID NO: 1 and SEQ ID NO: 2, respectively. The nucleotide sequence of the 23DOX gene derived from *S. tuberosum* and the amino acid sequence of the protein encoded by the aforementioned sequence are shown in SEQ ID NO: 3 and SEQ ID NO: 4, respectively. The nucleotide sequence of the 23DOX gene derived from *S. lycopersicum* and the amino acid sequence of the protein encoded by the aforementioned sequence are shown in SEQ ID NO: 5 and SEQ ID NO: 6, respectively.

The nucleotide sequence of the 23ACT gene derived from *S. chacoense* and the amino acid sequence of the protein encoded by the aforementioned sequence are shown in SEQ ID NO: 7 and SEQ ID NO: 8, respectively. The nucleotide sequence of the 23ACT gene derived from *S. tuberosum* and the amino acid sequence of the protein encoded by the aforementioned sequence are shown in SEQ ID NO: 9 and SEQ ID NO: 10, respectively. The nucleotide sequence of the 23ACT gene derived from *S. lycopersicum* and the amino acid sequence of the protein encoded by the aforementioned sequence are shown in SEQ ID NO: 11 and SEQ ID NO: 12, respectively.

Advantageous Effects of Invention

Use of the hydroxylase gene and/or acetyltransferase gene identified in the present invention can introduce a hydroxy group or an acetoxy group to position 23 of a spirosolane skeleton, and can also produce leptinine or leptine. According to the present invention, enhancement of biosynthesis of leptine and accumulation of leptine can increase, for example, resistance against CPB in a plant. That is, a plant having increased resistance against CPB can be efficiently provided. According to the present invention, for example, resistance against CPB in a plant can also be efficiently determined by using expression or presence of the gene as an indicator.

BRIEF DESCRIPTION OF DRAWINGS

FIG. 17D shows comparison of the sequences of about 1 to 1.5 kb promoter regions of the 23DOX genes of *S. chacoense* PI 458310, *S. chacoense* M6, Konafubuki, and Sassy, with each of the sequences stretched just before the start codon being described (part 4)

DESCRIPTION OF EMBODIMENTS

Regarding Composition of the Present Invention

Figure 1:
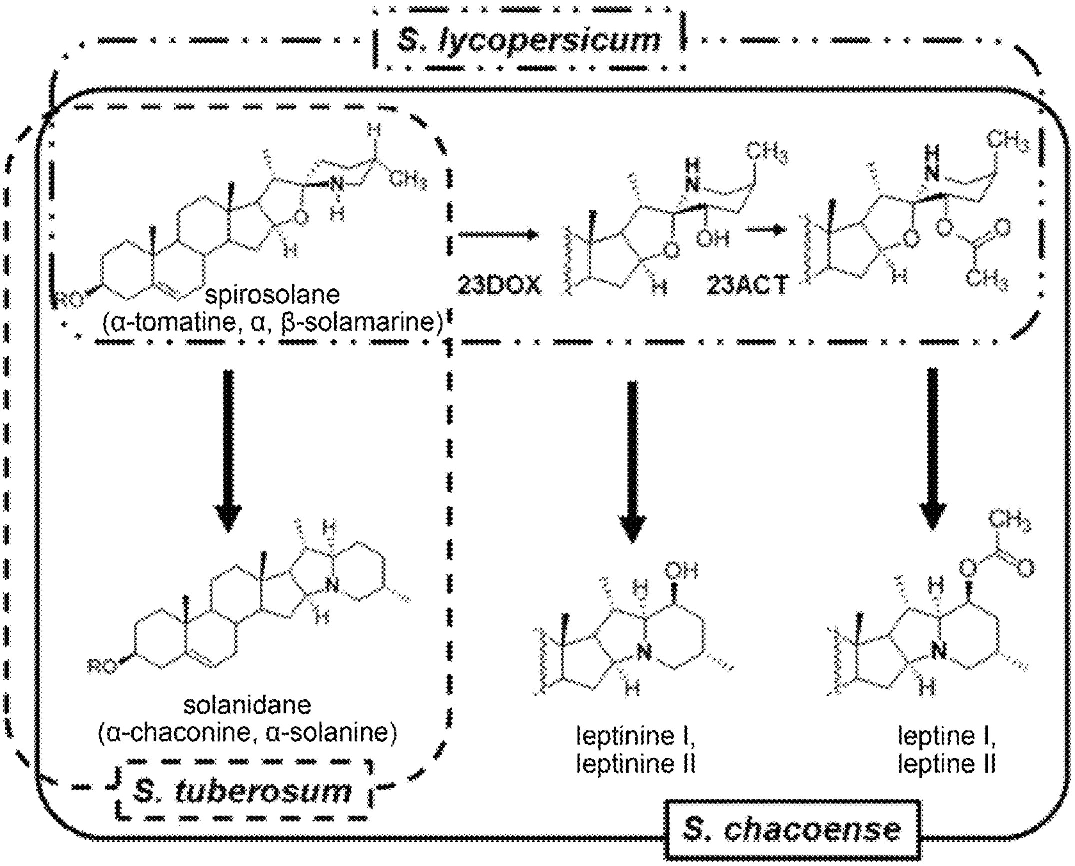
FIG. 1 is a schematic view showing glycoalkaloids in tomato (*S. lycopersicum*), CPB-resistant potato (*S. chacoense*), and CPB-nonresistant potato (*S. tuberosum*). In the enclosing line in the figure, steroid glycoalkaloid produced in each solanaceous plant is shown, and "R" at position 3 of a spirosolane skeleton and position 3 of a solanidane skeleton in the left side of the figure means saccharide complexes that bind to these skeletons via an oxygen atom. The upper part in the figure (in the enclosing line of *S. lycopersicum*) shows that, in the metabolic process of α-tomatine (a compound having a spirosolane skeleton) in tomato, a hydroxy group is introduced to 23 position of the skeleton by 23-position hydroxylase (23DOX), and an acetyl group is further introduced to the hydroxy group by 23-position acetyltransferase (23ACT)

As described in the Examples below, the present inventors isolated 23-position hydroxylase (23DOX) genes (S123DOX gene and Sc23DOX gene) in tomato (*S. lycopersicum*) and CPB-resistant potato *S. chacoense*, and identified these sequences. As a result of introducing the 23DOX gene to potato (*S. tuberosum*) that was not found to biosynthesize leptinine, it was recognized that the potato significantly biosynthesized leptinine by introducing a hydroxy group to position 23 of steroid glycoalkaloid having a spirosolane skeleton and further converting the spirosolane skeleton into a solanidane skeleton.

Moreover, the present inventors revealed that *S. tuberosum* has the 23DOX gene, but the potato was not found to biosynthesize leptinines because of its insufficient expression level.

Therefore, the present invention provides: a composition, which includes DNA encoding a protein (hereinafter is also referred to as "23DOX of the present invention") having an activity to hydroxylate position 23 of a spirosolane skeleton and is used for introducing a hydroxy group to position 23 of the spirosolane skeleton; and a composition used for improving an accumulation amount of leptinine in a plant.

As described in Examples below, the present inventors isolated 23-position acetyltransferase (23ACT) genes (S123ACT gene and Sc23ACT gene) in *S. lycopersicum* and *S. chacoense*, and identified these sequences. As a result of introducing the 23DOX gene and the 23ACT gene to potato (*S. tuberosum*) that is not recognized to biosynthesize leptine and has no resistance against CPB, it was recognized that the potato significantly biosynthesized leptines associated with resistance against CPB by further acetylating the hydroxy group introduced by 23DOX in the steroid glycoalkaloid having a spirosolane skeleton and then converting the spirosolane skeleton into a solanidane skeleton.

The present inventors revealed that among *S. tuberosum* varieties the varieties such as 97H32-6, Konafubuki, and the like, which are created using *S. chacoense* in the breeding process but produce no leptine, have the Sc23ACT gene.

Moreover, the present inventors revealed that *S. tuberosum* also has the 23ACT gene, but the potato was not found to biosynthesize leptines because of its insufficient expression level.

Therefore, the present invention also provides: a composition, which includes DNA encoding 23DOX of the present invention and DNA encoding a protein (hereinafter, is also referred to as "23ACT of the present invention") having an activity to acetylate the hydroxy group of position 23 of the spirosolane skeleton, and is used for introducing an acetoxy group to position 23 of the spirosolane skeleton; a composition used for improving an accumulation amount of leptine in a plant; and a composition used for improving resistance of a plant against CPB.

In the present invention, a substrate to which a hydroxy group or an acetoxy group is introduced may be any substrate as long as it includes at least a spirosolane skeleton. Examples of the substrate include spirosolane glycosides.

In the present invention, examples of a substrate to which a hydroxy group is introduced at position 23 include α-tomatine, α-dehydrotomatine, α-solamarine, β-solamarine, and aglycones thereof, and examples of a substrate to which an acetyl group is introduced at the hydroxy group of position 23 include leptinine, 23 hydroxy tomatine, and 23 hydroxy dehydrotomatine.

In the present invention, examples of the "leptinine" include leptinine I (3β-[2-O,4-O-bis(α-L-rhamnopyranosyl)-β-D-glucopyranosyloxy]solanid-5-en-23β-ol) and leptinine II (3β-[(3-O-β-D-glucopyranosyl-2-O-α-L-rhamnopyranosyl-β-D-galactopyranosyl)oxy]solanid-5-en-23β-ol).

In the present invention, examples of the "leptine" include leptine I (3β-[2-O,4-O-bis(α-L-rhamnopyranosyl)-β-D-glucopyranosyloxy]solanid-5-en-23β-ol 23-acetate) and 3β-[2-O,4-O-bis(α-L-rhamnopyranosyl)-β-D-glucopyranosyloxy] solanid-5-en-23β-ol), and leptine II (3β-[(3-O-β-D-glucopyranosyl-2-O-α-L-rhamnopyranosyl-β-D-galactopyranosyl)oxy]solanid-5-en-23β-acetate).

As an aspect of the "composition" of the present invention, the composition may be any composition as long as it includes, as an active component, "DNAs of the present invention" that will be described later, but may include other components. Such other components are not particularly limited. Examples thereof include sterile water, a physiological saline solution, vegetable oil, a surfactant, a lipid, a solubilizing agent, a buffer, and a preservative.

<Regarding DNA of the Present Invention>

As one example of the "DNA encoding 23DOX of the present invention" included as an active ingredient of the composition, the sequence of cDNA encoding 23DOX derived from *S. chacoense* is shown in SEQ ID NO: 1. The amino acid sequence of the protein (Sc23DOX) encoded by the aforementioned sequence is shown in SEQ ID NO: 2. As another example of the "DNA encoding 23DOX of the present invention", the sequence of cDNA encoding 23DOX derived from *S. lycopersicum* is shown in SEQ ID NO: 5. The amino acid sequence of the protein (S123DOX) encoded by the aforementioned sequence is shown in SEQ ID NO: 6. Note that, the S123DOX gene is located on the Chromosome 2, Solyc02g062460 of tomato. As another example of the "DNA encoding 23DOX of the present invention", the sequence of cDNA encoding 23DOX derived from *S. tuberosum* is shown in SEQ ID NO: 3. The amino acid sequence of the protein (St23DOX) encoded by the aforementioned sequence is shown in SEQ ID NO: 4.

As one example of the "DNA encoding 23ACT of the present invention" included as an active ingredient of the composition, the sequence of cDNA encoding 23ACT derived from *S. chacoense* is shown in SEQ ID NO: 7. The amino acid sequence of the protein (Sc23ACT) encoded by the aforementioned sequence is shown in SEQ ID NO: 8. As another example of the "DNA encoding 23ACT of the present invention", the sequence of cDNA encoding 23ACT derived from *S. lycopersicum* is shown in SEQ ID NO: 11. The amino acid sequence of the protein (S123ACT) encoded by the aforementioned sequence is shown in SEQ ID NO: 12. Note that, the S123ACT gene is located on the Chromosome 8, Solyc08g075210 of tomato. As another example of the "DNA encoding 23ACT of the present invention", the sequence of cDNA encoding 23ACT derived from *S. tuberosum* is shown in SEQ ID NO: 9. The amino acid sequence of the protein (St23ACT) encoded by the aforementioned sequence is shown in SEQ ID NO: 10.

In the current state of the art, when persons skilled in the art obtain the sequence information on the "DNA encoding 23DOX of the present invention" or the "DNA encoding 23ACT of the present invention" (these two kinds of DNAs may be collectively referred to as "DNA (s) of the present invention"), they can make various modifications to its nucleotide sequence, and can produce a mutated gene that encodes a protein having an activity to introduce a hydroxy group to position 23 of a spirosolane skeleton or a protein having an activity to acetylate the hydroxy group of position 23 of the spirosolane skeleton. Moreover, nucleotide sequences can mutate in the natural world.

Therefore, the DNA encoding 23DOX of the present invention also includes DNA encoding a protein that consists of an amino acid sequence identical to the amino acid sequence as set forth in SEQ ID NO: 2, 4, or 6 except that one or two or more amino acids are substituted, deleted, added, and/or inserted as long as it encodes a protein having an activity to introduce a hydroxy group to position 23 of a spirosolane skeleton. The DNA encoding 23ACT of the present invention also includes DNA encoding a protein that consists of an amino acid sequence identical to the amino acid sequence as set forth in SEQ ID NO: 8, 10, or 12 except that one or two or more amino acids are substituted, deleted, added, and/or inserted as long as it encodes a protein having an activity to acetylate the hydroxy group of position 23 of the spirosolane skeleton.

Here, the "two or more" amino acids generally fall within 100 amino acids (e.g., within 90 amino acids, within 80 amino acids, and within 70 amino acids), preferably within 60 amino acids (e.g., within 50 amino acids, and within 40 amino acids), more preferably within 30 amino acids (e.g., within 20 amino acids, and within 10 amino acids), and particularly preferably within several amino acids (e.g., within 5 amino acids, within 3 amino acids, and within 2 amino acids) in the whole amino acid sequence of 23DOX or 23ACT.

Mutations can be introduced to each nucleotide sequence using a conventional methods such as the Kunkel method, the Gapped duplex method, or the like, or a method based on this method using, for example, a kit for mutation introduction (e.g., Mutant-K (manufactured by Takara Bio Inc.), Mutant-G (manufactured by Takara Bio Inc.)), or LA PCR in vitro Mutagenesis series kit (manufactured by Takara Bio Inc.), which uses the site-directed mutagenesis method.

In the current state of the art, when a specific DNA is obtained, persons skilled in the art can isolate a homologous gene encoding a protein having each activity from the same kind of plant or another kind of plant by using the sequence information on the DNA. Examples of plants for obtaining such a homologous gene include solanaceous plants. Specific examples thereof include: plants belonging to *Solanum* (e.g., *Solanum panduraeforme, Solanum verbascifolium, Solanum pennellii, Solanum aethiopicum, Solanum americanum, Solanum nigrum, Solanum carolinense, Solanum betaceum, Solanum lyratum, Solanum mammosum, Solanum melongena, Solanum muricatum, Solanum pseudocapsicum*, tomato (*Solanum lycopersicum*), and *Solanum chacoense*); plants belonging to *Capsicum* (e.g., *Capsicum annuum* (e.g., green pepper and paprika), *Capsicum baccatum, Capsicum cardenasii, Capsicum chinense, Capsicum frutescens*, and *Capsicum pubescens*); plants belonging to *Nicotiana* (e.g., *N. alata* and *Nicotiana* spp.); plants belonging to *Datura* (e.g., *Datura metel, Datura inoxia*, and *Datura stramonium*); plants belonging to *Brugmansia* (e.g., *Brugmansia arborea* and *Brugmansia suaveolens*); plants belonging to *Physalis* (e.g., *Physalis alkekengi* var. *franchetii*, and *Physalis philadelphica* (Tomatillo) (*Physalis ixocarpa*)); plants belonging to *Physaliastrum*; plants belonging to *Tubocapsicum*; plants belonging to *Petunia*; plants belonging to *Scopolia*; plants belonging to *Hyoscyamu*; plants belonging to *Atropa*; plants belonging to *Mandragora*; plants belonging to *Lycium*; and plants belonging to *Calibrachoa*.

Preferable examples of plants to obtain the homologous genes of the DNAs of the present invention include plants including 23 acetoxyl spirosolane. As such plants, for example, *Solanum nigrum* is known (Eich, Soloanaceae and Convolvulaceae: Secondary Metabolite (2008), Springer, Table 7.3). Preferable examples of plants to obtain the homologous gene of the "DNA encoding 23DOX of the present invention" include plants including 23 hydroxy spirosolane. As such plants, for example, *Solanum panduraeforme* and *Solanum verbascifolium* are known (Eich, Soloanaceae and Convolvulaceae: Secondary Metabolite (2008), Springer, Table 7.3).

Examples of a method for obtaining a homologous gene include the hybridization technique (Southern, E. M., J. Mol. Biol., 98: 503, 1975) and the polymerase chain reaction (PCR) technique (Saiki, R. K., et al. Science, 230: 1350-1354, 1935, Saiki, R. K. et al. Science, 239: 487-491, 1988). In order to isolate a homologous gene, the hybridization reaction is generally performed under stringent conditions. The stringent hybridization conditions are, for example, a condition of "1×SSC, 0.1% SDS, 37° C." or other similar conditions, more stringent conditions are a condition of "0.5×SSC, 0.1% SDS, 42° C." or other similar conditions, and still more stringent conditions are a condition of "0.2×SSC, 0.1% SDS, 65° C." or other similar conditions. As the hybridization conditions are more stringent, isolation of DNA having a higher identity can be expected. Here, the above combinations of conditions including SSC, SDS, and temperature are examples, and required stringency can be achieved by appropriately combining, for example the concentration of DNA, the length of DNA, and the reaction time of hybridization.

There is no particular limitation as the "DNA encoding 23DOX of the present invention" and the "DNA encoding 23ACT of the present invention", these are preferably a sequence having 80% or higher sequence identity, more preferably a sequence having 85% or higher sequence identity, still more preferably a sequence having 90% or higher (for example, 91% or higher, 92% or higher, 93% or higher, and 94% or higher) sequence identity, and particularly preferably 95% or higher (for example, 96% or higher, 97% or higher, 98% or higher, and 99% or higher) sequence identity, to the nucleotide sequence as set forth in SEQ ID NO: 1, 3, or 5 or the nucleotide sequence as set forth in SEQ ID NO: 7, 9, or 11. The sequence identity can be determined by using, for example, BLAST (Basic Local Alignment Search Tool at the National Center for Biological Information (for example, using default, i.e., using parameters of initial settings).

Therefore, the DNA encoding 23DOX of the present invention also includes DNA that hybridizes under stringent conditions with DNA consisting of a complementary sequence to a nucleotide sequence as set forth in SEQ ID NO: 1, 3, or 5 as long as the DNA encodes a protein having an activity to introduce a hydroxy group to position 23 of a spirosolane skeleton. Moreover, the DNA encoding 23ACT of the present invention includes DNA that hybridizes under stringent conditions with DNA consisting of a complementary sequence to a nucleotide sequence as set forth in SEQ ID NO: 7, 9, or 11 as long as the DNA encodes a protein having an activity to acetylate the hydroxy group of position 23 of the spirosolane skeleton. DNA including a sequence (degenerate sequence) based on degeneracy of genetic codes in each of the nucleotide sequences is also included in each DNA of the invention of the present application.

A protein encoded by the obtained homologous gene generally has a high identity to an amino acid sequence as set forth in SEQ ID NO: 2, 4, or 6 or an amino acid sequence as set forth in SEQ ID NO: 8, 10, or 12. The term "high identity" is, for example, 80% or higher sequence identity, preferably 85% or higher sequence identity, more preferably 90% or higher sequence identity (for example, 91% or higher sequence identity, 92% or higher sequence identity, 93% or higher sequence identity, and 94% or higher sequence identity), and still more preferably 95% or higher sequence identity (for example, 96% or higher sequence identity, 97% or higher sequence identity, 98% or higher sequence identity, and 99% or higher sequence identity). The sequence identity can be determined by using BLAST (Basic Local Alignment Search Tool at the National Center for Biological Information (for example, using default, i.e., using parameters of initial settings).

Therefore, the DNA encoding 23DOX of the present invention includes DNA encoding a protein that consists of an amino acid sequence having 80% or higher identity to an amino acid sequence as set forth in SEQ ID NO: 2, 4, or 6, and has an activity to hydroxylate position 23 of a spirosolane skeleton. Moreover, the DNA encoding 23ACT of the present invention includes DNA encoding a protein that consists of an amino acid sequence having 80% or higher identity to an amino acid sequence as set forth in SEQ ID NO: 8, 10, or 12, and has an activity to acetylate a hydroxy group of position 23 of a spirosolane skeleton.

Whether a protein encoded by DNA has an activity to introduce a hydroxy group to position 23 of a spirosolane skeleton or an activity to acetylate the hydroxy group of position 23 of the spirosolane skeleton can be determined in the following manner. For example, as described in Examples below, a protein encoding the DNA is synthesized using, for example, *E. coli*. In the presence of bivalent iron ions, ascorbic acid, and 2-oxoglutaric acid, a compound having a spirosolane skeleton (e.g., α-tomatine or 23 hydroxy tomatine) is added to the obtained protein, and the mixture is allowed to react. The obtained reaction product is analyzed by a method for analyzing glycoalkaloid using liquid chromatography of Matsuda et al. (Phytochem. Anal. 15: 121-124, 2004), Kozukue et al. (J. Agric. Food Chem. 52: 2079-2083, 2004), or Nakayasu et al. (Plant Physiol. 175: 120-133), which has been generally reported (for example, the reaction product is subjected to liquid chromatography, and the obtained fractions can be analyzed through mass spectrometry or with a UV or multiwavelength detector). Note that, persons skilled in the art can appropriately set analysis conditions.

The "DNA (s) of the present invention" are not particularly limited in terms of its form. Examples thereof include genome DNA and chemically synthesized DNA in addition to cDNA. These DNAs can be prepared by using conventional methods known to persons skilled in the art. The genome DNA can be prepared in the following manner. Specifically, for example, genome DNA is extracted from a plant, to prepare a genomic library (as a vector, for example, a plasmid, a phage, a cosmid, BAC, or PAC can be used). This is developed, and is subjected to colony hybridization or plaque hybridization using a probe prepared based on a nucleotide sequence of the 23DOX gene (for example, DNA as set forth in SEQ ID NO: 1, 3, or 5) or the 23ACT gene (for example, DNA as set forth in SEQ ID NO: 7, 9, or 11). Primers specific to the 23DOX gene or the 23ACT gene are prepared, and are used to perform PCR, to thereby enable preparation of the genome DNA. Also, cDNA can be prepared in the following manner. Specifically, for example, cDNA is synthesized based on mRNA extracted from a plant. Then, the cDNA is inserted into a vector such as λZAP or the like, to prepare a cDNA library. Then, this is developed, and colony hybridization or plaque hybridization is performed in the same manner as the above method, or PCR is performed, to thereby enable preparation of the cDNA. In addition, a commercially available DNA synthesizer can be used to synthesize an intended DNA.

The DNA of the present invention may be included in the aforementioned compound in an aspect where the DNA is inserted into a vector. The vector is not particularly limited. Examples of the vector include vectors that can express an inserted DNA in a plant cell. The vector according to the present invention may include a promotor to express the DNA of the present invention constantly or inductively, and may appropriately include, for example, an enhancer, a terminator, and a selection marker.

When a transformed plant cell of the present invention is prepared by the below-described method via *Agrobacterium*, the DNA of the present invention may be included in the aforementioned compound in an aspect where the DNA is introduced to *Agrobacterium.*

More detailed aspects of the vector and *Agrobacterium* are exemplified in the following <Regarding plant cells of the present invention 1>.

<Regarding Plant Cells of the Present Invention 1>

Examples of the plant cell of the present invention that can regenerate a plant body having increased resistance against CPB include a transformed plant cell, which is obtained by introducing at least one DNA of the DNA encoding 23DOX of the present invention and the DNA encoding 23ACT of the present invention described above.

A plant from which plant cells of the present invention are derived is not particularly limited. Examples thereof include solanaceous plants such as potato and the like. The plant cell of the present invention is not limited to these plant species, but is particularly preferably general potato (*Solanum tuberosum*) that produces glycoalkaloid having a solanidane ring. Plants other than the general potato are not limited. Examples thereof include plant species, which form tubers and are included in the Potatoe subsection among *Solanum* species (Hawkes, The Potato (1990), Smithonian Inst. Press, Table 6.1).

To a plant species that has low expression levels of the 23DOX gene and the 23ACT gene or that lacks these genes, both the DNA encoding 23DOX of the present invention and the DNA encoding 23ACT of the present invention are desirably introduced in order to increase resistance against CPB. On the other hand, as described in Examples below, some species of *S. tuberosum* may naturally have at least the Sc23ACT gene. To such plant species, at least the DNA encoding 23DOX of the present invention is desirably introduced. On the contrary, to a plant species that naturally have at least the 23DOX gene, at least the DNA encoding 23ACT of the present invention is desirably introduced.

The plant cell of the present invention may be a plant culture cell, the whole plant body of a cultivated plant, a plant organ (e.g., leaf, flower, stem, root, tuber, rhizome, or seed), or a plant tissue (e.g., epidermis, phloem, parenchyma, xylem, or vascular bundle). The plant cell further includes various forms of plant cells such as suspension cultured cells, a protoplast, a leaf slice, a callus, an immature embryo, a pollen, or the like.

Examples of a method for introducing the DNA of the present invention to a plant host include: the indirect introduction method such as the *Agrobacterium* infection method or the like; and the direct introduction method such as the electroporation method, the particle gun method, the polyethylene glycol method, the liposome method, the microinjection method, or the like.

For example, when the *Agrobacterium* infection method is used, a transformed plant cell to which the DNA of the present invention is introduced can be created in the following manner.

First, a recombinant vector for transformation is prepared, followed by transformation with *Agrobacterium*. The recombinant vector for transformation can be obtained in the following manner. Specifically, after a fragment including the DNA of the present invention is cleaved with an appropriate restriction enzyme, it is linked to an appropriate linker if necessary, and the resultant is introduced into a cloning vector for a plant cell. As a result, the recombinant vector for transformation can be obtained. As the cloning vector, a binary vector-based plasmid such as pBE2113Not, pBI2113Not, pBI2113, pBI101, pBI121, PGA482, pGAH, pBIG, or the like, or an intermediate vector-based plasmid such as pLGV23Neo, pNCAT, pMON200, or the like can be used.

When the binary vector-based plasmid is used, the DNA of the present invention is inserted between the border sequences (LB and RB) of the above binary vector, and this recombinant vector is amplified in *E. coli*. Then, the amplified recombinant vectors are introduced to, for example, *Agrobacterium tumefaciens* EHA105, C58, LBA4404, EHA101, or C58C1RifR by, for example, the electroporation method, and the *Agrobacterium* to which the DNA of the present invention is introduced may be used for transformation of a plant. In addition, the triparental mating method (Nucleic Acids Research, 12: 8711 (1984)) can be used to prepare *Agrobacterium* including the DNA of the present invention to be used for transformation. That is, *E. coli* that carries a plasmid including the DNA of the present invention, *E. coli* that carries a helper plasmid (e.g., pRK2013), and *Agrobacterium* are mixed and cultured, and are cultured on a culture medium including rifampicin and kanamycin. As a result, a zygote *Agrobacterium* for transformation can be obtained.

In order to express the DNA of the present invention that is a foreign gene in a plant cell, for example, a promoter, an enhancer, or a terminator for a plant is desirably linked before or after the present invention. Examples of an available promoter in the present invention include a 35S promoter derived from cauliflower mosaic virus (CaMV), a cone ubiquitin (UBI) promoter, a nopaline synthetase (NOS) gene promoter, and an octopine (OCT) synthetase gene promoter. As the enhancer, a virus-derived translational enhancer or a plant-derived translational enhancer can be used. Examples of the virus-derived translational enhancer include the sequences of tobacco mosaic virus, alfalfa mosaic virus RNA4, brome mosaic virus RNA3, potato virus X, tobacco etch virus, and other viruses. Examples of the plant-derived translational enhancer include the sequence derived from β-1,3 glucanase (Glu) of soybean and the sequence derived from a ferredoxin-binding subunit (PsaDb) of tobacco. As the terminator, for example, a CaMV-derived terminator or a NOS gene-derived terminator can be used. Note that, the promoter, the enhancer, and the terminator are not particularly limited to the above, and any promoter, any enhancer, and any terminator can be used as long as they are known to function in a plant body. These promoter, enhancer, and terminator are linked so that the DNA of the present invention to be expressed can function.

A promoter used when the DNA of the present invention is expressed in potato is not particularly limited. The promoter may be a promoter such as the 35S promoter or the like that can express a target gene in the whole plant, and may be a promoter derived from *S. chacoense* that can express a target gene in a site other than a tuber. Examples of the promoter include a promoter of the 23DOX gene or the 23ACT gene of *S. chacoense*. Persons skilled in the art can appropriately prepare these promoters by isolating several kilobases of the upstream site of the Sc23DOX coding region or the Sc23ACT coding region.

In order to efficiently select a target transformed plant cell, a selection marker gene is preferably used. Examples of the selection marker include the kanamycin-resistant gene (NPTII), the hygromycin-resistant gene (htp), and the bialaphos-resistant genes (bar and pat). The DNA of the present invention and the selection marker gene may be incorporated into a single vector, or two kinds of recombinant DNAs, in which the DNA of the present invention and the selection marker gene are each incorporated to different vectors, may be used.

Moreover, when both the DNA encoding 23DOX of the present invention and the DNA encoding 23ACT of the present invention are introduced, these DNAs may be incorporated to a single vector, or two kinds of recombinant DNAs, in which the DNAs are each incorporated to different vectors, may be used, as described in Examples later.

As a method for introducing the DNA of the present invention to a plant host, gene insertion may be used by the genome editing method in addition to the indirect introduction method and the direct described above. The genome editing method is a method for modifying a target gene using site-specific nuclease (e.g., DNA double-strand cleavage enzyme such as Zinc finger nuclease (ZFN), transcription activator-like effector nuclease (TALEN), CRISPR-Cas9, or the like). Examples thereof include: methods using, for example, fusion proteins such as ZFNs (U.S. Pat. Nos. 6,265,196, 8,524,500, and 7,888,121, and European Patent No. 1720995), TALENs (U.S. Pat. Nos. 8,470,973 and 8,586,363), and PPR (pentatricopeptide repeat) (Nakamura et al., Plant Cell Physiol 53: 1171-1179 (2012)) fused with a nuclease domain or the like; and methods using a complex including guide RNA (gRNA) and a protein such as CRISPR-Cas9 (U.S. Pat. No. 8,697,359 and International Publication No. WO2013/176772), CRISPR-Cpf1 (Zetsche B. et al., Cell, 163 (3): 759-71, (2015)), Target-AID (K. Nishida et al., Targeted nucleotide editing using hybrid prokaryotic and vertebrate adaptive immune systems, Science, DOI: 10. 1126/science. aaf8729, (2016)), or the like.

<Regarding Plant Cells of the Present Invention 2>

As presented in the Examples later, *S. tuberosum* has the 23DOX gene and the 23ACT gene. However, *S. tuberosum* cannot sufficiently accumulate leptine because of their low expression levels. That is, increased expression of these endogenous genes can increase the leptine accumulation amount and can increase resistance against CPB.

Therefore, the present invention also provides a transformed plant cell, which is capable of regenerating a plant body having increased resistance against CPB and has more increased expression of at least one endogenous DNA selected from the group consisting of the following (a) to (h) or has more increased expression of RNA corresponding to the DNA than an untransformed plant cell.

(a) DNA encoding a protein that consists of an amino acid sequence as set forth in SEQ ID NO: 2, 4, or 6;
(b) DNA encoding a protein that consists of an amino acid sequence having 80% or higher identity to an amino acid sequence as set forth in SEQ ID NO: 2, 4, or 6, and has an activity to hydroxylate position 23 of a spirosolane skeleton;
(c) DNA encoding a protein that consists of an amino acid sequence identical to the amino acid sequence as set forth in SEQ ID NO: 2, 4, or 6 except that one or two or more amino acids are substituted, deleted, added, and/or inserted, and has the activity to hydroxylate the position 23 of the spirosolane skeleton;
(d) DNA that hybridizes under stringent conditions with DNA consisting of a complementary sequence to a nucleotide sequence as set forth in SEQ ID NO: 1, 3, or 5, and encodes a protein having an activity to hydroxylate position 23 of a spirosolane skeleton;
(e) DNA encoding a protein that consists of an amino acid sequence as set forth in SEQ ID NO: 8, 10, or 12;
(f) DNA encoding a protein that consists of an amino acid sequence having 80% or higher identity to an amino acid sequence as set forth in SEQ ID NO: 8, 10, or 12, and has an activity to acetylate a hydroxy group of position 23 of a spirosolane skeleton;
(g) DNA encoding a protein that consists of an amino acid sequence identical to the amino acid sequence as set forth in SEQ ID NO: 8, 10, or 12 except that one or two or more amino acids are substituted, deleted, added, and/or inserted, and has an activity to acetylate a hydroxy group of the position 23 of the spirosolane skeleton; and
(h) DNA that hybridizes under stringent conditions with DNA consisting of a complementary sequence to a nucleotide sequence as set forth in SEQ ID NO: 7, 9, or 11, and encodes a protein having an activity to acetylate a hydroxy group of position 23 of a spirosolane skeleton.

An increased rate of the expression compared to an untransformed plant cell is not particularly limited. The increase rate of the expression is preferably 1.1 times or higher, more preferably 1.2 times or higher, still more preferably 1.3 times or higher, and particularly preferably 1.5 times or higher.

The increase rate compared to the untransformed plant cell is calculated by measuring an expression level of at least one DNA of the DNA encoding 23DOX of the present invention and the DNA encoding 23ACT of the present invention or an expression level of RNA corresponding to those DNAs in the transformed plant cell and the untransformed plant cell through, for example, real-time PCR or semi-quantitative PCR using primers as set forth in SEQ ID NO: 30 and SEQ ID NO: 31.

Examples of a method for enhancing expression of an endogenous gene include a method for substituting a promoter upstream of each of the endogenous 23DOX gene and/or the endogenous 23ACT gene with another promoter through, for example, genomic editing or homologous recombination. Examples of the "another promoter" include the 35S promoter from CaMV described above, the UBI promoter of corn, the NOS gene promoter, the OCT synthase gene promoter, the 23DOX gene promoter of *S. chacoense*, and the 23ACT gene promoter of *S. chacoense*. The "genome editing" as used herein is not particularly limited. Examples thereof include: SDN-2 (Site-Directed Nuclease 2, a type of genome editing in which a short DNA fragment (template) homologous to a target sequence is artificially synthesized, and this is introduced in conjunction with an artificial restriction enzyme at the time of cleaving, to premeditatedly induce mutation of about one or several bases); and SDN-3 (Site-Directed Nuclease 3, a type of genome editing in which a long DNA fragment, which includes about several thousand base pairs of genes (transgene) that can be crossed and are not derived from the same species or related species, is sandwiched and introduced with a homologous sequence, to form the DNA fragment at a predetermined site on a genome). More specifically, expression of the endogenous 23DOX gene and the endogenous 23ACT gene can be increased by the following methods.

First, gRNA that recognizes 20 nucleotides including the start codon site of the St23DOX gene, a Cas9 protein, and DNA linked with a St23DOX gene promoter, a 35S promoter derived from CaMV, and the St23DOX gene are introduced into a cell in a stem slice by the electroporation method. The complex of gRNA and Cas9 incorporated into the cell cleaves the DNA between the St23DOX gene promoter and the St23DOX gene, and, at that time, the genome editing phenomenon SDN-3 occurs. As a result, the 35S promoter derived from CaMV can be inserted just upstream of the St23DOX gene. The stem slice obtained after the treatment is subcultured in a plant hormone-containing MS culture medium (containing zeatin 2 ppm, indol-3-acetic acid 0.05 ppm, and agar 0.8%) at 25° C. under 16-hour illumination (photon flux density 32 μE/m2s)/8-hour non-illumination conditions every week, which makes it possible to obtain a redifferentiated individual. DNA is extracted from the redifferentiated individual, and an individual into which the 35S promoter derived from CaMV is inserted is selected. The individual into which the 35S promoter derived from CaMV is inserted can increase an expression level of the endogenous St23DOX gene, which can produce leptinine. For the stem of the plant body, gRNA that recognizes 20 bases including the start codon site of the St23ACT gene, a Cas9 protein, and DNA linked with a St23ACT gene promoter, a 35S promoter derived from CaMV, and the St23ACT gene are similarly introduced into the cell in the stem slice by the electroporation method. As a result, an expression level of the endogenous St23DOX gene and an expression level of the endogenous St23ACT gene can be increased, and therefore leptine can be produced.

Expression of the endogenous gene can also be increased by introducing DNA encoding a factor (transcriptional activator) that activates expression of the endogenous 23DOX gene and/or the endogenous 23ACT gene. In addition, the expression of the endogenous gene can also be increased also by disrupting, through genome editing or the like, DNA encoding a factor (transcriptional repressor) that prevents expression of the endogenous 23DOX gene and/or the endogenous 23ACT gene. Persons skilled in the art can increase expression of the endogenous 23DOX gene and/or the endogenous 23ACT gene by appropriately selecting transcriptional regulators in the group of glycoalkaloid biosynthesis gene, and targeting them based on, for example, cited references. For example, persons skilled in the art can easily increase expression of the endogenous gene by targeting JRE4 (see, Thagun et al., Plant Cell Physiol. 2016 57: 961-75), which is known as a transcription factor for the group of glycoalkaloid biosynthesis gene.

<Regarding Plant of the Present Invention and its Production Method 1>

The present invention provides a plant body regenerated from the plant cell. The regeneration of the plant body from the plant cell can be performed using conventional methods known to persons skilled in the art, depending on the type of cell. For example, a plant body can be regenerated from a transformed plant cell according to the method described in, for example, "Plant Cell Culture Manual", Yasuyuki Yamada (ed), KODANSHA SCIENTIFIC, 1984, and "Transformation Protocol [Botanical Edition]", Yutaka Tabei (ed), Kagaku-Dojin Publishing Co., Inc., published on Sep. 20, 2012.

Once a transformed plant to which the DNA of the present invention has been introduced in the genome or a plant in which the expression of the endogenous DNA has been increased is obtained, a progeny can be obtained from these plants through sexual reproduction or asexual reproduction. Therefore, the plant of the present invention includes generations and individuals that can be obtained by any means of cultivation or breeding based on the TO generation, such as progenies obtained from seeds of self-propagating or outcrossing plants, in addition to the current generation "TO generation" that is redifferentiated. In addition, propagating materials (e.g., seeds, fruits, cuttings, strains, calluses, and protoplasts) can be obtained from the plant body, its progeny, or clones, and then the plant body can be mass-produced based on them. Accordingly, the present invention includes a plant cell of the present invention, a plant including the cell, a progeny and a clone of the plant, and propagating materials of the plant, the progeny, and the clone.

The present invention also provides a method for producing a plant having increased resistance against CPB, the method including: introducing, to a plant cell, the DNA encoding 23DOX of the present invention and the DNA encoding 23ACT of the present invention; and regenerating a plant from a transformed plant cell to which the DNAs are introduced in the introducing. The "increased resistance against CPB" means that resistance against CPB is increased compared to a wild-type plant.

In, for example, the thus-obtained transformed plant to which the DNAs of the present disclosure were introduced and its next generation, whether the DNAs of the present invention are incorporated can be confirmed by extracting the DNAs from these cells and tissues using conventional methods and detecting the introduced DNAs of the present invention using conventional methods (e.g., the PCR method or the southern blotting method).

The present invention also provides a method for producing a plant having increased resistance against CPB, the method including: enhancing expression of an endogenous DNA encoding 23DOX of the present invention and an endogenous DNA encoding 23ACT of the present invention; and regenerating a plant from a plant cell having increased expression of the endogenous DNAs in the enhancing.

In, for example, the thus-obtained plant having increased expression of the endogenous DNAs and its next generation, whether expression of the DNAs is increased can be confirmed by extracting mRNA or a protein from these cells and tissues using conventional methods and detecting expression of the DNAs of the present invention through detection of expression of the mRNA or the protein encoded by the DNA using conventional methods (e.g., the RT-PCR method, the northern blotting method, the ELISA method, or the western blot method).

In order to confirm whether the thus-obtained plant of the present invention has increased resistance against CPB, using CPB, the plant is investigated for the number of adult insects in a field, the number of insect damages, the adult insect consumption rate on a leaf cut in a disc shape, and the growth rate and the survival rate of larvae on a cut terrestrial part (see NPL 4), and the results can be compared to the results of a control (e.g., a plant to which the DNAs of the present invention are not introduced, a plant (e.g., wild-type) that has no increased expression of the endogenous DNAs of the present invention) to confirm that the resistance against CPB can be increased.

As described above, resistance against CPB depends on the accumulation amount of leptine. Thus, the amount of leptine is measured by an analysis method of glycoalkaloid using the aforementioned liquid chromatography, and, when the amount of leptine is greater than that of a control, it can be confirmed that resistance against CPB is increased.

<Regarding Determination Method of the Present Invention>

A method of the present invention for determining resistance against CPB in a plant includes: detecting, in a plant to be tested, presence or expression of the DNA encoding 23DOX of the present invention and the DNA encoding 23ACT of the present invention; and when the presence or expression of the DNAs is detected in the detecting, determining that the plant to be tested has resistance against CPB.

Detecting the "presence" of the DNAs of the present invention can be characterized by analyzing the DNAs in the plant to be tested or the nucleotide sequences in their expression controlling regions. Note that, the "DNA encoding 23DOX of the present invention" and the "DNA encoding 23ACT of the present invention" to be detected are described above.

For example, when the DNA encoding 23DOX of the present invention and the DNA encoding 23ACT of the present invention are not present on the genome DNA of a plant to be tested, it can be determined that the plant has no resistance against CPB. Even if the 23DOX gene and the 23ACT gene are present, CPB resistance is considered to be reduced or eliminated when a nucleotide is found to be inserted or deleted in these genes. Therefore, analysis of the DNA encoding the 23DOX of the invention and the nucleotide sequence of the 23ACT of the present invention can determine whether resistance against CPB is exhibited.

The nucleotide sequences of the regions controlling expression of the 23DOX gene and the 23ACT gene (enhancers, promoters, silencers, and insulators) can also be analyzed to determine whether resistance against CPB is exhibited.

In order to analyze nucleotide sequences of the 23DOX gene and the 23ACT gene or their expression control regions, amplification products obtained by amplifying these sequences through PCR can be used. When the PCR is performed, the primers used are not limited as long as they can each specifically amplify the genes or their expression control regions, and can be appropriately designed depending on their sequence information.

Here, a method for determining whether resistance against CPB is exhibited can include comparing with, for example, "nucleotide sequence of a control". Examples of the "nucleotide sequence of a control" to be compared to nucleotide sequences of the 23DOX gene and the 23ACT gene in a plant to be tested include nucleotide sequences encoding S123DOX, S123ACT, St23DOX, St23ACT, Sc23DOX, and Sc23ACT.

Comparison between the nucleotide sequences of the gene or its expression control region in a detected plant to be tested and the nucleotide sequence of the control can determine whether the plant to be tested has resistance against CPB. For example, when there is a significant difference in the nucleotide sequence compared to the nucleotide sequence of the control (particularly when the appearance of a new stop codon or frameshift results in significant changes in the molecular weight or the amino acid sequence of the encoded protein), it is determined that the plant to be tested is highly likely to be a plant having no resistance against CPB.

On the other hand, as shown in the examples described below, although *S. tuberosum* has the St23DOX gene and the St23ACT gene, the CPB resistance is not exhibited because the expression levels of these genes are low. Therefore, when it is compared to each of the expression control regions of the 23DOX gene and the 23ACT gene in a plant to be tested, each of the expression control regions of the S123DOX gene, the S123ACT gene, the Sc23DOX gene, and the Sc23ACT gene is used as a positive control nucleotide sequence, and each of the expression control regions of the St23DOX gene and the St23ACT gene is used as a negative control nucleotide sequence.

That is, when the nucleotide sequence of the expression control region in the detected plant to be tested has a high identity (for example, 90% or higher identity, preferably 95% or higher identity (96% or higher identity, 97% or higher identity, 98% or higher identity, 99% or higher identity; 100% identity)) with each of the expression control regions of the S123DOX gene, the S123ACT gene, the Sc23DOX gene, and the Sc23ACT gene, it is determined that the plant to be tested is highly likely to be a plant that has resistance against CPB. On the other hand, when the nucleotide sequence of the expression control region in the detected plant to be tested has a high identity (for example, 90% or higher identity, preferably 95% or higher identity (96% or higher identity, 97% or higher identity, 98% or higher identity, 99% or higher identity; 100% identity)) with each of the expression control regions of the St23DOX gene and the St23ACT gene, it is determined that the plant to be tested is unlikely to be a plant that has resistance against CPB.

As described above, even when some plants have the 23DOX gene and the 23ACT gene, such plants are unable to exhibit resistance against CPB due to their low expression levels. Therefore, it is desirable to combine the determination results using, as an indicator, the nucleotide sequences encoding the aforementioned 23DOX and the 23ACT with the determination results using, as an indicator, the nucleotide sequences of the expression control regions of the 23DOX gene and the 23ACT gene to determine whether the plant to be tested has resistance against CPB.

Detecting the "presence" of the DNAs of the invention can also be performed by detecting a DNA marker consisting of a DNA sequence that is a marker of the position where the DNA of the invention exists. As such a DNA marker, a DNA marker that is each present in, each adjacent to, or in the vicinity of the 23DOX gene and the 23ACT gene can be used.

The DNA marker available in the present invention is not particularly limited and a variety of generally known DNA markers can be suitably used. Examples thereof include microsatellite marker such as SSR (simple repeat sequence) marker, RFLP (restriction fragment length polymorphism) marker, SNP (single nucleotide polymorphism) marker, and the like.

In the determination method of the present invention, the DNA can be prepared from the plant to be tested using a conventional procedure, such as the CTAB method or the like. As a plant for preparing the DNA, not only a grown plant body but also a seed, a young plant body, and a tuber can be used. The nucleotide sequence can also be determined using a conventional procedure, such as the dideoxy method, the Maxam-Gilbert method, or the like. Commercial sequencing kits and sequencers may be used to determine base sequences.

Whether the nucleotide sequences of the 23DOX gene and the 23ACT gene or their expression control regions in the plant to be tested differ from the nucleotide sequences of the control can be analyzed indirectly by a variety of methods in addition to the direct determination of nucleotide sequences described above. Examples thereof include southern blotting, the PCR-SSCP (single-strand conformation polymorphism) method, the RFLP method and the PCR-RFLP method using restriction fragment length polymorphism (RFLP), the denaturant gradient gel electrophoresis (DGGE) method, the allele specific oligonucleotide (ASO) hybridization method, and the ribonuclease A mismatch cleavage method.

The determination method of the present invention is characterized by detecting expression of the DNA encoding 23DOX of the present invention and the DNA encoding 23ACT of the present invention in a plant to be tested.

The "detecting expression of DNA" used herein includes both detection at a transcriptional level and detection at a translational level. Furthermore, "detection of expression" means not only detection of presence or absence of expression but also detection of the extent of expression, and also includes detection of a molecular weight of an expression product of DNA.

Detection of the DNA of the present invention at a transcriptional level can be performed using a conventional procedure, such as the RT-PCR (Reverse transcribed-Polymerase chain reaction) method, the Northern blotting method, or the like. The primers used in performing the PCR are not particularly limited as long as the DNAs of the present invention can be specifically amplified, and can be appropriately designed based on the nucleotide sequences of the DNAs.

On the other hand, detection at a translational level can be performed using a conventional procedure, such as the Western blotting method, the ELISA method, or the like. Antibodies used in Western blotting may be polyclonal or monoclonal antibodies, and methods for preparing these antibodies are well known to persons skilled in the art.

As a result of detecting the expression, a plant to be tested is determined to have no resistance against CPB or to have low resistance against CPB when the expression level of the DNA of the present invention is significantly lower than that of a CPB-resistant plant (e.g., *S. chacoense*) or is lower than or equivalent to that of a CPB non-resistant plant (e.g., *S. tuberosum*) (for example, when the DNA of the invention is not substantially expressed), or a molecular weight of an expression product of the DNA of the present invention is significantly different from the molecular weight of a CPB-resistant plant.

<Regarding Plant of the Present Invention and its Production Method 2>

The present invention provides a method for producing a plant that has resistance against CPB using the determination method.

The production method includes: crossing a plant having resistance against Colorado potato beetle, with an arbitrary plant; determining the resistance against CPB in a plant obtained in the crossing, by the aforementioned method, and selecting a plant that is determined to have the resistance against CPB.

In addition, the method includes: crossing a plant having DNA encoding 23DOX of the present invention with a plant having DNA encoding 23ACT of the present invention; determining the resistance against CPB in a plant obtained in the crossing, by the aforementioned method; and selecting a plant that is determined to have the resistance against CPB.

The "plant having resistance against CPB" is not particularly limited as long as it has the resistance or an ability to biosynthesize leptine. Examples thereof include *S. chacoense*.

Examples of the "arbitrary plant" crossed with the variety include, but are not limited to, varieties having no resistance against CPB, and plants obtained by crossing plant varieties having resistance against CPB with varieties having no resistance against CPB. The term "arbitrary plant" may also have another property other than resistance against CPB. Example of the "another property" include, but are not limited to, resistance against pests other than CPB, resistance against various diseases, high yields, and early maturing.

The "plant having DNA encoding 23DOX of the present invention" may be any plant as long as it includes at least DNA encoding 23DOX. Examples thereof include plants having at least DNA encoding Sc23DOX: *S. chacoense*. The "plant having DNA encoding 23ACT of the present invention" may be any plant as long as it includes at least DNA encoding 23DOX. Examples thereof include plants having at least DNA encoding Sc23ACT: *S. chacoense* and *S. tuberosum* (e.g., Konafubuki, 97H32-6, Saikai 35, SAKURAFUBUKI, and pearlstarch).

In addition, use of the production method of the present invention enables selection of plants having resistance against CPB at, for example, a young plant stage, and enables cultivation of varieties having the characteristics in a short period of time. Therefore, the present invention also provides a method for breeding a plant having resistance against CPB.

The method includes: crossing a variety having resistance against CPB and with an arbitrary plant variety (plant line) or crossing a plant having DNA encoding 23DOX of the present invention with a plant having DNA encoding 23ACT of the present invention; and selecting presence or expression of the DNAs of the present invention as an indicator as described above, which therefore enables breeding. One example of a more specific selective breeding method includes a method including: crossing an arbitrary plant variety (e.g., *S. tuberosum*) with a plant variety having the DNA of the present invention (e.g., *S. chacoense*), to obtain a hybrid; backcrossing the obtained hybrid with the arbitrary plant variety; selecting a hybrid having the DNA of the present invention; and performing additional backcrossing. The backcrossing and the selecting are repeated several times, and preferably repeated 2 to 10 times. This method makes it possible to obtain a commercial variety having the DNA of the present invention.

The present invention also provides a plant that has resistance against CPB and is produced in this manner. The plant is not particularly limited as long as it has at least the DNA of the invention, but a substitution rate in the arbitrary plant variety on the whole chromosome is preferably 50% or more (e.g., 60% or more), more preferably 70% or more (e.g., 80% or more), and even more preferably 90% or more (e.g., 95% or more, 96% or more, 97% or more, 98% or more, and 99% or more). The substitution rate can be obtained by analyzing DNA marker present throughout the genome and calculating the rate in the arbitrary plant variety. Breeding through the DNA marker selection may also be performed according to, for example, Hamwieh et al. (2011) Euphytica, 179: 451-459.

<Regarding Kit Used in Determination Method of the Present Invention>

As described above, the presence or absence of resistance against CPB in a plant can be determined by detecting DNA encoding 23DOX and DNA encoding 23ACT of the present invention. Therefore, the present invention is an agent for determining resistance against CPB in a plant by the above-described determination method and includes at least one compound selected from the group consisting of (a) to (d) below:

(a) an oligonucleotide having a chain length of at least 15 nucleotides that hybridizes with a gene encoding the 23DOX of the present invention, a transcription product thereof, or a complementary nucleotide thereof;

(b) an oligonucleotide having a chain length of at least 15 nucleotides that hybridizes with a gene encoding the 23ACT of the present invention, a transcription product thereof, or a complementary nucleotide thereof;

(c) an antibody that binds to the 23DOX of the present invention; and (d) an antibody that binds to the 23ACT of the present invention.

The oligonucleotide according to the present invention may be in the form of a primer or in the form of a probe, in accordance with the above detection method.

The primers are not particularly limited as long as they hybridize with a gene encoding the 23DOX of the present invention or a gene encoding the 23ACT of the present invention (genome DNA), a transcription product thereof (mRNA) or a complementary nucleotide thereof (cDNA, CRNA), and can amplify and detect, for example, the transcription product. The primers may be only DNA, or part or all of the primers may be substituted with an artificial nucleic acid (modified nucleic acid), such as a cross-linked nucleic acid or the like. The size of the primers may be at least about 15 nucleotides long, preferably 15 to 100 nucleotides long, more preferably 18 to 50 nucleotides long, and even more preferably 20 to 40 nucleotides long. Persons skilled in the art can design and produce such primers by conventional methods in accordance with the above detection methods.

The probe is not particularly limited as long as it hybridizes with a gene encoding the 23DOX of the present invention or to a gene encoding the 23ACT of the present invention, a transcription product thereof, or a complementary nucleotide thereof, and can detect them. The probe can be, for example, DNA, RNA, an artificial nucleic acid, or a chimeric molecule thereof. The probe can be either single-stranded or double-stranded. The size of the probe may be any size as long as it is at least about 15 nucleotides long, and the size is preferably 15 to 1000 nucleotides long, more preferably 20 to 500 nucleotides long, and even more preferably 30 to 300 nucleotides long. Persons skilled in the art can produce such probes by conventional methods. The probe may also be provided in the form of being immobilized on a substrate, such as a microarray or the like.

The antibody is not particularly limited as long as it can specifically bind to the 23DOX or the 23ACT of the present invention. For example, the antibody may be any of a polyclonal antibody and a monoclonal antibody, or may also be a functional fragment of the antibody (e.g., Fab, Fab', scFv). Persons skilled in the art can produce such antibodies by conventional methods. The antibody may also be provided in the form of being immobilized on a substrate, such as a plate or the like, for use in the ELISA method, antibody arrays, or the like.

The oligonucleotide or antibody contained in the kit of the present invention may also be labeled with a labeling substance depending on the detection method. Examples of the labeling substance include: fluorescent substances such as FITC, FAM, DEAC, R6G, TexRed, Cy5, and the like; enzymes such as β-D-glucosidase, luciferase, HRP, and the like; radioactive isotopes such as $^{3}H$, $^{14}C$, $^{32}P$, $^{35}S$, $^{123}I$, and the like; affinity substances such as biotin, streptavidin, and the like; and luminescent materials such as luminol, luciferin, lucigenin, and the like.

Also, the oligonucleotide or antibody may be in the form that includes other components acceptable as a composition. Examples of the other components include carriers, excipients, disintegrators, buffers, emulsifiers, suspensions, stabilizers, preservatives, antiseptics, physiological saline, and secondary antibodies.

The kit of the present invention may also be combined with, for example, a substrate necessary for detecting a label, positive and negative controls, or a buffer used for diluting and washing samples, in addition to the above oligonucleotide and the antibody. In addition, the kit may include instructions of the kit.

Suitable embodiments of the present invention have been explained above, but the present invention shall not be construed as being limited to the above embodiments. For example, the plant cell, the plant, its production method of the present invention, the determination method of the present invention, and the plant production method using the determination method can be applied to achieve, for example, not only resistance against CPB but also production of leptine, like the composition of the present invention. That is, the present invention also provides the following aspects.

<12> A plant cell that is capable of regenerating a plant body having an increased accumulation amount of leptine, the plant cell including:

at least one DNA selected from the group consisting of (a) to (h) below, the at least one DNA being introduced to the plant cell, (a) DNA encoding a protein that consists of an amino acid sequence as set forth in SEQ ID NO: 2, 4, or 6;

(b) DNA encoding a protein that consists of an amino acid sequence having 80% or higher identity to an amino acid sequence as set forth in SEQ ID NO: 2, 4, or 6, and has an activity to hydroxylate position 23 of a spirosolane skeleton;

(c) DNA encoding a protein that consists of an amino acid sequence identical to the amino acid sequence as set forth in SEQ ID NO: 2, 4, or 6 except that one or two or more amino acids are substituted, deleted, added, and/or inserted, and has an activity to hydroxylate the position 23 of the spirosolane skeleton;

(d) DNA that hybridizes under stringent conditions with DNA consisting of a complementary sequence to a nucleotide sequence as set forth in SEQ ID NO: 1, 3, or 5, and encodes a protein having an activity to hydroxylate position 23 of a spirosolane skeleton;

(e) DNA encoding a protein that consists of an amino acid sequence as set forth in SEQ ID NO: 8, 10, or 12;

(f) DNA encoding a protein that consists of an amino acid sequence having 80% or higher identity to an amino acid sequence as set forth in SEQ ID NO: 8, 10, or 12, and has an activity to acetylate a hydroxy group of position 23 of a spirosolane skeleton;

(g) DNA encoding a protein that consists of an amino acid sequence identical to the amino acid sequence as set forth in SEQ ID NO: 8, 10, or 12 except that one or two or more amino acids are substituted, deleted, added, and/or inserted, and has an activity to acetylate a hydroxy group of the position 23 of the spirosolane skeleton; and (h) DNA that hybridizes under stringent conditions with DNA consisting of a complementary sequence to a nucleotide sequence as set forth in SEQ ID NO: 7, 9, or 11, and encodes a protein having an activity to acetylate a hydroxy group of position 23 of a spirosolane skeleton.

<13> A plant cell that is capable of regenerating a plant body having an increased accumulation amount of leptine, wherein expression of at least one endogenous DNA selected from the group consisting of the (a) to (h) is increased.

<14> A plant that is regenerated from the plant cell according to <12> or <13> and has an increased accumulation amount of leptine.

<15> A method for producing a plant having an increased accumulation amount of leptine, the method including:

introducing, to a plant cell, at least one DNA selected from the group consisting of the (a) to (h); and regenerating a plant from a transformed plant cell to which the DNA is introduced in the introducing.

<16> A method for determining an ability to generate leptine in a plant, the method including:

detecting, in a plant to be tested, presence or expression of at least one DNA selected from the group consisting of the (a) to (d) and at least one DNA selected from the group consisting of the (e) to (h); and when the presence or expression of the DNAs is detected in the detecting, determining that the plant to be tested has an ability to generate leptine.

<17> A method for producing a plant having an ability to generate leptine, the method including:

crossing a plant having an ability to generate leptine with an arbitrary plant;

determining, by the method according to <16>, the ability to generate leptine in an individual obtained in the crossing; and selecting a plant that is determined to have the ability to generate leptine.

<18> A method for producing a plant having an ability to generate leptine, the method including:

crossing a plant having at least one DNA selected from the group consisting of the (a) to (d) with a plant having at least one DNA selected from the group consisting of the (e) to (h);

determining, by the method according to <16>, an ability to generate leptine in a plant obtained in the crossing; and selecting a plant that is determined to have the ability to generate leptine.

As described above, according to the present invention, a plant that has an ability to generate leptine can be obtained. Therefore, the present invention can be applied to, for example, organisms that are prevented from feeding by leptine, organisms that avoid leptine, organisms that are prevented from growing by leptine, and organisms that are killed by leptine, in addition to CPB.

All the references recited in the present specification are incorporated herein by reference as they are.

EXAMPLES

Hereinafter, the present invention will be described in detail by way of Examples, and the present invention shall not be construed as being limited to the following Examples.

It is revealed that the wild species potato *S. chacoense* exhibits resistance against CPB by accumulating leptines (leptine I and leptine II). Moreover, as shown in the lower part of FIG. 1, it is assumed that hydroxylation of position 23 of solanidanes (α-chaconine and α-solanine) produces leptinine I and leptinine II, followed by acetylation of the hydroxy groups of the position 23 of these compounds, to thereby accumulate leptines (see NPL 5). However, a gene that is involved with production of leptines and imparts resistance against CPB to *S. chacoense* has not been identified.

In order to identify the gene, the present inventors focused on the metabolic process (the upper part of FIG. 1) of a spirosolane glycoside (α-tomatine) in tomato (*S. lycopersicum*) that is the same solanaceous plant. The present inventors assumed that 23-position hydroxylase (also referred to as "23DOX") and 23-position acetyltransferase (also referred to as "23ACT") were involved with production of leptines in *S. chacoense*, similarly with the metabolic process of spirosolane glycoside in the tomato, and tried to identify genes encoding these enzymes in *S. chacoense* in the following manner. In tomato, the sequences of the genes encoding these enzymes have not been revealed. Therefore, they started to identify the sequences of the genes in tomato first.

(Example 1) Acquisition of 23DOX Gene

It is revealed that the metabolism of the spirosolane glycoside (production of esculeoside A from tomatine) in tomato is caused in the maturation process of the fruit. Therefore, the present inventors tried to identify a gene encoding hydroxylase (dioxygenase) expressed in the fruit of tomato.

Specifically, RNA was extracted from the fruit of dwarf tomato species Micro-Tom using an RNA extraction kit (product name: RNeasy, manufactured by QIAGEN), and cDNA was prepared using a cDNA synthesis kit for real-time PCR (product name; ReverTra Ace (Registered Trademark) qPCR RT Kit, manufactured by TOYOBO CO., LTD.).

On the other hand, the sequence (Solyc02g062460) encoding a protein having a structure of the dioxygenase specifically expressed in the fruit was found in the expression database of tomato (Sol Genomics Network: https://solgenomics.net/).

For the cDNA of the tomato fruit as a template, primers GGATCCATGGCATCTATCAAATCAG (SEQ ID NO: 13) and CTCGAGTCAAAATACCACAATAAATCTTG (SEQ ID NO: 14), which were synthesized based on the aforementioned sequence, were used to perform PCR (30 cycles, manufactured by Takara Bio Inc., using Ex taq HS) at an annealing temperature of 55° C., to amplify the gene. This was cloned into a pMD19 vector (manufactured by Takara Bio Inc.), to obtain a gene fragment, followed by determining the full-length sequence (the protein encoded by this gene is also referred to as "S123DOX". This amino acid sequence is shown in SEQ ID NO: 6).

Next, from a leaf of *S. chacoense* PI 458310 (seeds obtained from USDA Potato Genbank were seeded) that was expressing leptines, RNeasy (manufactured by QIAGEN) was used to extract RNA, and a ReverTra Ace qPCR RT Kit (manufactured by TOYOBO CO., LTD.) was used to prepare cDNA. The exhaustive analysis of the nucleotide sequence of *S. chacoense* has not progressed, and most of the sequence remained unclear. Therefore, degenerate primers CTWAAACCAAACACTYCAYWATGGGAAT (SEQ ID NO: 15) and GGGTGTTYWTCATCYACWARTTCTTTTGG (SEQ ID NO: 16), which were prepared based on the sequence of the S123DOX gene, were used to perform PCR (30 cycles, manufactured by TOYOBO CO., LTD., using KOD FX Neo) at an annealing temperature of 55° C. The obtained PCR amplification product was cloned into a pCR4Blunt-TOPO vector (manufactured by Thermo Fisher Scientific), to obtain a gene fragment, followed by determining a partial sequence.

Then, the full-length ORF sequence of the cDNA fragments was determined by the RACE method. More specifically, a SMARTer RACE CDNA Amplification Kit (manufactured by Clontech Laboratories, Inc.) was used to synthesize cDNA for RACE from RNA of *S. chacoense* according to the protocol of the kit. For the cDNA for RACE as a template, the universal primer affixed to the kit and the gene-specific primer TGGTGATTACCCTGAGGCCAAAAGA (SEQ ID NO: 17) in 5'-RACE, and the gene-specific primer GGTCGATTGCATTCTCCTGTCCAC (SEQ ID NO: 18) and the universal primer affixed to the kit in 3'-RACE were each used to perform PCR (35 cycles, manufactured by Takara Bio Inc., using Ex Taq HS) at an annealing temperature of 58° C.

The amplified genes were cloned into a pMD19 vector (manufactured by Takara Bio Inc.) to analyze the sequences of gene fragments. As a result, a sequence expected to be a start codon was found in the fragment obtained through 5'-PACE, and a stop codon was found in the fragment obtained through 3'-RACE.

Then, for the cDNA of *S. chacoense*, primers CATATGGCATCTACCAAATCAGTTAAAGT (SEQ ID NO: 19) and GTCGACTCAAACACCGCAATAAGTCTTGA (SEQ ID NO: 20), which were prepared based on the base sequence of the RACE fragment, were used to perform PCR (35 cycles, manufactured by Takara Bio Inc., using PrimeSTAR HS) at an annealing temperature of 55° C. The obtained PCR amplification product was cloned into a pCR4Blunt-TOPO vector (manufactured by Thermo Fisher Scientific), to obtain a gene fragment, followed by determining the full-length sequence (the amino acid sequence encoded by the determined sequence is shown in SEQ ID NO: 2. The protein encoded by this gene is also referred to as "Sc23DOX".). Note that, S123DOX and Sc23DOX had a sequence identity of 87% in terms of an amino acid level.

(Example 2) Acquisition of 23ACT Gene

Like the above hydroxylase, the present inventors tried to identify a gene encoding acetyltransferase expressing in the fruit of tomato. Specifically, the sequence (Solyc08g075210) encoding a protein that has a structure of the acetyltransferase expressed in the fruit was found in the expression database of tomato (Sol Genomics Network: https://solgenomics.net/). For the CDNA of the tomato fruit, primers GGATCCCATATGACAGCATCAAGTTTTGTATCTATG (SEQ ID NO: 21) and GTCGACCTAGAGATTCGTAACTGGAGAAGC (SEQ ID NO: 22), which were synthesized based on the aforementioned sequence, were used to perform PCR (40 cycles, manufactured by Takara Bio Inc., using PrimeStar HS) at an annealing temperature of 55° C., to amplify the gene. This was cloned into a pCR4Blunt-TOPO vector (manufactured by Thermo Fisher Scientific), to obtain a gene fragment, followed by determining the full-length sequence (hereinafter, a protein encoded by this gene is also referred to as "S123ACT". This amino acid sequence is shown in SEQ ID NO: 12).

RNA extracted from a leaf of *S. chacoense* was exhaustively sequenced using a next-generation sequencer to prepare EST (expressed sequence tag) database. In the EST database, S123DOX is used as a query sequence to perform blast, and a 3' fragment of a gene considered to encode the acetyltransferase was found.

Then, a 5' fragment of the gene was obtained, and the RACE method was performed in order to determine the full-length ORF sequence. The RACE method was performed using SMARTer RACE cDNA Amplification Kit (manufactured by Clontech Laboratories, Inc.). More specifically, according to the protocol of the kit, cDNA for RACE was synthesized from RNA of *S. chacoense*. For the cDNA for RACE as a template, the universal primer affixed to the kit and the gene-specific primer TGCCATCCACTGGCATTCACATGG (SEQ ID NO: 23) were used to perform PCR (35 cycles, manufactured by Takara Bio Inc., using Ex Taq HS) at an annealing temperature of 58° C., to amplify the gene. Then, the obtained amplification product was cloned into a pMD19 vector (manufactured by Takara Bio Inc.), followed by sequence analysis of the gene fragment. As a result, a sequence expected to be a start codon was found in the fragment obtained by 5'-RACE.

In order to determine the full-length ORF sequence of a gene that was considered to encode acetyltransferase, using cDNA of *S. chacoense* as a template, primers CATATGGCAGCATCAAGTIGTGTAT (SEQ ID NO: 24) and GTCGACTTAATTAAGATTAGTAATTGGAGAAGA (SEQ ID NO: 25), which were prepared based on the base sequences of the fragments, were used to perform PCR (30 cycles, manufactured by Takara Bio Inc., using PrimeStar) at an annealing temperature of 55° C., to amplify the gene. The obtained PCR product was cloned into a pENTR/D-TOPO vector (manufactured by Thermo Fisher Scientific) to obtain a gene fragment, followed by determining the full-length sequence (Sc23ACT, its amino acid sequence is shown in SEQ ID NO: 8.). Note that, S123ACT and Sc23ACT had an amino acid same homology of 30%.

(Example 3) Detection of In Vitro Enzyme Activity of 23DOX

Whether the protein encoded by the gene identified in Example 1 was able to introduce a hydroxy group to position 23 of these compounds using α-tomatine or α-solanine as a substrate as assumed was examined in the following manner.

First, in order to synthesize 23DOX in *E. coli*, the S123DOX gene and the Sc23DOX gene were each linked to a pCold ProS2 vector (manufactured by Takara Bio Inc.), and were introduced into *E. coli* BL21 (DE3). The obtained recombinant *E. coli* was cultured at 37° C. until the $OD_{600}$ value reached 0.5, was cooled to 15° C., and was left to stand for 30 minutes. IPTG was added thereto so that the final concentration reached 0.1 mM, and the mixture was cultured under shaking at 15° C. for 24 hours, to induce expression of the recombinant protein.

Then, the *E. coli* bodies whose expression was induced were collected, and were suspended in a sonication buffer [50 mM Bis-Tris-HCl (pH 7.0), 150 mM NaCl, 1 mM dithiothreitol, 10% glycerol]. After an ultrasonic crushing machine was used to crush bacterial cells, the mixture was subjected to centrifugal separation, and crude extraction fractions were obtained from the supernatant. A 100 mM Bis-Tris-HCl solution (pH 7.2, containing 5 mM 2-oxoglutaric acid, 10 mM sodium ascorbate, and 200 μM $FeSO_4$) containing a 50 μM substrate was added to the mixture, and was allowed to react.

The obtained reaction product was analyzed through LC-MS (manufactured by Waters, product name: UPLC-ESI-MS ACQUITY). As the column, ACQUITY HSS T3 1.8 μm φ 2.1×100 mm (manufactured by Waters) was used. In LC analysis, gradient elution was performed using a mobile phase (A: 0.1% formic acid water and B: acetonitrile). The gradient elution was performed under the condition: maintaining for from 0 to 3 minutes, 90% A/10% B; 3 to 33 minutes, 90% A/10% B to 57.5% A/42.5% B; 33 to 33 minutes, 57.5% A/42.5% B to 0% A/100% B; and maintaining for from 38 to 43 minutes, 100% B.

Figure 2:
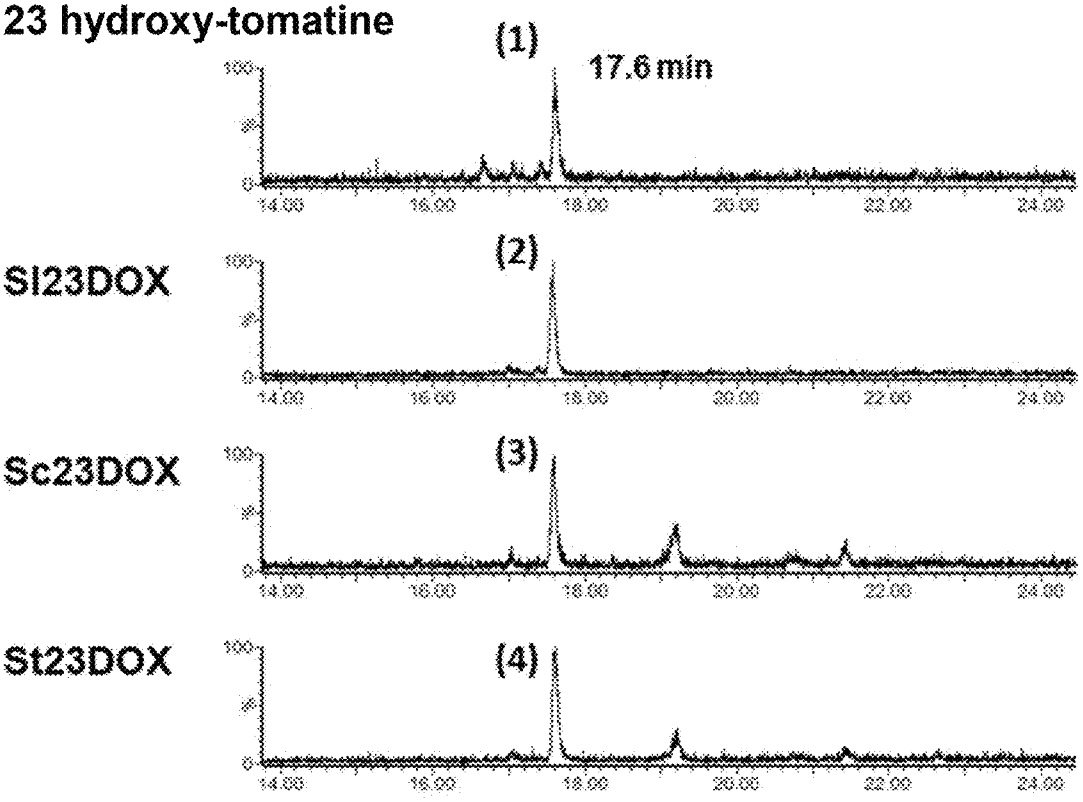
FIG. 2 is chart data of LC-MS showing the results of the 23-position hydroxylase activity detected using crude extraction fractions of *E. coli* (in the figure, the respective signs are shown as "S123DOX", "Sc23DOX", and "St23DOX".) to which a vector for expressing 23DOX derived from *S. lycopersicum*, a vector for expressing 23DOX derived from *S. chacoense*, and a vector for expressing 23DOX derived from *S. tuberosum* are each introduced. In the figure, the longitudinal axis shows intensity and the horizontal axis shows retention time (regarding the signs in the figure, the same is applied to FIGS. 4, 7, 9, 13, and 14)
Figure 3:
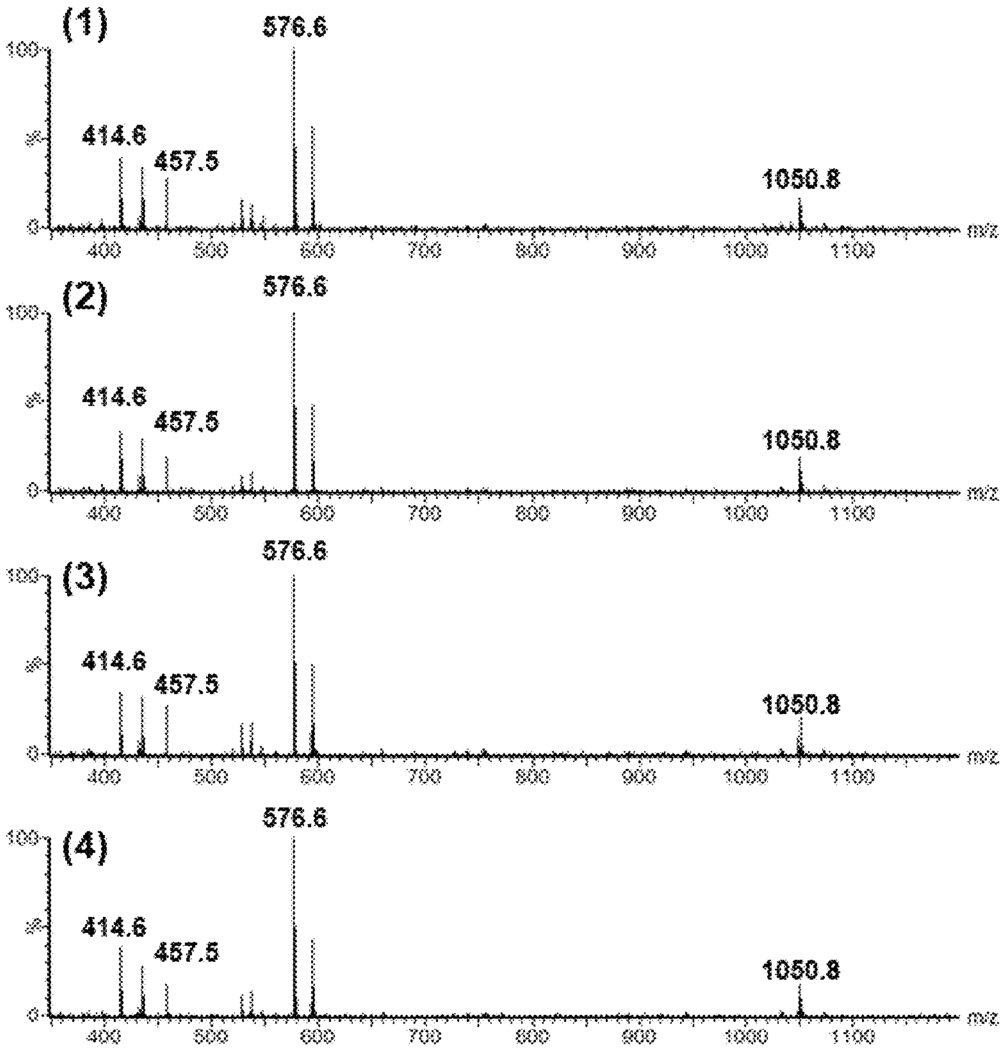
FIG. 3 is the mass spectra of the peaks (1) to (4) shown in FIG. 2. In the figure, the longitudinal axis shows intensity and the horizontal axis shows the mass-to-charge ratio (regarding the signs in the figure, the same is applied to FIGS. 5, 8, 10, and 15)

As a result, as shown in FIG. 2 and FIG. 3, it was revealed that a product to which a hydroxy group was introduced at position 23 was obtained not only in those derived from *S. lycopersicum* (S123DOX) but also in 23DOX (Sc23DOX) derived from *S. chacoense* when α-tomatine was a substrate.

However, a new reaction product was not obtained in both S123DOX and Sc23DOX when α-solanine was a substrate (not illustrated in the figures).

(Example 4) Detection of In Vitro Enzyme Activity of 23ACT

Whether the protein encoded by the gene identified in Example 2 was able to acetylate a hydroxy group of position 23 of these compounds using 23 hydroxy tomatine, leptinine I, or leptinine II as a substrate as assumed was examined in the following manner.

First, in order to synthesize 23ACT in vitro, the S123ACT gene and the Sc23ACT gene were each linked to a pCold ProS2 (manufactured by Takara Bio Inc.), and were introduced into *E. coli* BL21 (DE3). The obtained recombinant *E. coli* was cultured at 37° C. until the $OD_{600}$ value reached 0.5, was cooled to 15° C., and was left to stand for 30 minutes. IPTG was added thereto so that the final concentration reached 0.1 mM, and the mixture was cultured under shaking at 15° C. for 24 hours, to induce expression of the recombinant protein. Then, the *E. coli* bodies whose expression was induced were collected, and were suspended in a sonication buffer [50 mM Bis-Tris-HCl (pH 7.0), 150 mM NaCl, 1 mM dithiothreitol, 10% glycerol]. After an ultrasonic crushing machine was used to crush bacterial cells, the mixture was subjected to centrifugal separation, and crude extraction fractions were obtained from the supernatant. A 100 mM Bis-Tris-HCl solution (pH 7.2, containing 400 μM acetyl COA) containing a 50 μM substrate was added to the mixture, and was allowed to react.

The obtained reaction product was analyzed through LC-MS (manufactured by Waters, product name: UPLC- ESI-MS ACQUITY). As the column, ACQUITY HSS T3 (1.8 μm φ2.1×100 mm) (manufactured by Waters) was used. In LC analysis, gradient elution was performed using a mobile phase (A: 0.1% formic acid water and B: acetonitrile). The gradient elution was performed under the condition: 0 to 30 minutes, 90% A/10% B to 45% A/55% B; 30 to 31 minutes, 45% A/55% B to 100% B; and maintaining for from 31 to 35 minutes, 100% B.

Figure 4:
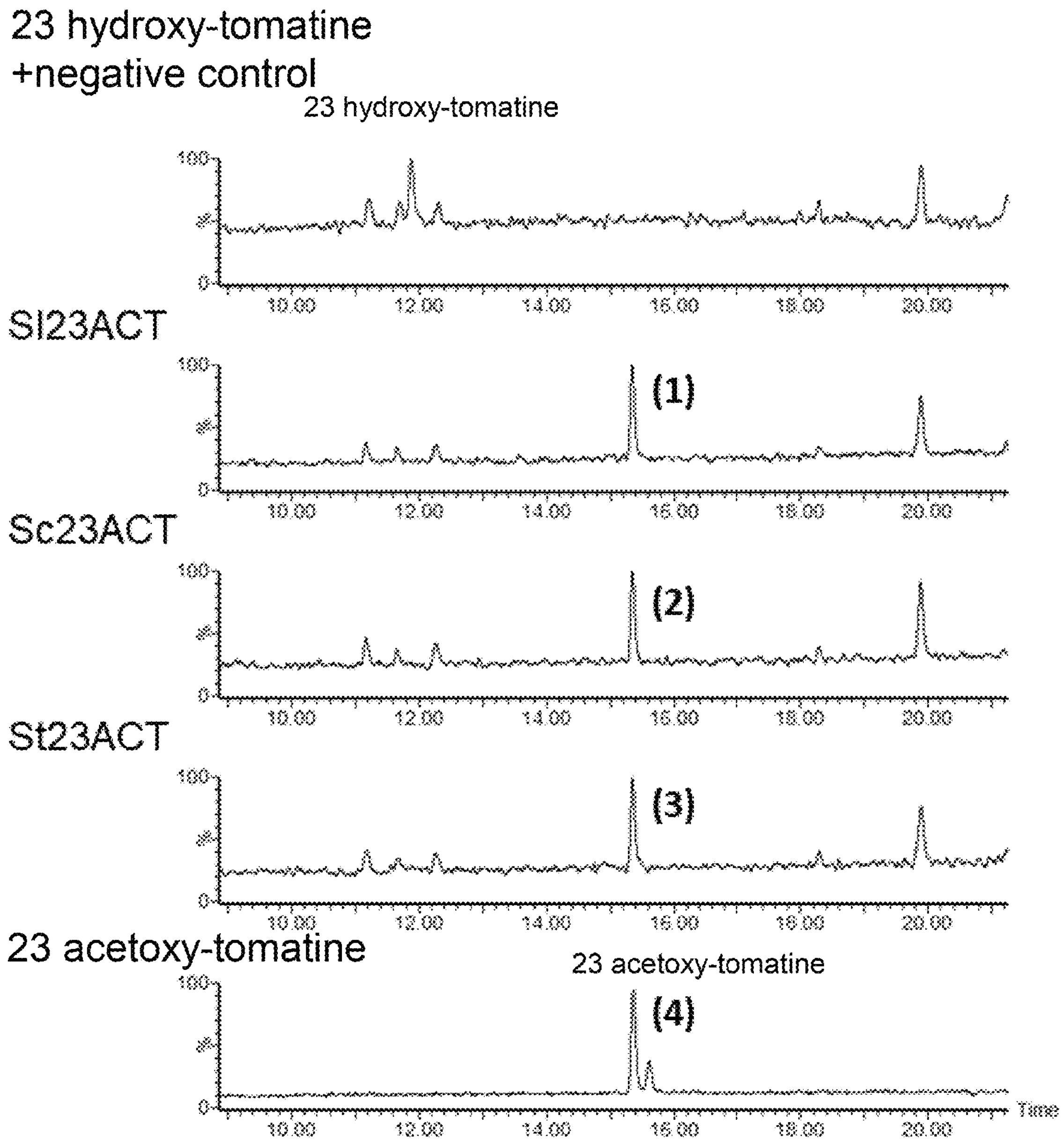
FIG. 4 is chart data of LC-MS showing the results of the 23-position acetyltransferase detected using crude extraction fractions of *E. coli* (in the figure, the respective signs are shown as "S123ACT", "Sc23ACT", "St23ACT", and "23 hydroxy-tomatine+negative control".) to which a vector for expressing 23ACT derived from *S. lycopersicum*, a vector for expressing 23ACT derived from *S. chacoense*, a vector for expressing 23ACT derived from *S. tuberosum*, and an empty vector are each introduced. In the figure, "23 acetoxy-tomatine" shows chart data of its specimen.
Figure 5:
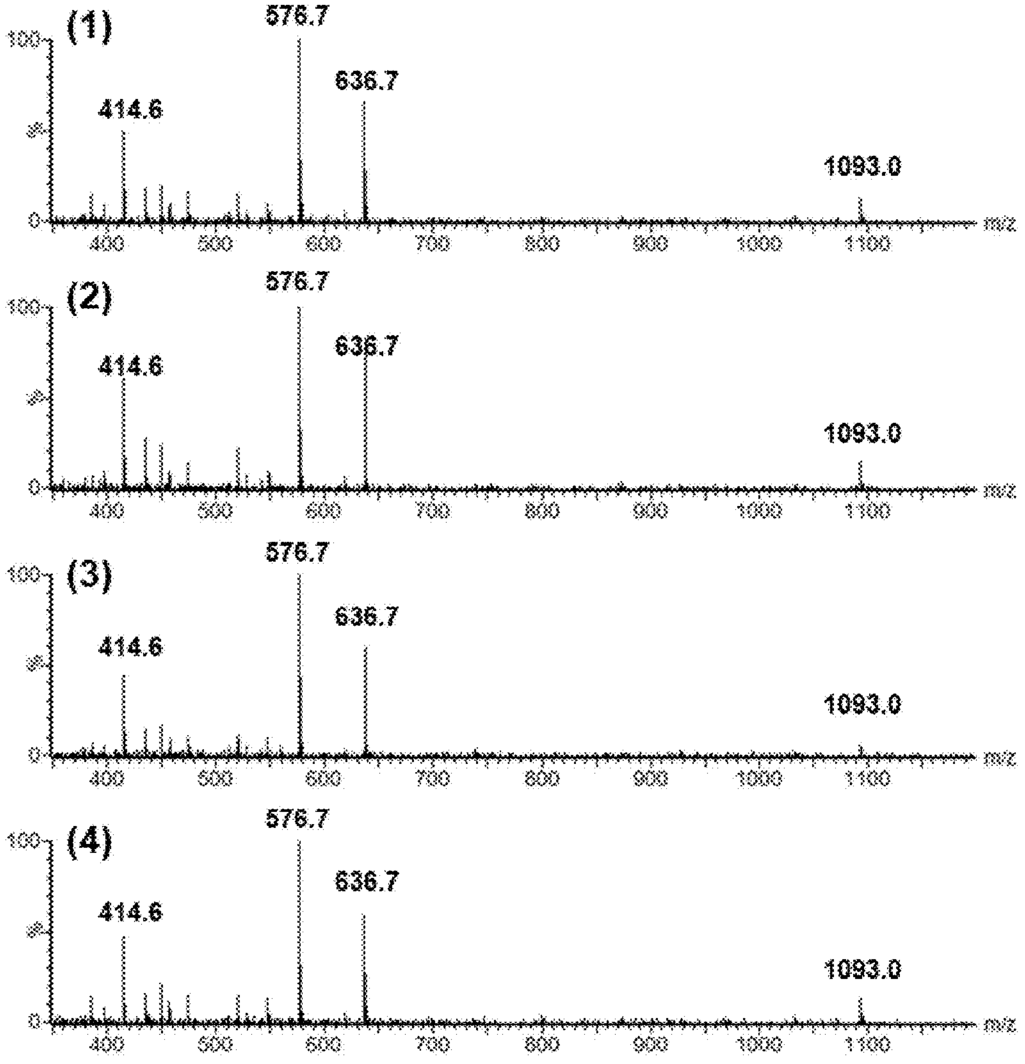
FIG. 5 is the mass spectra of the peaks (1) to (4) shown in FIG. 4.

As a result, as shown in FIG. 4 and FIG. 5, it was revealed that a product to which an acetoxy group was introduced at position 23 was obtained in the presence of S123ACT or Sc23ACT when 23 hydroxy tomatine was a substrate.

On the other hand, a new reaction product was not obtained in both S123ACT and Sc23ACT when leptinine I or leptinine II was a substrate (not illustrated in the figures).

As described above, it was revealed that 23DOX and 23ACT of tomato and *S. chacoense* encoded by the genes identified this time catalyze hydroxylation reaction and acetylation reaction at position 23 of α-tomatine (spirosolane skeleton). On the other hand, the involvement of these enzymes was not observed in the previously assumed reaction process from α-solanine (solanidane skeleton) to leptine. That is, it was suggested that 23DOX and 23ACT are enzymes that specifically act on a compound having a spirosolane skeleton.

(Example 5) Analysis of Steroid Glycoalkaloid in Potato to which 23DOX Gene is Introduced A transformed potato to which the 23DOX gene derived from *S. chacoense* was introduced was created. Then, whether leptinine I and leptinine II were produced in this transformed body was examined in the following manner.

Figure 6:
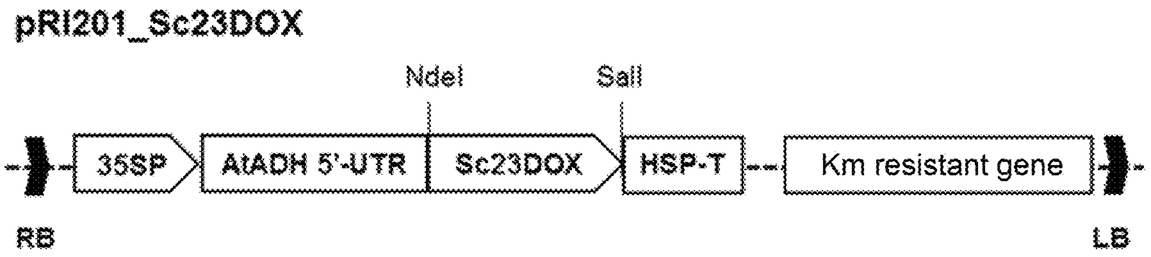
FIG. 6 is a view illustrating the structure of a vector used for transformation. The figure shows a right border (RB), a left border (LB), the inner structures in the borders, and a restriction enzyme recognition sequence site in T-DNA of a gene site to be introduced.
Figure 6:
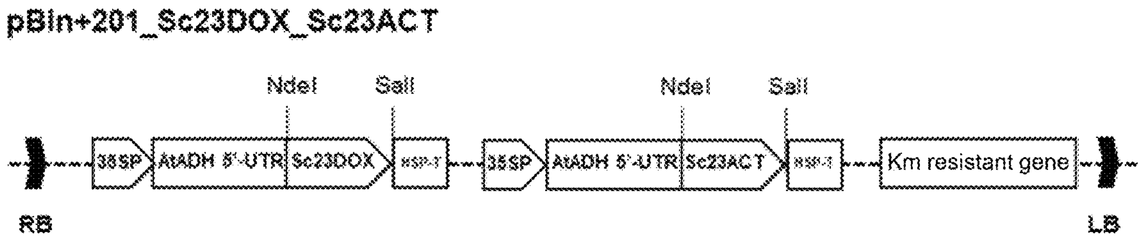

First, the Sc23DOX gene was linked to a pRI201 vector (manufactured by Takara Bio Inc.) to prepare a pRI201_Sc23DOX vector (see the upper part of FIG. 6). This was introduced into *Agrobacterium tumefaciens* EHA105 strain. The vector-containing *Agrobacterium tumefaciens* was cultured under shaking at 28° C. for 12 hours in YBS liquid culture medium [5 g/L beef extract, 1 g/L yeast extract, 5 g/L peptone, 5 g/L sucrose, 2 mM magnesium sulfate (pH 7.2)] containing 50 ppm kanamycin. After the culture solution (1.5 mL) was subjected to centrifugation at 10,000 rpm for 3 minutes to collect bacterial cells, the bacterial cells were suspended again in MS culture medium [Murashige & Skoog, see Physiol. Plant., 15, 473-497 (1962)] containing 1.5 mL of 3% sucrose. This was used as a bacterial liquid for infection.

The stems of the potato (*Solanum tuberosum*) variety "Sassy" cultivated in vitro, which had been cut into 3 to 5 mm pieces without joints, were used as a material for *Agrobacterium* infection. After being immersed in the above bacterial liquid of *Agrobacterium*, this was placed on sterilized filter paper to remove excessive *Agrobacterium*. This was placed on a plant hormone-containing MS culture medium (containing acetosyringone 100 μM, zeatin 2 ppm, indole-3-acetic acid 0.05 ppm, and agar 0.8%) in a petri dish, and was cultured for 3 days. The culture was performed at 25° C. for 16 hours under the condition: 16-hour illumination (photon flux density 32 HE/m2s)/8-hour non-illumination. Then, it was subcultured every two weeks in a culture medium containing 250 ppm of carbenicillin instead of acetosyringone. As a result, a redifferentiated individual was able to be obtained.

About 100 mg of a leaf of the obtained redifferentiated individual (#9) was frozen with liquid nitrogen, and was crushed with a mixer mill (1/30 sec, 2 min). Then, 300 μL of methanol was added to the crushed leaf, and the mixture was sonicated for 10 minutes. The resultant was subjected to centrifugal separation (15,000 rpm, 10 min), and the supernatant was collected. This extraction operation was repeated three times, the collected supernatant was dried under reduced pressure, and the residues were dissolved again in 200 μL of methanol. Then, 20 μL of re-dissolved solution was dissolved in 180 μL of methanol, and glycoalkaloid was analyzed through LC-MS (manufactured by Waters, product name: UPLC-ESI-MS ACQUITY). As the column, ACQUITY HSS T3 (1.8 μm φ2.1×100 mm) (manufactured by Waters) was used. In LC analysis, gradient elution was performed using a mobile phase (A: 0.1% formic acid water and B: acetonitrile). The gradient elution was performed under the condition: 0 to 30 minutes, 90% A/10% B to 45% A/55% B; 30 to 31 minutes, 45% A/55% B to 100% B; and maintaining for from 31 to 35 minutes, 100% B. The resultant was compared with a sample containing leptinine, which was a flower extract of *S. chacoense* PI 458310.

Figure 7:
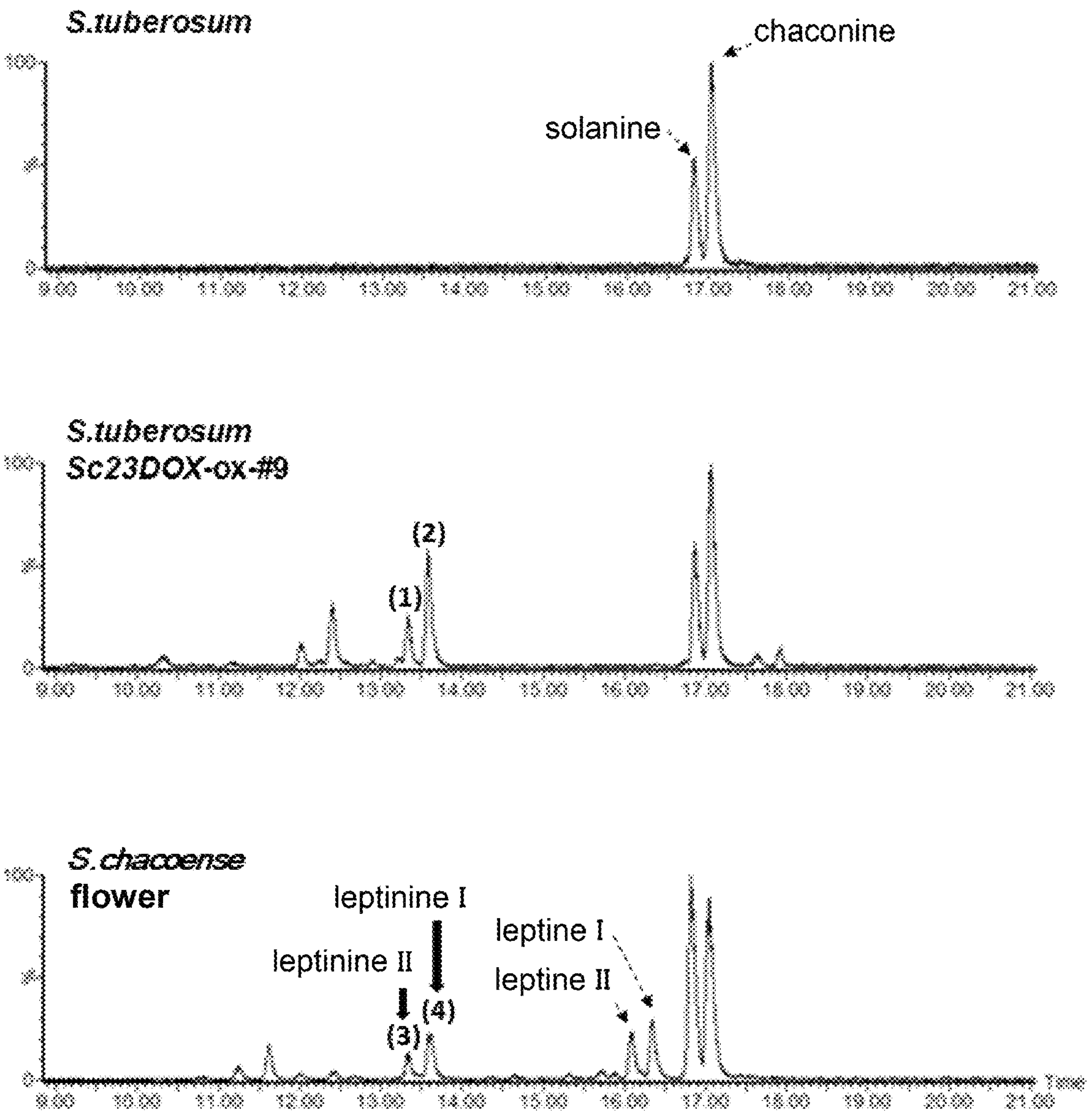
FIG. 7 is chart data of LC-MS showing the results of analyzing CPB-nonresistant potato (in the figure, "*S. tuberosum*"), potato that has expressed Sc23DOX (in the figure, "*S. tuberosum* Sc23DOX-ox-#9"), and the flower of CPB-resistant potato (in the figure, "the flower of *S. chacoense*")
Figure 8:
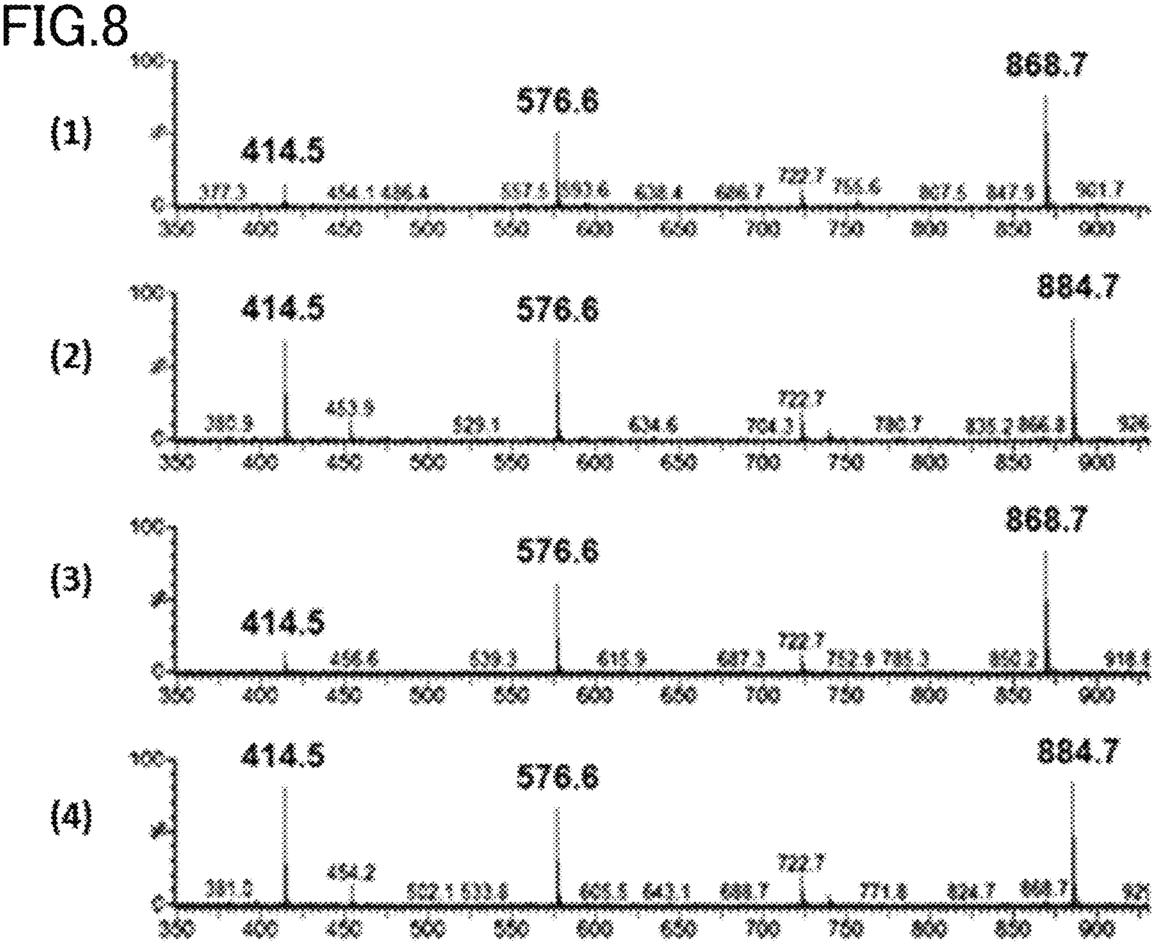
FIG. 8 is the mass spectra of the peaks (1) to (4) shown in FIG. 7.

As a result, as shown in FIG. 7 and FIG. 8, it was revealed that leptinine I and leptinine II can be produced by expression of Sc23DOX in *S. tuberosum* that has not been recognized to produce leptinine.

(Example 6) Analysis of Steroid Glycoalkaloid in Potato Hairy Roots to which 23DOX Gene and 23ACT Gene were Introduced Then, a transformed potato to which the 23DOX gene and the 23ACT gene derived from *S. chacoense* were introduced was created. Whether leptine I and leptine II were produced in this transformed body was examined in the following manner.

First, both the Sc23DOX gene and the Sc23ACT gene were linked to pBin+201 to produce a vector pBin+201_Sc23DOX Sc23ACT (see the lower part of FIG. 6), and this was introduced into *Agrobacterium Rhizogenes* C15834 strain. The vector-containing *Agrobacterium* was cultured under shaking at 28° C. for 12 hours in a 50 ppm kanamycin-containing YEB liquid culture medium [5 g/L beef extract, 1 g/L yeast extract, 5 g/L peptone, 5 g/L sucrose, 2 mM magnesium sulfate (pH 7.2)]. The culture solution was spread on YEB agar culture medium (2% agarose), and was cultured at 28° C. for 72 hours in a dark place. The potato variety "Sassy" cultured in vitro was cut into 1 to 1.5 cm pieces, and the tip of the root side of the stem was attached to the colony of *Rhizogenes*, and was stuck to B5 culture medium (containing 0.3% Gelrite and 2% sucrose) in a plant box so that the tip at the root side faced upward. This was cultured at 20° C. for 20 days in a dark place. The upper part of the stem in which formation of hairy roots had been confirmed was cut and was transferred to MS culture medium (containing 0.3% Gelrite, 2% sucrose, and 250 ppm Cefotaxime). The upper part of the stem was cultured at 25° C. for 7 days in a dark place and was sterilized. The tip (1 cm) of the grown hairy roots was cut, was transferred to B5 culture medium (containing 0.3% Gelrite, 2% sucrose, and 250 ppm Cefotaxime), and was cultured at 25° C. for 7 days in a dark place. The obtained hairy roots were cut into slices, the slices were transferred to B5 liquid culture medium (containing 2% sucrose), and were further cultured under shaking (100 rpm) at 20° C. for 14 days in a dark place. Then, 100 mg of products that proliferated from the slices were frozen with liquid nitrogen, and were crushed with a mixer mill (1/30 sec, 2 min). Then, 300 μL of methanol was added to the crushed products and the mixture was sonicated for 10 minutes. The mixture was subjected to centrifugal separation (15,000 rpm, 10 min), and the supernatant was collected. This extraction operation was repeated three times, the collected supernatant was dried under reduced pressure, and the residues were dissolved again in 200 μL of methanol. Then, 20 μL of the re-dissolved solution was dissolved in 180 μL of methanol, and glycoalkaloid was analyzed through LC-MS (manufactured by Waters, product name: UPLC-ESI-MS ACQUITY). As the column, ACQUITY BEH C-18 1.7 μm φ 2.1×100 mm (manufactured by Waters) was used. In LC analysis, gradient elution was performed using a mobile phase (A: 0.1% formic acid water and B: acetonitrile). The gradient elution was performed under the condition: maintaining for from 0 to 3 minutes, 90% A/10% B; 3 to 33 minutes, 90% A/10% B to 57.5% A/42.5% B; 33 to 38 minutes, 57.5% A/42.5% B to 0% A/100% B; and maintaining for from 38 to 43 minutes, 100% B. The resultant was compared with a sample containing leptine, which was a flower extract of *S. chacoense* PI 458310.

Figure 9:
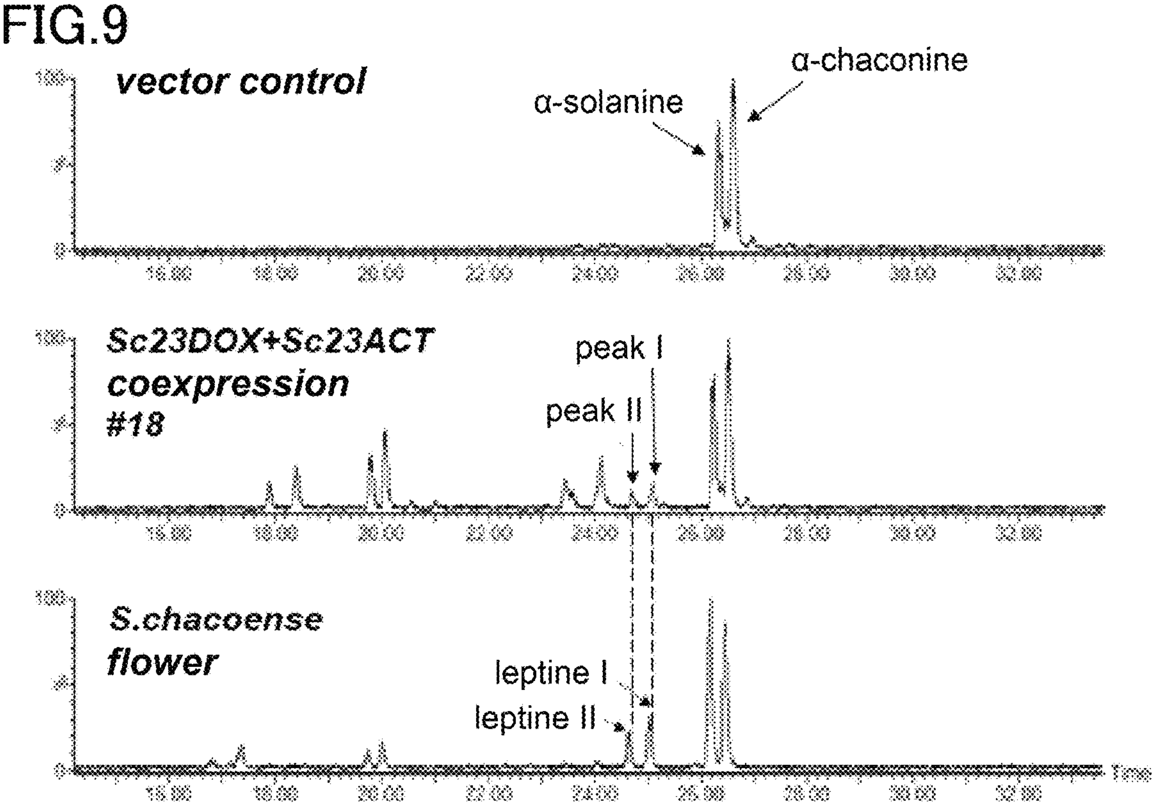
FIG. 9 is chart data of LC-MS showing the results of analyzing CPB-nonresistant potato (in the figure, "vector control") to which an empty vector is introduced, potato that has expressed Sc23DOX and Sc23ACT (in the figure, "Sc23DOX+Sc23ACT coexpression"), and the flower of CPB-resistant potato (in the figure, "the flower of "*S. chacoense*")
Figure 10:
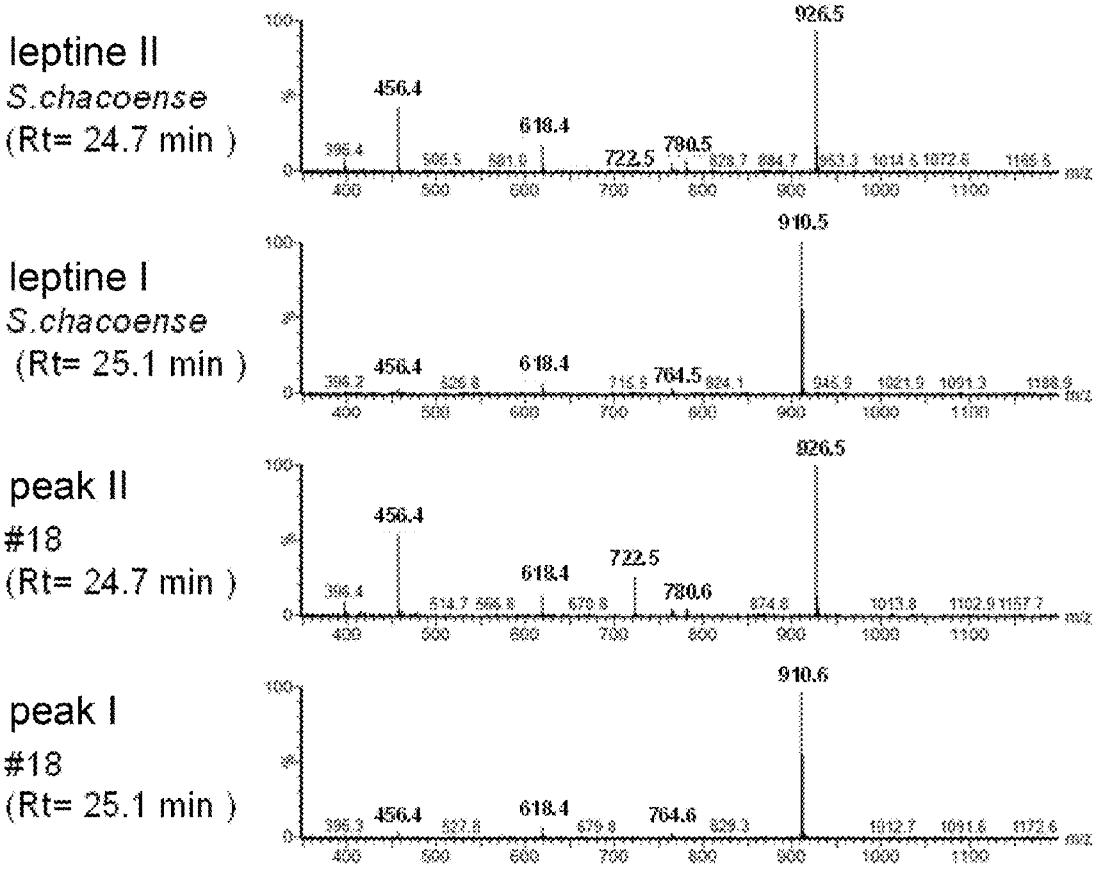
FIG. 10 is mass spectra of the peaks (peaks I and II, and leptines I and II) shown in FIG. 9.

As a result, as shown in FIG. 9 and FIG. 10, it was revealed that leptine I and leptine II can be produced by expression of Sc23DOX and Sc23ACT in *S. tuberosum* that has not been recognized to produce leptine.

As described above, it was revealed that, in *S. chacoense*, leptine is not produced from a compound (solanine, chaconine) having a solanidane skeleton as assumed previously, and leptine is produced by introducing a hydroxy group and then an acetoxy group to position 23 of a compound having a spirosolane skeleton, followed by converting the spirosolane skeleton of the compound into a solanidane skeleton.

(Example 7) Assay Regarding Presence or Absence of Sc23DOX Gene in Potato Varieties or Lines Used for Potato Breeding In order to confirm that *S. tuberosum* that does not exhibit resistance against CPB has no Sc23DOX gene, the following analysis was performed.

Figure 11:
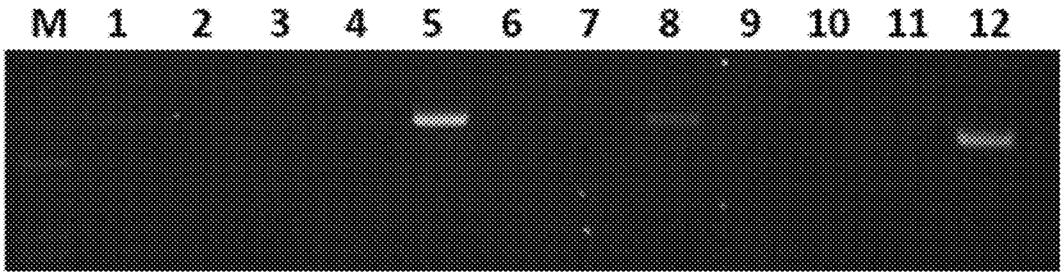
FIG. 11 is a photograph of gel electrophoresis, showing the results of the Sc23DOX gene detected through PCR by using, as a template, genome DNAs extracted from potato varieties exhibiting no resistance against CPB, lines used for potato breeding, and the wild species "*S. chacoense* PI 458310" that exhibits resistance against CPB. In the figure, "M" shows a 100 bp marker, "1" shows the analysis result of Irish Cobbler potato, "2" shows the result of May queen, "3" shows the analysis result of Sayaka, "4" shows the analysis result of Sassy, "5" shows the analysis result of Konafubuki, "6" shows the analysis result of Desiree, "7" shows the analysis result of 97H32-6, "8" shows the analysis result of Saikai 35, "9" shows the analysis result of Hokkai 87, "10" shows the analysis result of VTn 62-33-3, "11" shows the analysis result of W553-4, and "12" shows the analysis result of *S. chacoense* (PI 458310) (regarding the signs in the figure, the same is applied to FIG. 12)

From potato varieties that exhibit no resistance against CPB or lines used for potato breeding ("Irish Cobbler potato", "May queen", "Sayaka", "Sassy", "Konafubuki", "Desiree", "97H32-6", "Saikai 35", "Hokkai 87", "VTn 62-33-3", and "VTN 62-33-3") and a wild species that exhibits resistance against CPB ("*S. chacoense* PI 458310"), DNAs were extracted by the CTAB method (Hosaka and Hanneman Euphytica, 1998, 103: 265-271). For the extracted DNA, a primer GGCATCTACCAAATCAGTTAAAG (SEQ ID NO: 26) and a primer GTCTTGAAAACATCACTGGGAG (SEQ ID NO: 27) were used to perform PCR (35 cycles, manufactured by BioLine, using BIOTAQ) at an annealing temperature of 60° C., to amplify the gene. The obtained results were shown in FIG. 11.

As a result, about 1,700 bases of amplified fragments were found in *S. chacoense* PI 458310. In addition, amplified fragments were found even in Konafubuki and Saikai 35 that use *S. chacoense* in its breeding process. However, these amplified fragments were about 2,000 bases in size, which were larger than that of *S. chacoense* by about 200 bases. As a result of determining these base sequences, it was able to be confirmed that they have different sequences from that of the Sc23DOX gene (for this sequence, see Example 10).

Therefore, within the examined scope, one having the Sc23DOX gene was not detected in materials used in the aforementioned varieties or breeding in addition to a CPB-resistant potato, *S. chacoense* PI 458310.

(Example 8) Assay Regarding Presence or Absence of Sc23ACT Gene in Potato Varieties or Lines Used for Potato Breeding In order to confirm that *S. tuberosum* that does not exhibit resistance against CPB has no Sc23ACT gene, the following analysis was performed in the same manner as in Example 7.

Figure 12:
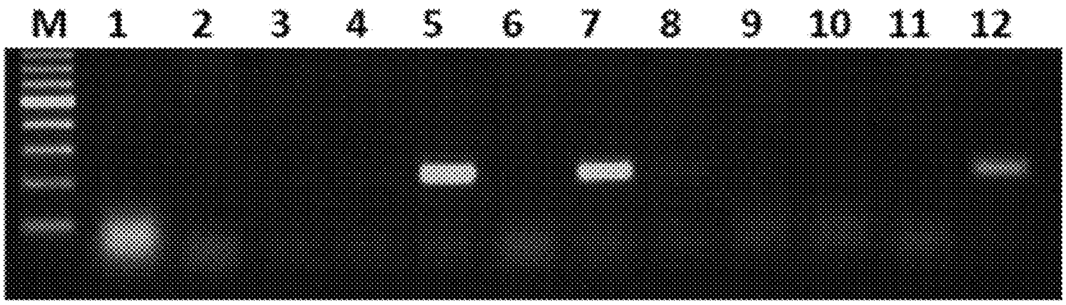
FIG. 12 shows the results of the Sc23ACT gene detected through PCR by using, as a template, genome DNAs extracted from potato varieties exhibiting no resistance against CPB, lines used for potato breeding, and the wild species "*S. chacoense* PI 458310" that exhibits resistance against CPB.

From potato varieties or lines used for potato breeding ("Irish Cobbler potato", "May queen", "Sayaka", "Sassy", "Konafubuki", "Desiree", "97H32-6", "Saikai 35", "Hokkai 87", "VTn 62-33-3", "W553-4", and "*S. chacoense* PI 458310"), DNAS were extracted by the CTAB method. For the extracted DNA, a primer GATTATGAATTTTACAATTTG (SEQ ID NO: 28) and a primer TACAGGTAGTGACAACGAGGATC (SEQ ID NO: 29) were used to perform PCR (40 cycles, manufactured by BioLine, using BIOTAQ) at an annealing temperature of 60° C., to amplify the gene. The obtained results were shown in FIG. 12.

As a result, it was surprisingly revealed that Konafubuki, 97H32-6, and Saikai 35 that exhibit no resistance against CPB also have the Sc23ACT gene. Konafubuki, 97H32-6, and Saikai 35 use *S. chacoense* (W84 and chc525-3) in its breeding process (Asama et al., Bulletin of the Hokkaido Prefectural Agricultural Experiment Station, 1982, 48: 75-84, Phumichai et al., Genome, 2005, 48: 977-984). There is no report that W84 and chc525-3 accumulate leptine. However, these potatoes can be expected to exhibit an ability to generate leptine by introducing the Sc23DOX gene to Konafubuki and 97H32-6, which has been shown to have the Sc23ACT gene.

Therefore, it was found that detection of the Sc23ACT gene can easily reveal materials that potentially have such an ability to generate leptine SAKURAFUBUKI and pearlstarch, which use Konafubuki in the breeding process, were also analyzed. As a result, it was revealed that these potatoes have Sc23ACT (not illustrated in the figures).

(Example 9) Analysis of Steroid Glycoalkaloid and Genes in Progeny Obtained by Crossing *S. chacoense* with Potato In order to confirm that the Sc23DOX gene and the Sc23ACT gene correlate with accumulation of leptine, the following analysis was performed.

First, five lines of seedling were obtained from *S. chacoense* PI 458310 expressing leptine. It was confirmed that all of them accumulated leptine.

Figure 13:
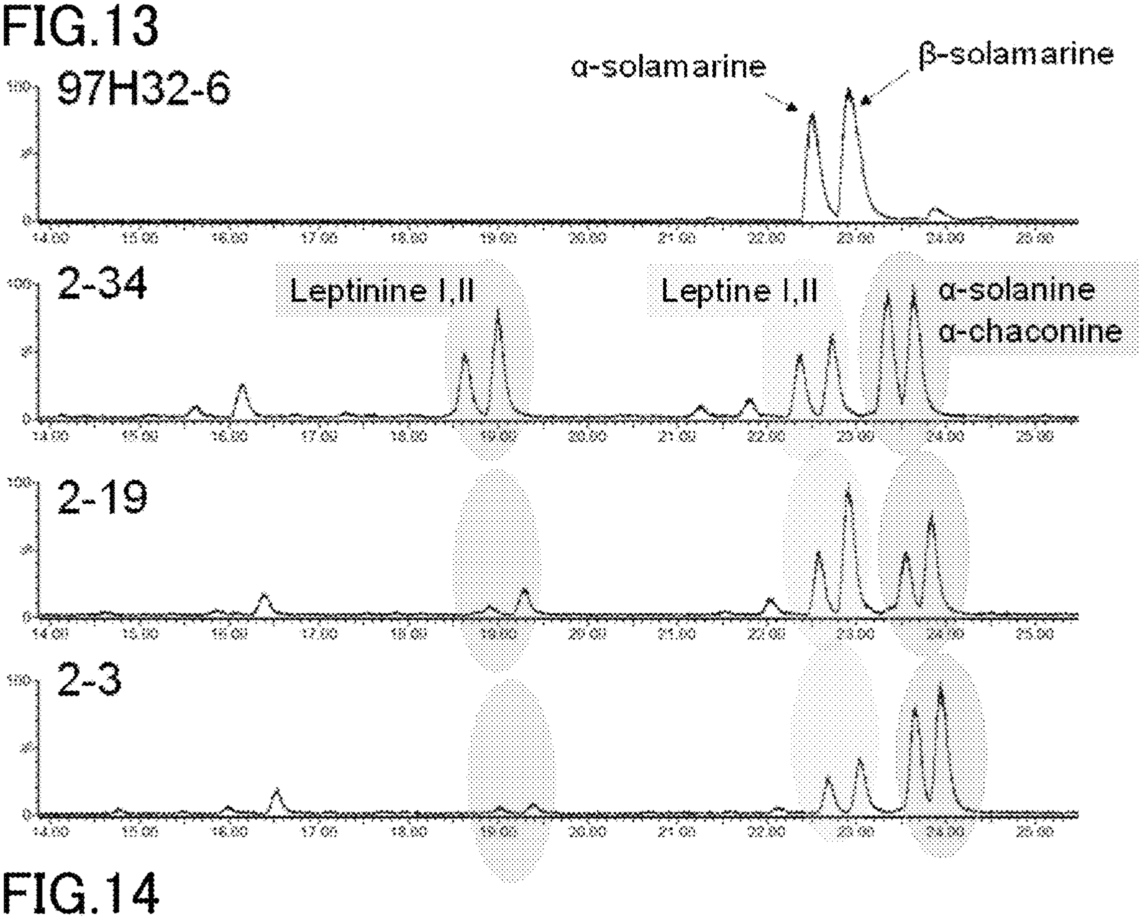
FIG. 13 is chart data of LC-MS showing the results of analyzing steroid glycoalkaloids in hybrids, which are obtained by crossing seedlings three lines obtained from *S. chacoense* PI 458310 that has expressed leptine, with the potato line 97H32-6 that has expressed no leptine. In the figure, "97H32-6" shows the result of analyzing 97H32-6, and "2-34", "2-19", and "2-3" show the results of analyzing hybrids PI 458310-2×97H32-6 34, PI 458310-2×97H32-6 19, and PI 458310-2×97H32-6 3 shown in Table 1.

Next, the five lines, and a potato line 97H32-6 expressing no leptine were crossbred to obtain a hybrid seed. Then, from leaves of 263 individuals obtained by growing the hybrid seeds, DNA was extracted by the method of Hattori et al. (Breed. Sci. 57: 305-314), and the Sc23DOX gene and the Sc23ACT gene were each amplified by the methods described in Examples 7 and 8. From about 100 mg of leaves obtained by growing the hybrid seeds, each steroid glycoalkaloid was analyzed by the method described in Example 3. The obtained results are shown in Table 1. The LC-MS analysis data of three lines are shown in FIG. 13.

TABLE 1

| Line numbers | Detection of leptine |
|---|---|
| PI 458310-2 × 97H32-6 3 | Detected |
| PI 458310-2 × 97H32-6 19 | Detected |

TABLE 1-continued

| Line numbers | Detection of leptine |
|---|---|
| PI 458310-2 × 97H32-6 32 | Detected |
| PI 458310-2 × 97H32-6 34 | Detected |
| PI 458310-2 × 97H32-6 44 | Detected |
| PI 458310-2 × 97H32-6 57 | Detected |
| PI 458310-2 × 97H32-6 62 | Detected |
| PI 458310-2 × 97H32-6 67 | Detected |
| PI 458310-2 × 97H32-6 98 | Detected |
| PI 458310-2 × 97H32-6 113 | Detected |
| PI 458310-3 × 97H32-6 2 | Detected |
| PI 458310-3 × 97H32-6 17 | Detected |
| PI 458310-3 × 97H32-6 19 | Detected |
| PI 458310-3 × 97H32-6 22 | Detected |
| PI 458310-3 × 97H32-6 37 | Detected |
| PI 458310-6 × 97H32-6 3 | Detected |
| PI 458310-6 × 97H32-6 4 | Detected |
| PI 458310-6 × 97H32-6 17 | Detected |
| PI 458310-6 × 97H32-6 26 | Detected |
| PI 458310-6 × 97H32-6 36 | Detected |

As a result, all of the hybrid individuals were found to have the Sc23DOX gene and the Sc23ACT gene. This revealed that the seedling individual of *S. chacoense* PI 458310 homozygously has the Sc23DOX gene, and that the seedling individual of *S. chacoense* PI 458310, the potato line 97H32-6, or both homozygously have the Sc23ACT gene.

As shown in Table 1, all of the hybrid individuals were found to accumulate leptine. Therefore, it was confirmed that presence of the Sc23DOX gene and the Sc23ACT gene correlates with accumulation of leptine.

Moreover, 97H32-6 can be backcrossed with the line obtained in the above manner, which has the Sc23DOX gene and the Sc23ACT gene and produces leptine, to obtain a hybrid seed. A hybrid seed that produces leptine can be determined by analysis of presence or absence of these genes in the same manner as the above.

(Example 10) Verification of 23DOX Gene in *S. tuberosum*

In tblast analysis targeted for the sequences in the potato (*S. tuberosum*) genome database (Spud DB: http://solanaceae.plantbiology.msu.edu/index.shtml), even the sequence (PGSC0003DMT400081914) having the highest homology to Sc23DOX has a low identity of 79%, and it has been believed that no 23DOX gene exists in *S. tuberosum.*

Surprisingly, however, as shown in Example 7, amplification of a fragment of about 2,000 bases, which was about 200 bases larger than the amplification product (about 1, 700 bases) derived from the Sc23DOX gene of *S. chacoense* PI 458310, was found in *S. tuberosum*. As a result of determining the base sequences, it was revealed that the sequence extremely close to the Sc23DOX gene was amplified.

For the cDNA of *S. tuberosum* variety, Sassy, a primer CACCATGGCATCTACCAAATCAGTTAAAG (SEQ ID NO: 30) and a primer TCAAACACCGCAATAAGTCTTGAAA (SEQ ID NO: 31) were used to perform PCR (40 cycles, manufactured by Takara Bio Inc., using PrimeSTAR) at an annealing temperature of 55° C. The obtained PCR amplification product was cloned into a pENTR/D-TOPO vector (manufactured by Thermo Fisher Scientific), to obtain a gene fragment, followed by determining the full-length sequence (the amino acid sequence encoded by the determined nucleotide sequence is shown in SEQ ID NO: 4. The protein encoded by this gene is also referred to as "St23DOX" hereinafter.). Note that, St23DOX and Sc23DOX had a sequence identity of 94% in terms of an amino acid level. As a result of further analysis, it was fond that at least Konafubuki, SAKURAFUBUKI, pearlstarch, Saikai 35, and Irish Cobbler potato in addition to Sassy also have the St23DOX gene.

(Example 11) Detection of In Vitro Enzyme Activity of St23DOX

The St23DOX gene identified in Example 10 was analyzed in the same method described in Example 3. As a result, as shown in FIGS. 2 and 3, it was revealed that, a product to which a hydroxy group was introduced at position 23 can be obtained even in those derived from *S. tuberosum* (St23DOX) when α-tomatine was a substrate. That is, it was revealed that St23DOX can be involved with production of leptinines similarly with Sc23DOX and S123DOX. On the other hand, in *S. tuberosum* (variety: Sassy), the resistance against CPB via production of leptinine is not observed. Therefore, the above suggests that St23DOX is not expressed enough to contribute to production of leptinine at least in variety Sassy.

(Example 12) Verification of 23ACT Gene in *S. tuberosum*

In tblast analysis targeted for the sequences in the potato (*S. tuberosum*) genome database (Spud DB: http://solanaceae.plantbiology.msu.edu/index.shtml), even the sequence (PGSC0003DMT400023800) having the highest homology to Sc23ACT has a low identity of 75%, and it has been confirmed that excessive 30 amino acids were added to the N-terminal. Therefore, it was believed that one exceeding a same homology of 50% was not found in one having the full length similar to that of Sc23ACT, and no 23ACT gene exists in *S. tuberosum.*

Surprisingly, however, it was suggested that the sequence extremely close to the Sc23ACT gene was found also in *S. tuberosum* when the assay primer was prepared in Example 8. For the genome of the variety Sassy, a primer CATATGGCAGCATCAAGTTGTGT (SEQ ID NO: 32) and a primer GTCGACTTAATTAAGATTAGTAATTGGAGAAG (SEQ ID NO: 33) were used to perform PCR (40 cycles, manufactured by Takara Bio Inc., using PrimeSTAR HS) at an annealing temperature of 55° C. The obtained PCR amplification product was cloned into a pCR4Blunt-TOPO vector (manufactured by Thermo Fisher Scientific), to obtain a gene fragment, followed by determining the full-length sequence (the amino acid sequence encoded by the determined nucleotide sequence is shown in SEQ ID NO: 10. The protein encoded by this gene is also referred to as "St23ACT".). Note that, St23ACT and Sc23ACT had a sequence identity of 91% in terms of an amino acid level.

(Example 13) Detection of In Vitro Enzyme Activity of St23ACT

The St23ACT gene identified in Example 12 was analyzed in the same method described in Example 4. As a result, as shown in FIG. 4 and FIG. 5, it was revealed that a product to which an acetoxy group was introduced at position 23 was obtained in the presence of St23ACT when 23 hydroxy tomatine was a substrate. That is, it was revealed that St23ACT can be involved with production of leptines similarly with Sc23ACT and S123ACT. On the other hand, in *S. tuberosum* (variety: Sassy), the resistance against CPB via accumulation of leptine is not observed. Therefore, the above suggests that St23ACT is not expressed enough to contribute to production of leptine, at least in variety Sassy, similarly with the above St23DOX.

(Example 14) Introduction of Sc23DOX Gene to Konafubuki Having Sc23ACT Gene

It was revealed in Example 8 that Konafubuki has the sequence of Sc23ACT. In order to confirm that this sequence functions and Konafubuki expresses 23ACT activity, steroid glycoalkaloid in potato hairy roots of Konafubuki, to which the Sc23DOX gene had been introduced, was analyzed.

Figure 14:
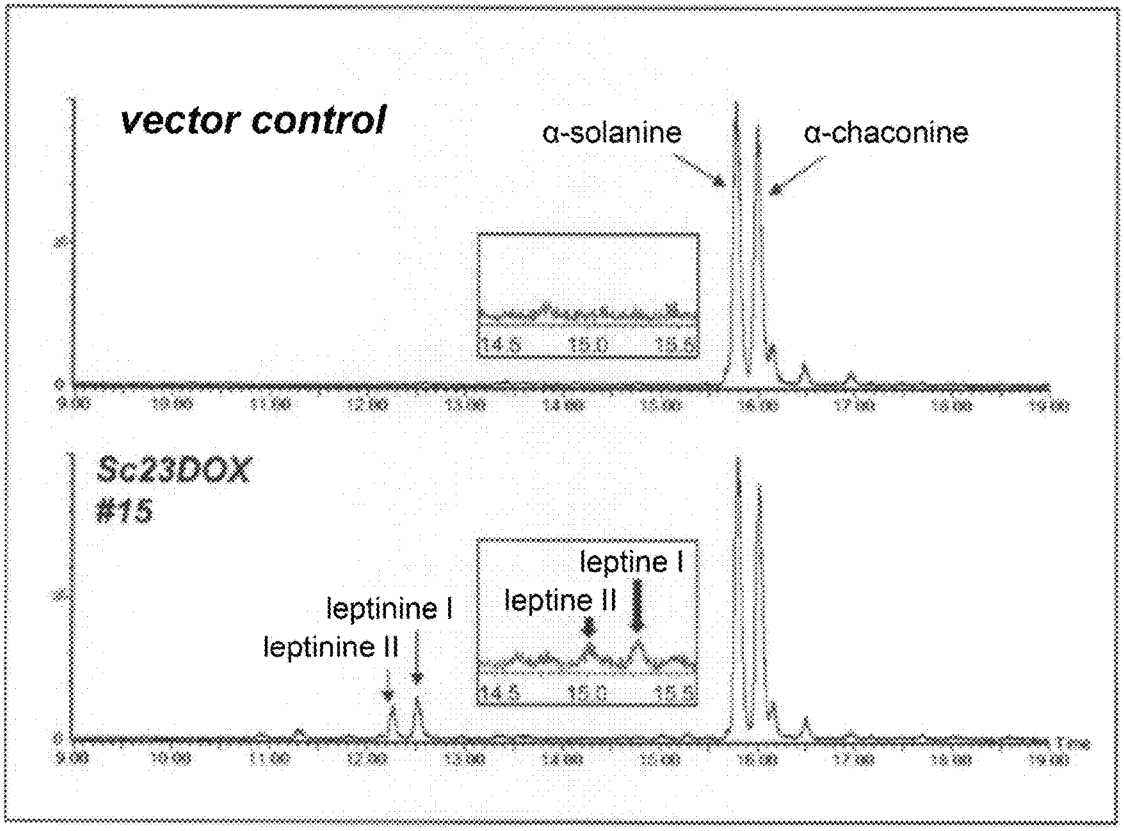
FIG. 14 is chart data of LC-MS showing the results of analyzing a CPB-nonresistant potato variety Konafubuki (in the figure, "vector control") to which an empty vector is introduced and Konafubuki (in the figure, "Sc23DOX #15") that has expressed Sc23DOX. In the enclosing line in the figure, the chart data at the retention time of from 14.5 minutes to 15.5 minutes are enlarged.
Figure 15:
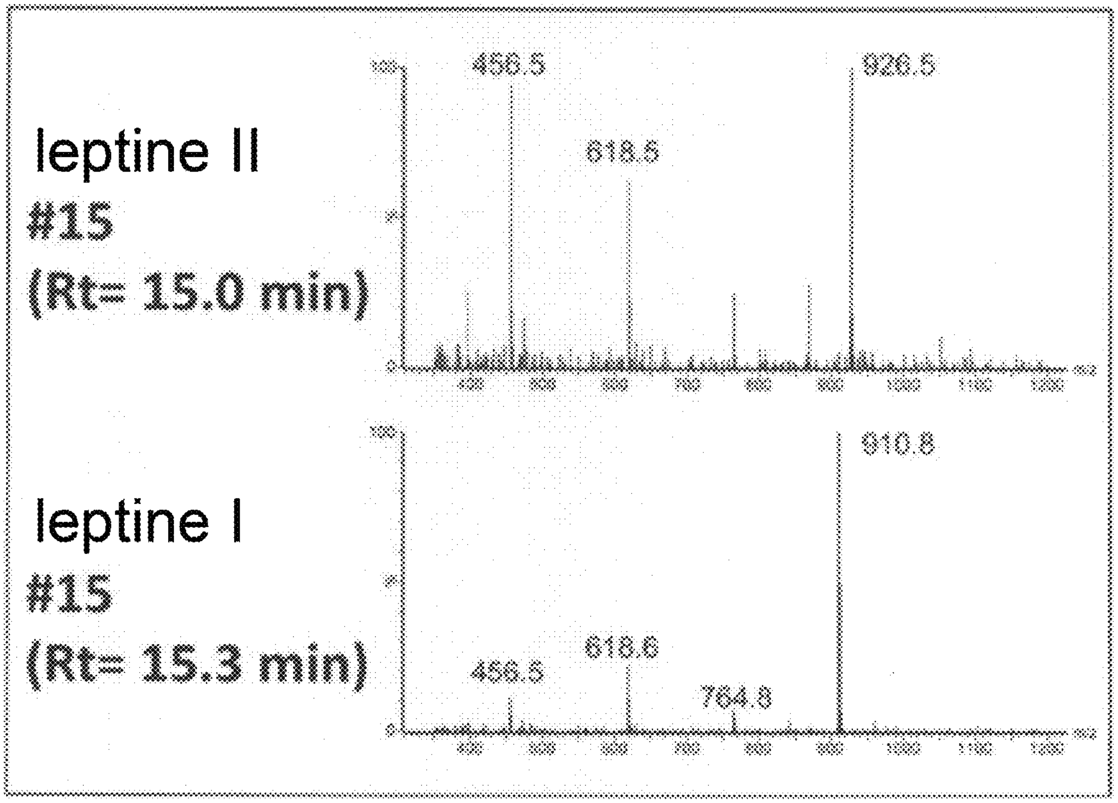
FIG. 15 is mass spectra of the peaks (leptines I and II) shown in FIG. 14.

Specifically, in the same manner as in Example 6, the Sc23DOX gene was linked to pBin+201 to prepare a vector pBin+201_Sc23DOX. This was introduced to *Agrobacterium Rhizogenes* C15834 strain. The vector-containing *Agrobacterium* was cultured under shaking at 28° C. for 12 hours in YEB liquid culture medium [5 g/L beef extract, 1 g/L yeast extract, 5 g/L peptone, 5 g/L sucrose, 2 mM magnesium sulfate (pH 7.2)] containing 50 ppm kanamycin. The culture solution was spread on YEB agar culture medium (2% agarose), and was cultured at 28° C. for 72 hours in a dark place. The potato variety "Konafubuki" cultured in vitro was cut into 1 to 1.5 cm pieces, and the tip of the root side of the stem was attached to the colony of *Rhizogenes*, and was stuck to B5 culture medium (containing 0.3% Gelrite and 2% sucrose) in a plant box so that the tip of the root side faced upward. This was cultured at 20° C. for 20 days in a dark place. The upper part of the stem in which formation of hairy roots had been confirmed was cut and was transferred to MS culture medium (containing 0.3% Gelrite, 2% sucrose, and 250 ppm Cefotaxime). The upper part of the stem was cultured at 25° C. for 7 days in a dark place and was sterilized. The tip (1 cm) of the grown hairy roots was cut, was transferred to B5 culture medium (containing 0.3% Gelrite, 2% sucrose, and 250 ppm Cefotaxime), and was cultured at 25° C. for 7 days in a dark place. The obtained hairy roots were cut into slices, the slices were transferred to B5 liquid culture medium (containing 2% sucrose), and were further cultured under shaking (100 rpm) at 20° C. for 14 days in a dark place. Then, 100 mg of products that proliferated from the slices were frozen with liquid nitrogen, and were crushed with a mixer mill (1/30 sec, 2 min). Then, 300 μL of methanol was added to the crushed products and the mixture was sonicated for 10 minutes. The mixture was subjected to centrifugal separation (15,000 rpm, 10 min), and the supernatant was collected. This extraction operation was repeated three times, the collected supernatant was dried under reduced pressure, and the residues were dissolved again in 200 μL of methanol. Then, 20 μL of the re-dissolved solution was dissolved in 180 μL of methanol, and glycoalkaloid was analyzed through LC-MS (manufactured by Waters, product name: UPLC-ESI-MS ACQUITY). As the column, ACQUITY HSS T3 (1.8 μm φ2.1×100 mm) (manufactured by Waters) was used. In LC analysis, gradient elution was performed using a mobile phase (A: 0.1% formic acid water and B: acetonitrile). The gradient elution was performed under the condition: 0 to 30 minutes, 90% A/10% B to 45.00 A/55.0% B; 30 to 31 minutes, 45.0% A/55.0% B to 0% A/100% B; and maintaining for from 31 to 35 minutes, 100% B. As a result, as shown in FIGS. 14 and 15, it was confirmed that leptine I and leptine II can be produced by compulsively expressing only the Sc23DOX gene in Konafubuki that had not been recognized to produce leptine.

As described above, it was suggested that lines and varieties having the Sc23ACT gene can produce leptine by introducing only the Sc23DOX gene.

Figure 16A:
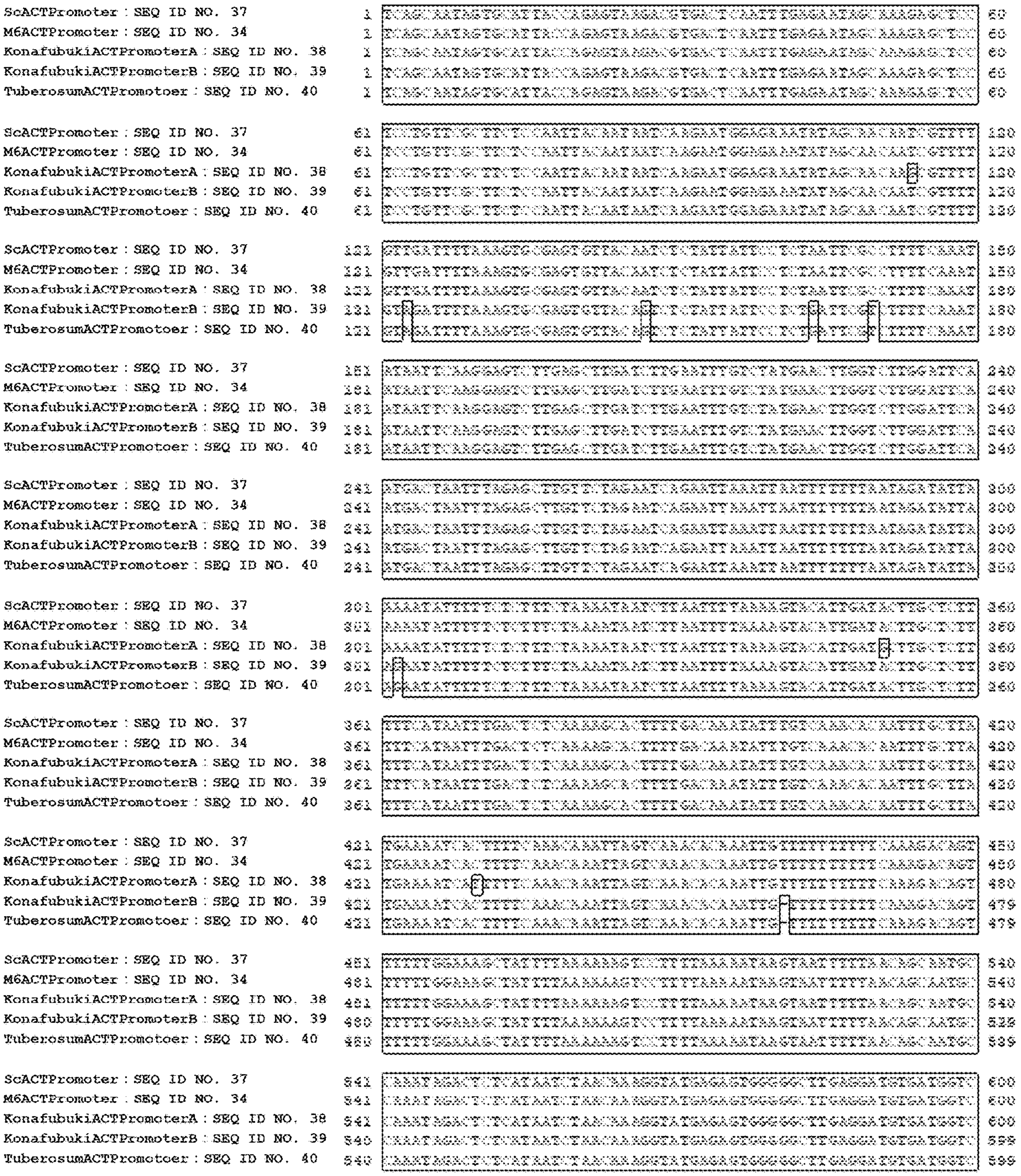
FIG. 16A shows comparison of the sequences of about 1.7 kb promoter regions of the 23ACT genes of *S. chacoense* PI 458310, *S. chacoense* M6, Konafubuki, and Sassy, with each of the sequences stretched just before the start codon being described (part 1)
Figure 16B:
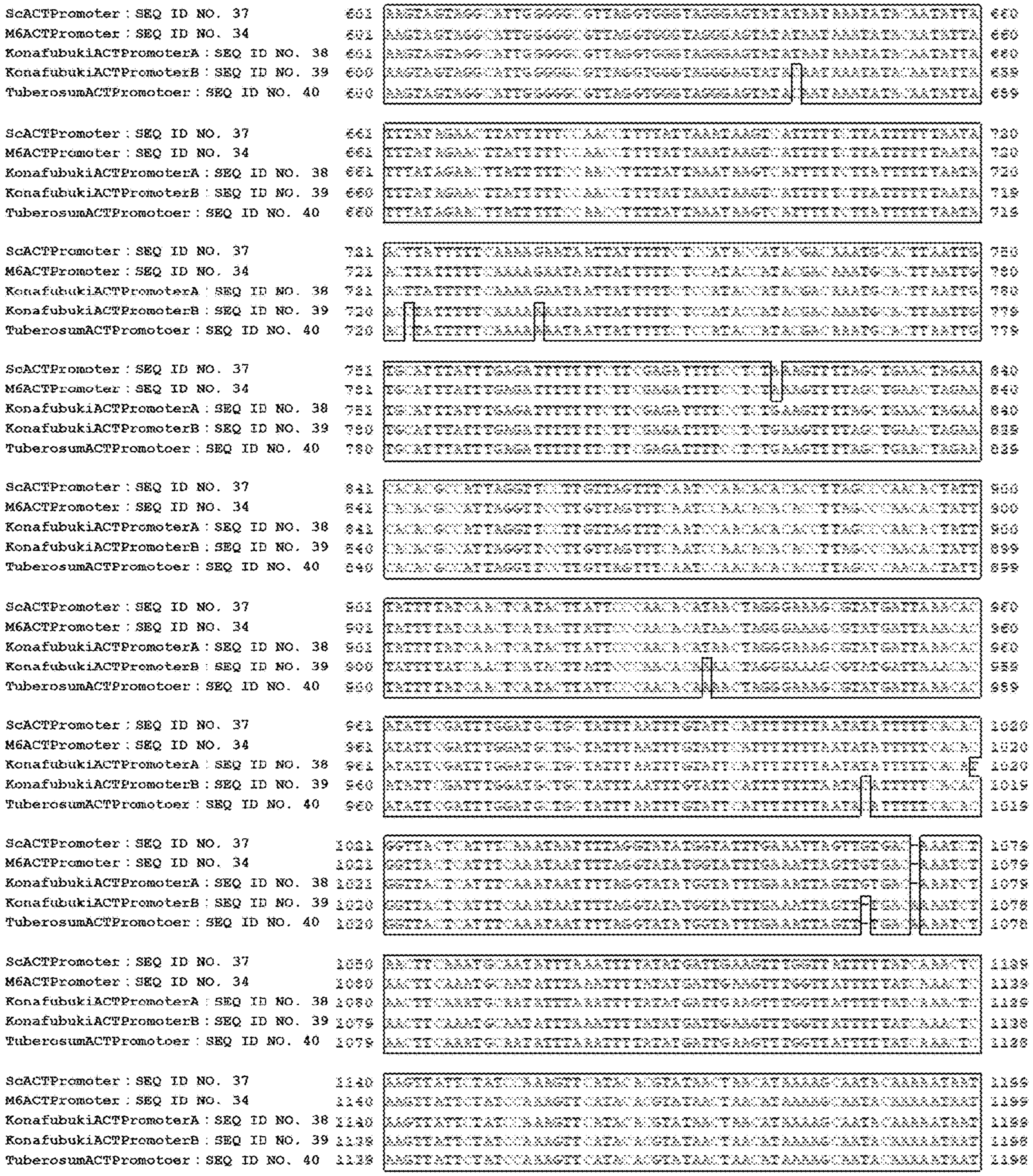
FIG. 16B shows comparison of the sequences of about 1.7 kb promoter regions of the 23ACT genes of *S. chacoense* PI 458310, *S. chacoense* M6, Konafubuki, and Sassy, with each of the sequences stretched just before the start codon being described (part 2)
Figure 16C:
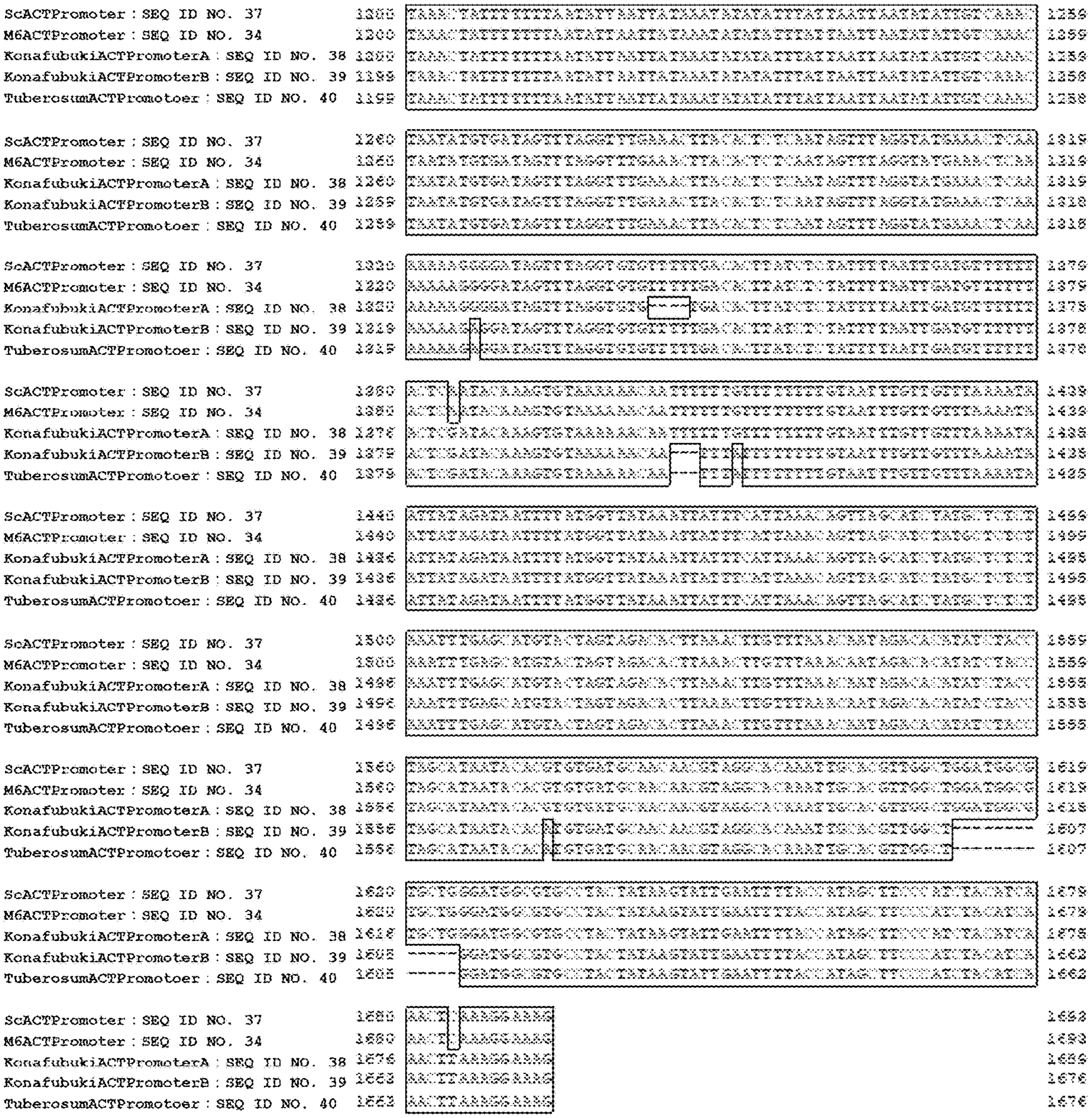
FIG. 16C shows comparison of the sequences of about 1.7 kb promoter regions of the 23ACT genes of *S. chacoense* PI 458310, *S. chacoense* M6, Konafubuki, and Sassy, with each of the sequences stretched just before the start codon being described (part 3)
Figure 17A:
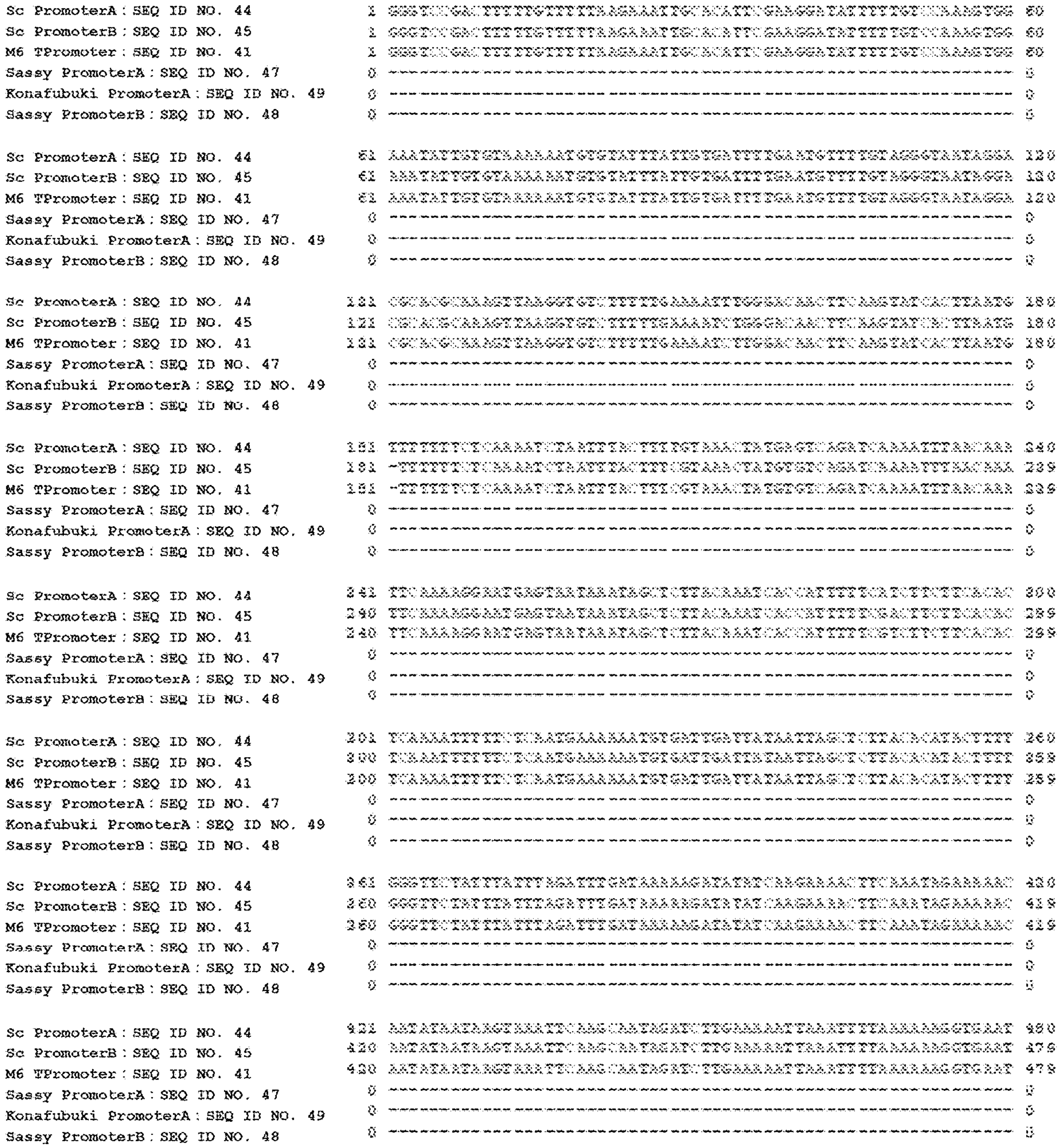
FIG. 17A shows comparison of the sequences of about 1 to 1.5 kb promoter regions of the 23DOX genes of *S. chacoense* PI 458310, *S. chacoense* M6, Konafubuki, and Sassy, with each of the sequences stretched just before the start codon being described (part 1)
Figure 17B:
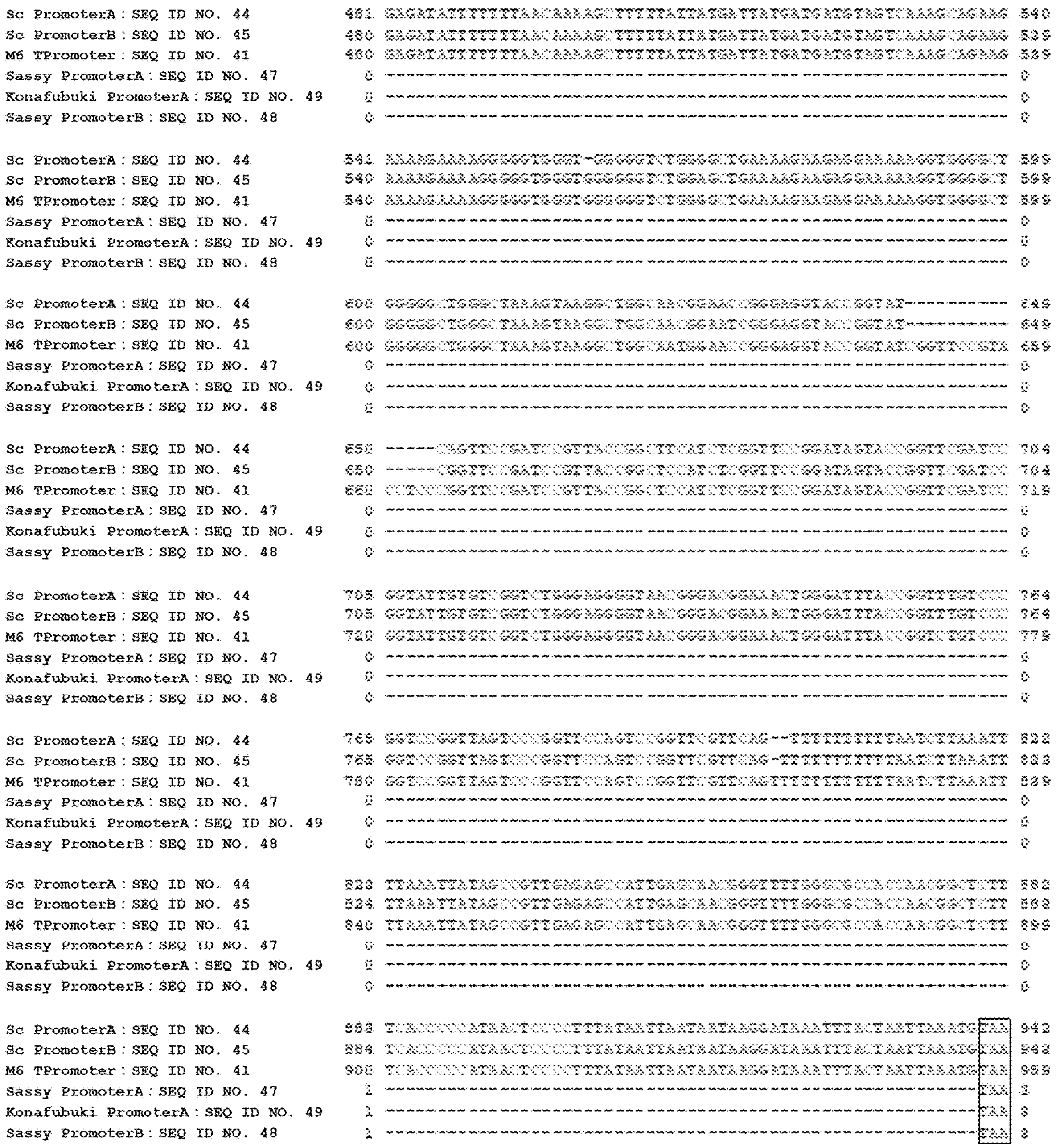
FIG. 17B shows comparison of the sequences of about 1 to 1.5 kb promoter regions of the 23DOX genes of *S. chacoense* PI 458310, *S. chacoense* M6, Konafubuki, and Sassy, with each of the sequences stretched just before the start codon being described (part 2)
Figure 17C:
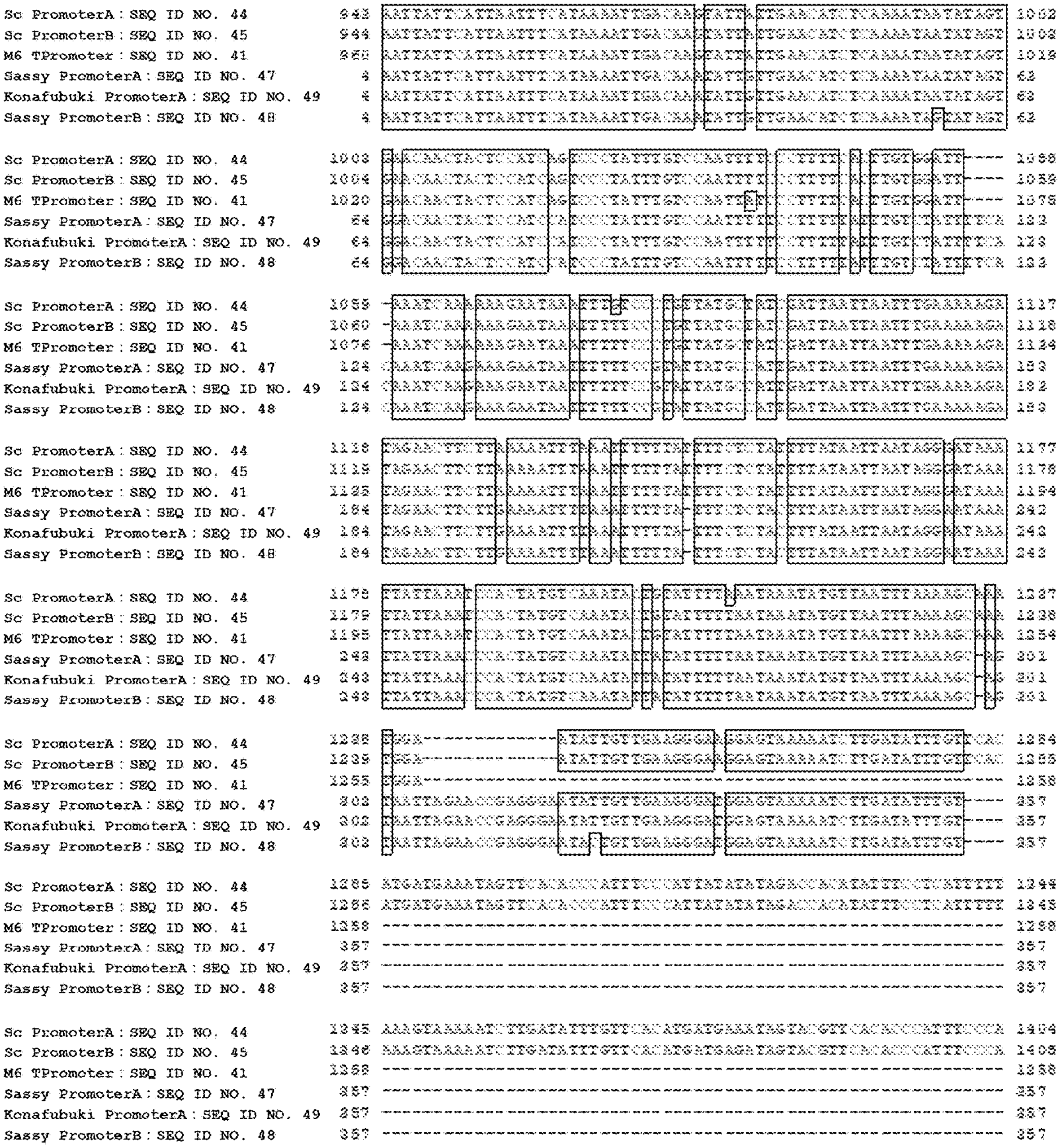
FIG. 17C shows comparison of the sequences of about 1 to 1.5 kb promoter regions of the 23DOX genes of *S. chacoense* PI 458310, *S. chacoense* M6, Konafubuki, and Sassy, with each of the sequences stretched just before the start codon being described (part 3)
Figure 17E:
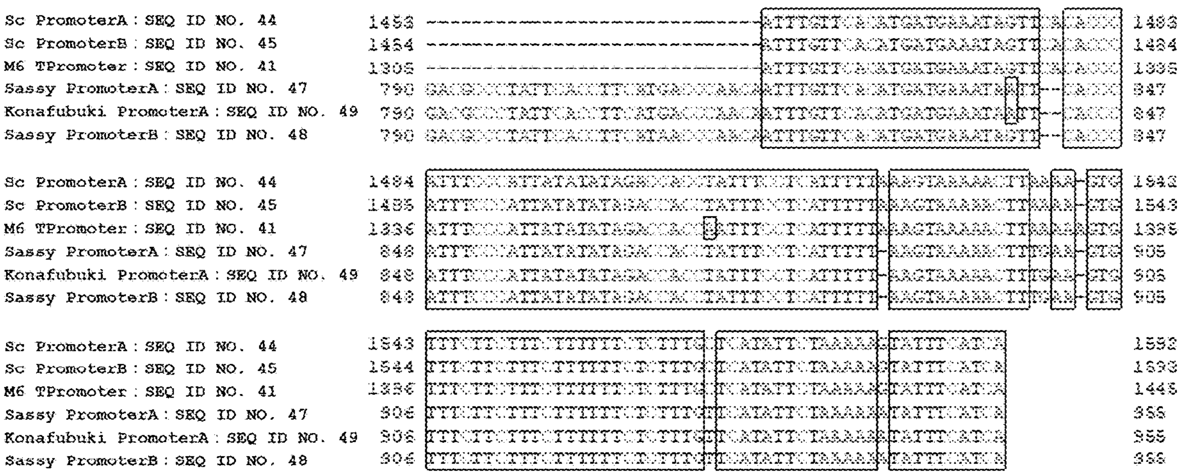
FIG. 17E shows comparison of the sequences of about 1 to 1.5 kb promoter regions of the 23DOX genes of *S. chacoense* PI 458310, *S. chacoense* M6, Konafubuki, and Sassy, with each of the sequences stretched just before the start codon being described (part 5).

(Example 15) Acquisition of Gene Sequences of Promotor of 23ACT Gene Having Functions and Promotor of 23ACT Gene Having No Function SRX118622: transcriptome analysis of breaker fruit of *Solanum lycopersicon* cv Heinz registered in NCBI data base was used to analyze expression of the S123ACT gene, and Trinity (https://github.com/trinityrnaseq/trinityrnaseq/wiki), Bowtie (http://bowtie-bio.sourceforge.net/index.shtml), DEGseq (Original site), and express (Original site) were used to analyze the gene expression level (fpkm: fragments per kilobase of exon per million reads mapped). As a result, the calculated gene expression level was found to be 70.93. Because esculeoside A is synthesized in the breaker fruit stage of tomato, a sufficient level of the gene 23ACT is found to be expressed. *Solanum chacoense* M6 (Leisner et al., Plant Journal (2018) 94, 562-570) is the line that produces no leptine. However, as a result of homology search of the published gene information, the 23ACT gene was found to be g38106. Moreover, it was found that the promoter sequence of Sc23ACT in *Solanum chacoense* M6 can function because the described gene expression level in a leaf was 63.11. The genome sequence on which g38106 was located was found to be scaffold_1344 from Table S5, and an effective sequence (SEQ ID NO: 34) as a promotor was obtained. Based on this sequence and the sequences of g38106 and St23ACT, using primers U1240 (TCAGCAATAGTGCATTACCAGAG) (SEQ ID NO: 35) and U1241 (CGCCTAAGTGAAGAAGGGGTA) (SEQ ID NO: 36), one sequence (SEQ ID NO: 37) was obtained from *S. chacoense* PI 458310, two sequences (A: SEQ ID NO: 38 and B: SEQ ID NO: 39) were obtained from Konafubuki, and one sequence (SEQ ID NO: 40) was obtained from Sassy. The sequence B of Konafubuki and the sequence of Sassy are completely identical to each other, and are found to have no activity. On the other hand, *Solanum chacoense* M6 and the sequence A of Konafubuki have activity. The results obtained by comparing these sequences are shown in FIG. 16A to FIG. 16C. By comparing these sequences, it is possible to change a generally inactive type to the St23ACT active type by substituting an inactive sequence with an active sequence through a method such as gene recombination, genome editing, or the like.

(Example 16) Acquisition of Gene Sequences of Promotor of 23DOX Gene Having Functions and Promotor of 23DOX Gene Having No Function SRX118622: transcriptome analysis of breaker fruit of *Solanum lycopersicon* cv Heinz registered in NCBI data base was used to analyze expression of the S123DOX gene, and Trinity (https://github.com/trinityrnaseq/trinityrnaseq/wiki), Bowtie (http://bowtie-bio.sourceforge.net/index.shtml), DEGseq (Original site), and express (Original site) were used to analyze the gene expression level (fpkm: fragments per kilobase of exon per million reads mapped). As a result, the calculated gene expression level was found to be 1982.30. Because esculeoside A is synthesized in the breaker fruit stage of tomato, a sufficient amount of the gene 23DOX is found to be expressed. *Solanum chacoense* M6 (Leisner et al., Plant Journal (2018) 94, 562-570) is a line that produces no leptine. However, as a result of homology search of the published gene information, the 23DOX gene was found to be g39095. Moreover, it was found that the promoter sequence of Sc23DOX in *Solanum chacoense* M6 does not function because the described gene expression level in a leaf was 2.25. The genome sequence on which g39095 was located was found to be scaffold 1570 from Table S5, and the sequence (SEQ ID NO: 41) that does not function as a promoter was obtained. Based on this sequence and the sequences of g39095 and St23DOX, using primers U1249 (GGGTCCGACTTTTTGTTTTT) (SEQ ID NO: 42) and U1243 (CAATGGCAATTGTGGAATCA) (SEQ ID NO: 43), two functional sequences (A: SEQ ID NO: 44 and B: SEQ ID NO: 45) were obtained from *S. chacoense* PI 458310. However, since no functional sequence was obtained from Sassy or Konafubuki, primers U1276 (TAAAATTATTCATTAATTTCATAAAATTGACA) (SEQ ID NO: 46) and U1243 were used to obtain two sequences (A: SEQ ID NO: 47 and B: SEQ ID NO: 48) from Sassy, and the sequence (SEQ ID NO: 49) from Konafubuki, which is identical to the sequence A of Sassy and has no activity. The results obtained by comparing these sequences are shown in FIG. 17A to FIG. 17E. By comparing these sequences, it is possible to change a generally inactive type to the St23DOX active type by substituting an inactive sequence with an active sequence through a method such as gene recombination, genome editing, or the like.

INDUSTRIAL APPLICABILITY

As described above, according to the present invention, use of the identified hydroxylase gene and/or acetyltransferase gene can introduce a hydroxy group or an acetoxy group into position 23 of a spirosolane skeleton, and can produce leptinine or leptine. Moreover, according to the present invention, biosynthesis and accumulation of leptine can also increase, for example, resistance against CPB in plants. That is, plants having increased resistance against CPB can be efficiently provided. According to the present invention, it is possible to efficiently determine, for example, resistance against CPB in plants by using an indicator, for example, the presence of the gene. Therefore, the present invention is effective in cultivating, for example, solanaceous plants that experience insect damage by CPB.

The invention claimed is:

1. A transformed cell that is capable of regenerating *Solanum tuberosum* having increased resistance against Colorado potato beetle, the transformed cell comprising:

(a) DNA encoding a protein that consists of an amino acid sequence as set forth in SEQ ID NO: 2, 4, or 6; and (b) DNA encoding a protein that consists of an amino acid sequence as set forth in SEQ ID NO: 8, 10, or 12.

2. A transformed *Solanum tuberosum* plant having increased resistance to Colorado potato beetle, which is regenerated from the transformed cell according to claim 1.

3. A method for producing a *Solanum tuberosum* plant having Colorado potato beetle resistance, the method comprising:

introducing, to a cell, at least one DNA selected from the group consisting of (a) to (b) below and at least one DNA selected from the group consisting of (c) to (d) below; and regenerating a *Solanum tuberosum* plant from a transformed cell to which the DNA selected from (a) to (b) and the DNA selected from (c) to (d) is introduced, wherein the DNAs are:

(a) DNA encoding a protein that consists of an amino acid sequence as set forth in SEQ ID NO: 2, 4, or 6;

(b) DNA encoding a protein that consists of an amino acid sequence having 80% or higher identity to an amino acid sequence as set forth in SEQ ID NO: 2, 4, or 6, and has an activity to hydroxylate position 23 of a spirosolane skeleton;

(c) DNA encoding a protein that consists of an amino acid sequence as set forth in SEQ ID NO: 8, 10, or 12; and (d) DNA encoding a protein that consists of an amino acid sequence having 80% or higher identity to an amino acid sequence as set forth in SEQ ID NO: 8, 10, or 12, and has an activity to acetylate a hydroxy group of position 23 of a spirosolane skeleton.

4. A method for producing a *Solanum tuberosum* plant having resistance against Colorado potato beetle, the method comprising:

crossing a *Solanum tuberosum* plant having at least one DNA selected from the group consisting of (a) to (b) below, with a *Solanum tuberosum* plant having at least one DNA selected from the group consisting of (c) to (d) below;

determining the resistance against Colorado potato beetle in a *Solanum tuberosum* plant obtained in the crossing, and selecting a *Solanum tuberosum* plant that is determined to have the resistance to Colorado potato beetle, wherein the DNAs are (a) DNA encoding a protein that consists of an amino acid sequence as set forth in SEQ ID NO: 2, 4, or 6;

(b) DNA encoding a protein that consists of an amino acid sequence having 80% or higher identity to an amino acid sequence as set forth in SEQ ID NO: 2, 4, or 6, and has an activity to hydroxylate position 23 of a spirosolane skeleton;

(c) DNA encoding a protein that consists of an amino acid sequence as set forth in SEQ ID NO: 8, 10, or 12; and (d) DNA encoding a protein that consists of an amino acid sequence having 80% or higher identity to an amino acid sequence as set forth in SEQ ID NO: 8, 10, or 12, and has an activity to acetylate a hydroxy group of position 23 of a spirosolane skeleton.

5. The transformed cell that is capable of regenerating into a *Solanum tuberosum* plant having increased resistance against Colorado potato beetle according to claim 1, wherein the transformed cell has 1.1 times or higher expression of endogenous DNA-of (a) compared to an untransformed plant cell or has 1.1 times or higher expression of RNA corresponding to (a) compared to an untransformed plant cell, and the transformed cell has 1.1 times or higher expression of endogenous DNA of (b) compared to the untransformed plant cell or has 1.1 times or higher expression of RNA corresponding to (b) compared to the untransformed plant cell.

6. The production method according to claim 3, wherein the *Solanum tuberosum* plant has an increased accumulation amount of leptine.

* * * * *

SEQUENCE LISTING

```
<160> NUMBER OF SEQ ID NOS: 49

<210> SEQ ID NO 1
<211> LENGTH: 960
<212> TYPE: DNA
<213> ORGANISM: Solanum chacoense

<400> SEQUENCE: 1

atggcatcta ccaaatcagt taaagttccc accatagatt tttccaatct tgaagagcta      60

aaaccaaact ctccactatg ggaatctaca aaaattcaag tttttgaagc tttacaagaa     120

tatggttgtt ttgaagccat atataaagtt ccaaatgaaa ttaaagatgg aatgcttggt     180

atttcaaaag aaatatttga atttccttta gaaaccaaat tgaaaaattt ctcagaaaaa     240

ccaatgcatg ggtatatggg gatgattcca caattgccat tgtatgagag tttgtgtatt     300

cctgatttgc ttaatcctca aagtcttgaa acttttgcta atatcttttg gcctcagggt     360

aatcaccatt tctgcgattt ggtaaaatct tattctaatc cacttgtgga attggatgag     420

atgttgaaaa ggatgatttc ggagaatttg ggattaaaaa atcacattga tgaattgttg     480

aataccaatt atttcctatt tagatttaca cattataagg gatcatcaat tattagtgga     540

gatggaaata ataaaactgc tggattgggt ggccacacag atggtaactt cttgactttt     600

atatcacaaa atcaagtcaa tggattgcaa atcaacaaaa atggagagtg gatcgatgtg     660

aatatttcac caaattcttg tgttgttttg gctggtgatt ccttcaaagc atggacaaat     720

ggtcgattgc attctcctgt ccacagagta acaatggcag gagaaagtga tagactctcc     780

attcaattat tttcattatc aaaaccaggt cacttcatcg aggcaccaaa agaactggtg     840

gatgaagaac accctttact cttcaagcca tttgaaattc ttggattatt tgggtatgct     900

tcctcagaag ctggctatgg agctcctccc agtgatgttt tcaagactta ttgcggtgtt     960


<210> SEQ ID NO 2
<211> LENGTH: 320
<212> TYPE: PRT
<213> ORGANISM: Solanum chacoense

<400> SEQUENCE: 2

Met Ala Ser Thr Lys Ser Val Lys Val Pro Thr Ile Asp Phe Ser Asn
1               5                   10                  15
```

-continued

```
Leu Glu Glu Leu Lys Pro Asn Ser Pro Leu Trp Glu Ser Thr Lys Ile
            20                  25                  30

Gln Val Phe Glu Ala Leu Gln Glu Tyr Gly Cys Phe Glu Ala Ile Tyr
        35                  40                  45

Lys Val Pro Asn Glu Ile Lys Asp Gly Met Leu Gly Ile Ser Lys Glu
    50                  55                  60

Ile Phe Glu Phe Pro Leu Glu Thr Lys Leu Lys Asn Phe Ser Glu Lys
65                  70                  75                  80

Pro Met His Gly Tyr Met Gly Met Ile Pro Gln Leu Pro Leu Tyr Glu
                85                  90                  95

Ser Leu Cys Ile Pro Asp Leu Leu Asn Pro Gln Ser Leu Glu Thr Phe
            100                 105                 110

Ala Asn Ile Phe Trp Pro Gln Gly Asn His His Phe Cys Asp Leu Val
        115                 120                 125

Lys Ser Tyr Ser Asn Pro Leu Val Glu Leu Asp Glu Met Leu Lys Arg
    130                 135                 140

Met Ile Ser Glu Asn Leu Gly Leu Lys Asn His Ile Asp Glu Leu Leu
145                 150                 155                 160

Asn Thr Asn Tyr Phe Leu Phe Arg Phe Thr His Tyr Lys Gly Ser Ser
                165                 170                 175

Ile Ile Ser Gly Asp Gly Asn Asn Lys Thr Ala Gly Leu Gly Gly His
            180                 185                 190

Thr Asp Gly Asn Phe Leu Thr Phe Ile Ser Gln Asn Gln Val Asn Gly
        195                 200                 205

Leu Gln Ile Asn Lys Asn Gly Glu Trp Ile Asp Val Asn Ile Ser Pro
    210                 215                 220

Asn Ser Cys Val Val Leu Ala Gly Asp Ser Phe Lys Ala Trp Thr Asn
225                 230                 235                 240

Gly Arg Leu His Ser Pro Val His Arg Val Thr Met Ala Gly Glu Ser
                245                 250                 255

Asp Arg Leu Ser Ile Gln Leu Phe Ser Leu Ser Lys Pro Gly His Phe
            260                 265                 270

Ile Glu Ala Pro Lys Glu Leu Val Asp Glu Glu His Pro Leu Leu Phe
        275                 280                 285

Lys Pro Phe Glu Ile Leu Gly Leu Phe Gly Tyr Ala Ser Ser Glu Ala
    290                 295                 300

Gly Tyr Gly Ala Pro Pro Ser Asp Val Phe Lys Thr Tyr Cys Gly Val
305                 310                 315                 320


<210> SEQ ID NO 3
<211> LENGTH: 960
<212> TYPE: DNA
<213> ORGANISM: Solanum tuberosum

<400> SEQUENCE: 3

atggcatcta ccaaatcagt taaagtcccc gccattgatt tttccaatta tcaagagcta      60

aaaccaaaca ctccattatg ggaatccaca aaaattcaaa tttttgaagc tttacaagaa     120

tatggttgtt ttgaagcaat atataaagtt ccaaatgaaa ttaaagatgg aatgtttggt     180

atttcaaaag aaatatttga atttccttta gaaaccaaat tgaaaaattt ctcagaaaaa     240

ccattacatg gctacatggg aatgattcca caattgccat tgtatgagag tttatgtatt     300

cctgatttgc ttaatcgtca aagtcttgaa actttttcta atatcttttg gcctcatggt     360

aatcaacatt tctgcgattt ggtaaaatct tattctaatc cacttgtgga attggatgag     420
```

```
atgttgaaaa ggatgatttc ggagaatttg ggattaaaaa atcacattga tgaattgttg    480

aataccaatt atttcctatt tagatttaca cattataagg gatcatcaat tattagtgga    540

gatgaaaata ataaaactac tggattgggt ggccacacag atggtaactt cttaactttt    600

atatcacaaa atcaagtcaa tggattgcaa atcaacaaaa atggagagtg gattgatgtg    660

aatatttcac caaattcttg tgttgttttg gctggtgatt ccttcaaagc atggacaaat    720

ggtcaattac attctcctct ccacagagta acaattgccg gagaaagtga tagactttct    780

attcaattat tttcattatc aaaaccaggt cacttcatcg aggcaccaca agaactggtg    840

gatgaagaac accctttact cttcaagcca tttgaaattc ttggattatt tgggtatgct    900

gcctcagaag ctggctatgg agctcctccc agtgatcttt tcaagactta ttgcggtgtt    960
```

<210> SEQ ID NO 4
<211> LENGTH: 320
<212> TYPE: PRT
<213> ORGANISM: Solanum tuberosum

<400> SEQUENCE: 4

```
Met Ala Ser Thr Lys Ser Val Lys Val Pro Ala Ile Asp Phe Ser Asn
1               5                   10                  15

Tyr Gln Glu Leu Lys Pro Asn Thr Pro Leu Trp Glu Ser Thr Lys Ile
            20                  25                  30

Gln Ile Phe Glu Ala Leu Gln Glu Tyr Gly Cys Phe Glu Ala Ile Tyr
        35                  40                  45

Lys Val Pro Asn Glu Ile Lys Asp Gly Met Phe Gly Ile Ser Lys Glu
    50                  55                  60

Ile Phe Glu Phe Pro Leu Glu Thr Lys Leu Lys Asn Phe Ser Glu Lys
65                  70                  75                  80

Pro Leu His Gly Tyr Met Gly Met Ile Pro Gln Leu Pro Leu Tyr Glu
                85                  90                  95

Ser Leu Cys Ile Pro Asp Leu Leu Asn Arg Gln Ser Leu Glu Thr Phe
            100                 105                 110

Ser Asn Ile Phe Trp Pro His Gly Asn Gln His Phe Cys Asp Leu Val
        115                 120                 125

Lys Ser Tyr Ser Asn Pro Leu Val Glu Leu Asp Glu Met Leu Lys Arg
    130                 135                 140

Met Ile Ser Glu Asn Leu Gly Leu Lys Asn His Ile Asp Glu Leu Leu
145                 150                 155                 160

Asn Thr Asn Tyr Phe Leu Phe Arg Phe Thr His Tyr Lys Gly Ser Ser
                165                 170                 175

Ile Ile Ser Gly Asp Glu Asn Asn Lys Thr Thr Gly Leu Gly Gly His
            180                 185                 190

Thr Asp Gly Asn Phe Leu Thr Phe Ile Ser Gln Asn Gln Val Asn Gly
        195                 200                 205

Leu Gln Ile Asn Lys Asn Gly Glu Trp Ile Asp Val Asn Ile Ser Pro
    210                 215                 220

Asn Ser Cys Val Val Leu Ala Gly Asp Ser Phe Lys Ala Trp Thr Asn
225                 230                 235                 240

Gly Gln Leu His Ser Pro Leu His Arg Val Thr Ile Ala Gly Glu Ser
                245                 250                 255

Asp Arg Leu Ser Ile Gln Leu Phe Ser Leu Ser Lys Pro Gly His Phe
            260                 265                 270

Ile Glu Ala Pro Gln Glu Leu Val Asp Glu Glu His Pro Leu Leu Phe
```

-continued

```
        275                 280                 285

Lys Pro Phe Glu Ile Leu Gly Leu Phe Gly Tyr Ala Ala Ser Glu Ala
    290                 295                 300

Gly Tyr Gly Ala Pro Pro Ser Asp Leu Phe Lys Thr Tyr Cys Gly Val
305                 310                 315                 320


<210> SEQ ID NO 5
<211> LENGTH: 963
<212> TYPE: DNA
<213> ORGANISM: Solanum lycopersicum

<400> SEQUENCE: 5

atggcatcta tcaaatcagt taaagttcct actatagatt tttccaatta tcaagagcta      60

aaaccaaaca ctccactatg ggaatccaca aaaattcaag tttttgaagc ttttcaagaa     120

tatggttgtt ttgaagcaat atatgataaa gttccaaatg aaattagaga ggaaacattt     180

gatatgtcaa aagaaatatt tgaatttcct ttagatacta aagtgaaaaa tatttcagaa     240

aaaccaatgc atggatatat gggaatgatt ccacaattgc cattgtatga gagtttgtgt     300

attcctgatt tgcttaatcc tcaaagtctt caaaattttg ctaatatctt ttggcctcag     360

ggtaatcaac atttctgcaa tttggtaaag tcttattcta atccacttgt ggaattggat     420

gagattttga aaaggatgat ttcggagaat ttgagattaa aaattcacat tgatgaattg     480

ttgaatgcca attatttcct atttagattt acacattaca agggatcatc aattgctagt     540

ggagatgaaa ataataaagc tgctggattg ggtggccaca cggatggtaa cttcttgact     600

tttatatcgc aaaatcaagt taatggattg caaatcaaca aaaatggaga atggattgat     660

gtgattattt caccaaattc ttacgttgtt ttggccggtg attccttcaa agcttggaca     720

aatggtcgat tgcattcacc tctccacaga gtaacaatgt ccggacaaaa tgatagactc     780

tccattcaat tgttttcatt atcaaagcca ggtcacttca tccaggcacc aaaagaacta     840

gtagatgaag aacacccatt actcttcaag ccatttgaaa ttcttgaatt attcaagtat     900

ggtaccacag aagctggcta tacagctcct ccaagtgatc ttttcaagat ttattgtggt     960

gtt                                                                   963


<210> SEQ ID NO 6
<211> LENGTH: 321
<212> TYPE: PRT
<213> ORGANISM: Solanum lycopersicum

<400> SEQUENCE: 6

Met Ala Ser Ile Lys Ser Val Lys Val Pro Thr Ile Asp Phe Ser Asn
1               5                   10                  15

Tyr Gln Glu Leu Lys Pro Asn Thr Pro Leu Trp Glu Ser Thr Lys Ile
            20                  25                  30

Gln Val Phe Glu Ala Phe Gln Glu Tyr Gly Cys Phe Glu Ala Ile Tyr
        35                  40                  45

Asp Lys Val Pro Asn Glu Ile Arg Glu Glu Thr Phe Asp Met Ser Lys
    50                  55                  60

Glu Ile Phe Glu Phe Pro Leu Asp Thr Lys Val Lys Asn Ile Ser Glu
65                  70                  75                  80

Lys Pro Met His Gly Tyr Met Gly Met Ile Pro Gln Leu Pro Leu Tyr
                85                  90                  95

Glu Ser Leu Cys Ile Pro Asp Leu Leu Asn Pro Gln Ser Leu Gln Asn
            100                 105                 110
```

-continued

```
Phe Ala Asn Ile Phe Trp Pro Gln Gly Asn Gln His Phe Cys Asn Leu
        115                 120                 125

Val Lys Ser Tyr Ser Asn Pro Leu Val Glu Leu Asp Glu Ile Leu Lys
    130                 135                 140

Arg Met Ile Ser Glu Asn Leu Arg Leu Lys Ile His Ile Asp Glu Leu
145                 150                 155                 160

Leu Asn Ala Asn Tyr Phe Leu Phe Arg Phe Thr His Tyr Lys Gly Ser
                165                 170                 175

Ser Ile Ala Ser Gly Asp Glu Asn Asn Lys Ala Ala Gly Leu Gly Gly
            180                 185                 190

His Thr Asp Gly Asn Phe Leu Thr Phe Ile Ser Gln Asn Gln Val Asn
        195                 200                 205

Gly Leu Gln Ile Asn Lys Asn Gly Glu Trp Ile Asp Val Ile Ile Ser
    210                 215                 220

Pro Asn Ser Tyr Val Val Leu Ala Gly Asp Ser Phe Lys Ala Trp Thr
225                 230                 235                 240

Asn Gly Arg Leu His Ser Pro Leu His Arg Val Thr Met Ser Gly Gln
                245                 250                 255

Asn Asp Arg Leu Ser Ile Gln Leu Phe Ser Leu Ser Lys Pro Gly His
            260                 265                 270

Phe Ile Gln Ala Pro Lys Glu Leu Val Asp Glu Glu His Pro Leu Leu
        275                 280                 285

Phe Lys Pro Phe Glu Ile Leu Glu Leu Phe Lys Tyr Gly Thr Thr Glu
    290                 295                 300

Ala Gly Tyr Thr Ala Pro Pro Ser Asp Leu Phe Lys Ile Tyr Cys Gly
305                 310                 315                 320

Val


<210> SEQ ID NO 7
<211> LENGTH: 1302
<212> TYPE: DNA
<213> ORGANISM: Solanum chacoense

<400> SEQUENCE: 7

atggcagcat caagttgtgt atctttggtt gaaaagttta ttaagcctga ttctcctacc      60

ccttcttcac ttaggcgtta caatctttgt ctaacagatc aaatcatggt tccagtctac     120

atgccaattg tagcctttta tcctttctcc tctaaaacac cacaacaaat atctaacatt     180

cttgaaaatt cactatccaa agttttgtcc tcttattatc catttgctgg aacactcgga     240

gatgacaaca cttttgtcga ttgcaacgat aggggagcca aatttatgaa cgttcgatac     300

gattgtccat tgtctgaaat cgtcaatctt ccagacactg gccctgaata tctacctttt     360

gctaaaggta tgccttgggg ttcaactcca gatgacaaaa gtttacttgt tgtccaatta     420

agccatttta attgcggagg attagctata agtgttaggc tatcacacaa aattgctgat     480

ggatgcacac tctgcaattt tattagtgat tgggcttcca tagctcgtga tgagaacgcg     540

aatatacctt cccctgaaat gattggatcg tccatttttc cgccatccac tgaaatgcca     600

tccactggca ttcacatgga tactgagttt gattatgaat tttacaattt gcccgttatt     660

aaaaaaaggt acctattttc caattcgaaa cttgagatgc tgaaaagtca agtgacatca     720

gaaacagggg tgcaaaatcc tagccgactt gaagtgttgt ttgcactaat ttacaagtgt     780

gctgcaacag cagctcgagc aaactcgagc tcgtttaaac gatcctcgtt gtcactacct     840

gtaaatttac gtccaatatt ggatccacca ctagcaacac ggacaatagg gaatattctt     900
```

-continued

```
agttttatca aagtggaaac aatgagtgag gatgaaatga caatcgccag agtggttcgt    960

gagataagga aaggtaaaga agaactgaag aaggaggggc atgtggagga gaagaagtta   1020

gtgtcgcttt ggtctgagtg gatatattcg atgggtaaag aaattgaact gtatcgaagt   1080

agcagtgttt gcaattgccc attgaataat ttggattttg gatggggaaa gccaagcagg   1140

gtaacaattc cagtatatgg gactgcaaac acctgcatgt ttatggataa tctaagtgga   1200

gatgggattg acgtaattat tgtattacca gaaaaagacg tgactcaatt tgagaatagc   1260

aaagacctca tccagttctc ttctccaatt actaatctta at                      1302
```

<210> SEQ ID NO 8
<211> LENGTH: 434
<212> TYPE: PRT
<213> ORGANISM: Solanum chacoense

<400> SEQUENCE: 8

```
Met Ala Ala Ser Ser Cys Val Ser Leu Val Glu Lys Phe Ile Lys Pro
1               5                   10                  15

Asp Ser Pro Thr Pro Ser Ser Leu Arg Arg Tyr Asn Leu Cys Leu Thr
            20                  25                  30

Asp Gln Ile Met Val Pro Val Tyr Met Pro Ile Val Ala Phe Tyr Pro
        35                  40                  45

Phe Ser Ser Lys Thr Pro Gln Gln Ile Ser Asn Ile Leu Glu Asn Ser
    50                  55                  60

Leu Ser Lys Val Leu Ser Ser Tyr Tyr Pro Phe Ala Gly Thr Leu Gly
65                  70                  75                  80

Asp Asp Asn Thr Phe Val Asp Cys Asn Asp Arg Gly Ala Lys Phe Met
                85                  90                  95

Asn Val Arg Tyr Asp Cys Pro Leu Ser Glu Ile Val Asn Leu Pro Asp
            100                 105                 110

Thr Gly Pro Glu Tyr Leu Pro Phe Ala Lys Gly Met Pro Trp Gly Ser
        115                 120                 125

Thr Pro Asp Asp Lys Ser Leu Leu Val Val Gln Leu Ser His Phe Asn
    130                 135                 140

Cys Gly Gly Leu Ala Ile Ser Val Arg Leu Ser His Lys Ile Ala Asp
145                 150                 155                 160

Gly Cys Thr Leu Cys Asn Phe Ile Ser Asp Trp Ala Ser Ile Ala Arg
                165                 170                 175

Asp Glu Asn Ala Asn Ile Pro Ser Pro Glu Met Ile Gly Ser Ser Ile
            180                 185                 190

Phe Pro Pro Ser Thr Glu Met Pro Ser Thr Gly Ile His Met Asp Thr
        195                 200                 205

Glu Phe Asp Tyr Glu Phe Tyr Asn Leu Pro Val Ile Lys Lys Arg Tyr
    210                 215                 220

Leu Phe Ser Asn Ser Lys Leu Glu Met Leu Lys Ser Gln Val Thr Ser
225                 230                 235                 240

Glu Thr Gly Val Gln Asn Pro Ser Arg Leu Glu Val Leu Phe Ala Leu
                245                 250                 255

Ile Tyr Lys Cys Ala Ala Thr Ala Ala Arg Ala Asn Ser Ser Ser Phe
            260                 265                 270

Lys Arg Ser Ser Leu Ser Leu Pro Val Asn Leu Arg Pro Ile Leu Asp
        275                 280                 285

Pro Pro Leu Ala Thr Arg Thr Ile Gly Asn Ile Leu Ser Phe Ile Lys
    290                 295                 300
```

```
Val Glu Thr Met Ser Glu Asp Glu Met Thr Ile Ala Arg Val Val Arg
305                 310                 315                 320

Glu Ile Arg Lys Gly Lys Glu Glu Leu Lys Lys Glu Gly His Val Glu
                325                 330                 335

Glu Lys Lys Leu Val Ser Leu Trp Ser Glu Trp Ile Tyr Ser Met Gly
            340                 345                 350

Lys Glu Ile Glu Leu Tyr Arg Ser Ser Ser Val Cys Asn Cys Pro Leu
        355                 360                 365

Asn Asn Leu Asp Phe Gly Trp Gly Lys Pro Ser Arg Val Thr Ile Pro
    370                 375                 380

Val Tyr Gly Thr Ala Asn Thr Cys Met Phe Met Asp Asn Leu Ser Gly
385                 390                 395                 400

Asp Gly Ile Asp Val Ile Ile Val Leu Pro Glu Lys Asp Val Thr Gln
                405                 410                 415

Phe Glu Asn Ser Lys Asp Leu Ile Gln Phe Ser Ser Pro Ile Thr Asn
            420                 425                 430

Leu Asn


<210> SEQ ID NO 9
<211> LENGTH: 1302
<212> TYPE: DNA
<213> ORGANISM: Solanum tuberosum

<400> SEQUENCE: 9

atggcagcat caagttgtgt atctttggct gaaaagatta ttaagcctga ttcttctacc     60

ccttcttcac ttaggcgtta caatctttgt ctaattgatc aaatcatggt tccagtctac    120

atgccaattg tagcctttta tcctttctcc tctaaaacac cacaacaagt atccagcatt    180

cttgaaaatt cactatccaa agttttgtcc tcttattatc catttgctgg aacactcgga    240

gataacaaca cttttgtcga ttgcaacgat aggggagcca aatttatgaa cgttcgatac    300

gattgtccaa tgtctgaaat cgtcaatctt ccggacactg gccctgaata tctacctttt    360

gctaaaggta tgccttgggg ttcaactcca gatgacaaaa gtttacttgt tgttcaatta    420

agccatttta attgcggagg attagctata agtgttaggc tatcacacaa aattgctgat    480

ggatgcacac tctgcaattt tattagtgat tgggcttcca tagctcgtga tgagaacgcg    540

aatatacctt cccctgaaat gattggatcg tccatttttc tgccatccac tgaaatgcca    600

tccactggca ttcacatgga tactgaggtt gattatgaat tttacaattt acccgttagt    660

aaaaaaaggt acctattttc caattcaaaa cttgagatgc tgaaaagtca agtggcatca    720

gaaacagggg tgcaagatcc tagccgagtt gaagtgttgt ttgcactaat ttacaagtgt    780

gctgcaacag cagttcgagc aaacttgagc ttgtttaaac gatcttcatt gtcaatacct    840

gtgaacttac gtccaatatt ggatccacca ctagcaacac ggacaatagg gaatattctt    900

agttttatca aagtggaaac aatgagtgag gatgaaatga caattggcag aatggttcgc    960

gagataagaa aagctaaaga tgaagtgagg aaggaggggc atgtgaagga ggagaagcta   1020

gtgtcgcttt ggactgagtg gatatattcg atgggtaaag aaattgaatt ttatagaagt   1080

agcagtgttt gcaattaccc attgaataat ttggattttg gattgggaaa gccaagcagg   1140

gtaacaattc cagtatatgg gattgccaac acctgcatgt ttatggataa tctaagtgga   1200

gatgggattg aggtacttat tgcattacca gaaaaagacg tgactcaatt tgagaataac   1260

aaagagctcc tccagtttgg ttctccaatt actaatctta at                      1302
```

```
<210> SEQ ID NO 10
<211> LENGTH: 434
<212> TYPE: PRT
<213> ORGANISM: Solanum tuberosum

<400> SEQUENCE: 10

Met Ala Ala Ser Ser Cys Val Ser Leu Ala Glu Lys Ile Ile Lys Pro
1               5                   10                  15

Asp Ser Ser Thr Pro Ser Ser Leu Arg Arg Tyr Asn Leu Cys Leu Ile
            20                  25                  30

Asp Gln Ile Met Val Pro Val Tyr Met Pro Ile Val Ala Phe Tyr Pro
        35                  40                  45

Phe Ser Ser Lys Thr Pro Gln Gln Val Ser Ser Ile Leu Glu Asn Ser
    50                  55                  60

Leu Ser Lys Val Leu Ser Ser Tyr Tyr Pro Phe Ala Gly Thr Leu Gly
65                  70                  75                  80

Asp Asn Asn Thr Phe Val Asp Cys Asn Asp Arg Gly Ala Lys Phe Met
                85                  90                  95

Asn Val Arg Tyr Asp Cys Pro Met Ser Glu Ile Val Asn Leu Pro Asp
            100                 105                 110

Thr Gly Pro Glu Tyr Leu Pro Phe Ala Lys Gly Met Pro Trp Gly Ser
        115                 120                 125

Thr Pro Asp Asp Lys Ser Leu Leu Val Val Gln Leu Ser His Phe Asn
    130                 135                 140

Cys Gly Gly Leu Ala Ile Ser Val Arg Leu Ser His Lys Ile Ala Asp
145                 150                 155                 160

Gly Cys Thr Leu Cys Asn Phe Ile Ser Asp Trp Ala Ser Ile Ala Arg
                165                 170                 175

Asp Glu Asn Ala Asn Ile Pro Ser Pro Glu Met Ile Gly Ser Ser Ile
            180                 185                 190

Phe Leu Pro Ser Thr Glu Met Pro Ser Thr Gly Ile His Met Asp Thr
        195                 200                 205

Glu Val Asp Tyr Glu Phe Tyr Asn Leu Pro Val Ser Lys Lys Arg Tyr
    210                 215                 220

Leu Phe Ser Asn Ser Lys Leu Glu Met Leu Lys Ser Gln Val Ala Ser
225                 230                 235                 240

Glu Thr Gly Val Gln Asp Pro Ser Arg Val Glu Val Leu Phe Ala Leu
                245                 250                 255

Ile Tyr Lys Cys Ala Ala Thr Ala Val Arg Ala Asn Leu Ser Leu Phe
            260                 265                 270

Lys Arg Ser Ser Leu Ser Ile Pro Val Asn Leu Arg Pro Ile Leu Asp
        275                 280                 285

Pro Pro Leu Ala Thr Arg Thr Ile Gly Asn Ile Leu Ser Phe Ile Lys
    290                 295                 300

Val Glu Thr Met Ser Glu Asp Glu Met Thr Ile Gly Arg Met Val Arg
305                 310                 315                 320

Glu Ile Arg Lys Ala Lys Asp Glu Val Arg Lys Glu Gly His Val Lys
                325                 330                 335

Glu Glu Lys Leu Val Ser Leu Trp Thr Glu Trp Ile Tyr Ser Met Gly
            340                 345                 350

Lys Glu Ile Glu Phe Tyr Arg Ser Ser Ser Val Cys Asn Tyr Pro Leu
        355                 360                 365

Asn Asn Leu Asp Phe Gly Leu Gly Lys Pro Ser Arg Val Thr Ile Pro
    370                 375                 380
```

-continued

```
Val Tyr Gly Ile Ala Asn Thr Cys Met Phe Met Asp Asn Leu Ser Gly
385                 390                 395                 400

Asp Gly Ile Glu Val Leu Ile Ala Leu Pro Glu Lys Asp Val Thr Gln
                405                 410                 415

Phe Glu Asn Asn Lys Glu Leu Leu Gln Phe Gly Ser Pro Ile Thr Asn
            420                 425                 430

Leu Asn


<210> SEQ ID NO 11
<211> LENGTH: 1272
<212> TYPE: DNA
<213> ORGANISM: Solanum lycopersicum

<400> SEQUENCE: 11

atgacagcat caagttttgt atctatggct gaaaagatta ttaagcctca ttctcctacc      60

ccttttttcag ttaagcgtta caatctttgt ctaatggatg aaatcatggt tccagtctac    120

atgccaattg tagcctttta tcctaacccc tctaaaacac cagaacaagt atccaacata    180

cttgaagatt cactatccaa agttttatcc tcttactatc catttgctgg aacactcgga    240

tcagataacg ctacttttgt cgattgcaat gacaggggag ctaaatctat acaggttcga    300

tacgattgtc caatgtctga aatagtcaat cttccggata ctggccctga atatctacct    360

tttgctaaag gtacgccttg gagttcaact ccagaggaac aaagtttact agttgttcaa    420

ttaagccatt ttaattgcgg aggattaggt ataagtgcta ggctatccca taaaattgct    480

gatggatgca cgctcgccaa tttcattagt gattgggctt ccgtagctcg tgatgacaac    540

gcgaatatac cttcccctca attgattgga tcgtccattt ttccgccatt cactgaaatg    600

cgcattcaca cggatactaa cgttgattat gagttttaca atctacccgt ttgtaaaaaa    660

aggtacttgt tttccaacgc gaaacttgag atgctgaaaa cccaagtgga atcagaaaca    720

ggggtgcaaa atccaactcg aattgaagtg ctgtccgcac taatttacaa gtgtgctgta    780

acagcaaact cgagctcgtt tagaccatcc tcgttgtcac tgccggtgaa tttacgtccg    840

atactgaatc caccgctaga aacacggaca gtagggaata ttattagttt tatcaaagtg    900

gaaacaacga gtgaggatga aatgacaatc gggagagtgg ttcgcgagat taggaaaggt    960

aaagacgaat tgaagcagga agggggtgtg aagaaggaga agctagtttc gctatggagt   1020

gagtggatac attcgattga cttgtacaga agtagcagtg tttgcaatta cccattgaat   1080

aatttggatt ttggatgggg aaaaccaaac agggtagcaa ttcctgtatt tggagttgca   1140

aacacctgca tgtttatgga taatctaagt ggagatggaa ttgaggtaat tattgcatta   1200

ccagaaaaag atgcgactca atttgagaat agcaaagagc ttctccactt tgcttctcca   1260

gttacgaatc tc                                                         1272


<210> SEQ ID NO 12
<211> LENGTH: 424
<212> TYPE: PRT
<213> ORGANISM: Solanum lycopersicum

<400> SEQUENCE: 12

Met Thr Ala Ser Ser Phe Val Ser Met Ala Glu Lys Ile Ile Lys Pro
1               5                   10                  15

His Ser Pro Thr Pro Phe Ser Val Lys Arg Tyr Asn Leu Cys Leu Met
            20                  25                  30

Asp Glu Ile Met Val Pro Val Tyr Met Pro Ile Val Ala Phe Tyr Pro
        35                  40                  45
```

```
Asn Pro Ser Lys Thr Pro Glu Gln Val Ser Asn Ile Leu Glu Asp Ser
    50                  55                  60

Leu Ser Lys Val Leu Ser Ser Tyr Tyr Pro Phe Ala Gly Thr Leu Gly
65                  70                  75                  80

Ser Asp Asn Ala Thr Phe Val Asp Cys Asn Asp Arg Gly Ala Lys Ser
                85                  90                  95

Ile Gln Val Arg Tyr Asp Cys Pro Met Ser Glu Ile Val Asn Leu Pro
            100                 105                 110

Asp Thr Gly Pro Glu Tyr Leu Pro Phe Ala Lys Gly Thr Pro Trp Ser
        115                 120                 125

Ser Thr Pro Glu Glu Gln Ser Leu Leu Val Val Gln Leu Ser His Phe
    130                 135                 140

Asn Cys Gly Gly Leu Gly Ile Ser Ala Arg Leu Ser His Lys Ile Ala
145                 150                 155                 160

Asp Gly Cys Thr Leu Ala Asn Phe Ile Ser Asp Trp Ala Ser Val Ala
                165                 170                 175

Arg Asp Asp Asn Ala Asn Ile Pro Ser Pro Gln Leu Ile Gly Ser Ser
            180                 185                 190

Ile Phe Pro Pro Phe Thr Glu Met Arg Ile His Thr Asp Thr Asn Val
        195                 200                 205

Asp Tyr Glu Phe Tyr Asn Leu Pro Val Cys Lys Lys Arg Tyr Leu Phe
    210                 215                 220

Ser Asn Ala Lys Leu Glu Met Leu Lys Thr Gln Val Glu Ser Glu Thr
225                 230                 235                 240

Gly Val Gln Asn Pro Thr Arg Ile Glu Val Leu Ser Ala Leu Ile Tyr
                245                 250                 255

Lys Cys Ala Val Thr Ala Asn Ser Ser Ser Phe Arg Pro Ser Ser Leu
            260                 265                 270

Ser Leu Pro Val Asn Leu Arg Pro Ile Leu Asn Pro Pro Leu Glu Thr
        275                 280                 285

Arg Thr Val Gly Asn Ile Ile Ser Phe Ile Lys Val Glu Thr Thr Ser
    290                 295                 300

Glu Asp Glu Met Thr Ile Gly Arg Val Val Arg Glu Ile Arg Lys Gly
305                 310                 315                 320

Lys Asp Glu Leu Lys Gln Glu Gly Gly Val Lys Lys Glu Lys Leu Val
                325                 330                 335

Ser Leu Trp Ser Glu Trp Ile His Ser Ile Asp Leu Tyr Arg Ser Ser
            340                 345                 350

Ser Val Cys Asn Tyr Pro Leu Asn Asn Leu Asp Phe Gly Trp Gly Lys
        355                 360                 365

Pro Asn Arg Val Ala Ile Pro Val Phe Gly Val Ala Asn Thr Cys Met
    370                 375                 380

Phe Met Asp Asn Leu Ser Gly Asp Gly Ile Glu Val Ile Ile Ala Leu
385                 390                 395                 400

Pro Glu Lys Asp Ala Thr Gln Phe Glu Asn Ser Lys Glu Leu Leu His
                405                 410                 415

Phe Ala Ser Pro Val Thr Asn Leu
            420
```

<210> SEQ ID NO 13
<211> LENGTH: 25
<212> TYPE: DNA
<213> ORGANISM: Artificial Sequence
<220> FEATURE:

<223> OTHER INFORMATION: Artificially synthesized primer sequence

<400> SEQUENCE: 13
ggatccatgg catctatcaa atcag 25

<210> SEQ ID NO 14
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 14
ctcgagtcaa aataccacaa taaatcttg 29

<210> SEQ ID NO 15
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 15
ctwaaaccaa acactycayw atgggaat 28

<210> SEQ ID NO 16
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 16
gggtgttywt catcyacwar ttcttttgg 29

<210> SEQ ID NO 17
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 17
tggtgattac cctgaggcca aaaga 25

<210> SEQ ID NO 18
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 18
ggtcgattgc attctcctgt ccac 24

<210> SEQ ID NO 19
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 19
catatggcat ctaccaaatc agttaaagt 29

<210> SEQ ID NO 20
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 20
gtcgactcaa acaccgcaat aagtcttga 29

<210> SEQ ID NO 21
<211> LENGTH: 36
<212> TYPE: DNA
<213> ORGANISM: Artificial Sequence
<220> FEATURE:
<223> OTHER INFORMATION: Artificially synthesized primer sequence

<400> SEQUENCE: 21
ggatcccata tgacagcatc aagttttgta tctatg 36

<210> SEQ ID NO 22
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 22
gtcgacctag agattcgtaa ctggagaagc 30

<210> SEQ ID NO 23
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 23
tgccatccac tggcattcac atgg 24

<210> SEQ ID NO 24
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 24
catatggcag catcaagttg tgtat 25

<210> SEQ ID NO 25
<211> LENGTH: 33
<212> TYPE: DNA
<213> ORGANISM: Artificial Sequence
<220> FEATURE:
<223> OTHER INFORMATION: Artificially synthesized primer sequence

<400> SEQUENCE: 25
gtcgacttaa ttaagattag taattggaga aga 33

<210> SEQ ID NO 26
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 26
ggcatctacc aaatcagtta aag 23

<210> SEQ ID NO 27
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 27
gtcttgaaaa catcactggg ag 22

<210> SEQ ID NO 28
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 28
gattatgaat tttacaattt g 21

<210> SEQ ID NO 29
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 29
tacaggtagt gacaacgagg atc 23

<210> SEQ ID NO 30
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 30
caccatggca tctaccaaat cagttaaag 29

<210> SEQ ID NO 31
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 31
tcaaacaccg caataagtct tgaaa 25

<210> SEQ ID NO 32
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 32
catatggcag catcaagttg tgt 23

<210> SEQ ID NO 33
<211> LENGTH: 32

```
<212> TYPE: DNA
<213> ORGANISM: Artificial Sequence
<220> FEATURE:
<223> OTHER INFORMATION: Artificially synthesized primer sequence

<400> SEQUENCE: 33

gtcgacttaa ttaagattag taattggaga ag                                32


<210> SEQ ID NO 34
<211> LENGTH: 1693
<212> TYPE: DNA
<213> ORGANISM: Solanum chacoense
<220> FEATURE:
<223> OTHER INFORMATION: 23ACT promoter

<400> SEQUENCE: 34

tcagcaatag tgcattacca gagtaagacg tgactcaatt tgagaatagc aaagagctcc    60

tcctgttcgc ttctccaatt acaataatca agaatggaga aatatagcaa caatcgtttt   120

gttgatttta aagtgcgagt gttacaatct ctattattcc tctaattcgc cttttcaaat   180

ataattcaag gagtcttgag cttgatcttg aatttgtcta tgaacttggt cttggattca   240

atgactaatt tagagcttgt tctagaatca gaattaaatt aattttttta atagatatta   300

aaaatatttt tctctttcta aaataatctt aattttaaaa gtacattgat acttgctctt   360

tttcataatt tgactctcaa aagcactttt gacaaatatt tgtcaaacac aatttgctta   420

tgaaaatcac ttttcaaaca aattagtcaa acacaaattg tttttttttt caaagacagt   480

tttttggaaa gctattttaa aaaagtcctt ttaaaaataa gtaattttta acagcaatgc   540

caaatagact ctcataatct aacaaaggta tgagagtggg ggcttgagga tgtgatggtc   600

aagtagtagg cattgggggc gttaggtggg tagggagtat ataataaata tacaatatta   660

tttatagaac ttatttttcc aaccttttat taaataagtc atttttctta ttttttaata   720

acttattttt caaaagaata attatttttc tccataccat acgacaaatg cacttaattg   780

tgcatttatt tgagattttt ttcttcgaga ttttcctcta aagttttagc tgaactagaa   840

cacacgccat taggttcctt gttagtttca atccaacaca caccttagcc caacactatt   900

tattttatca actcatactt attcccaaca cataactagg gaaagcgtat gattaaacac   960

atattcgatt tggatgctgc tatttaattt gtattcattt ttttaatata tttttcacac  1020

ggttactcat ttcaaataat tttaggtata tggtatttga aattagttgt gacaaatcta  1080

acttcaaatg caatatttaa attttatatg attgaagttt ggttattttt atcaaactca  1140

agttattcta tccaaagttc atacacgtat aactaacata aaagcaatac aaaaataatt  1200

aaactatttt tttaatatta attataaata tatatttatt aattaatata ttgtcaaact  1260

aatatgtgat agtttaggtt tgaaacttac actctcaata gtttaggtat gaaactcaaa  1320

aaaaggggat agtttaggtg tgtttttgac acttatctct attttaattg atgtttttta  1380

ctcaatacaa agtgtaaaaa acaatttttt gttttttttg taatttgttg tttaaaataa  1440

ttatagataa ttttatggtt ataaattatt tcattaaaca gttagcatct atgctctcta  1500

aatttgagca tgtactagta gacacttaaa cttgtttaaa caatagacac atatctacct  1560

agcataatac acgtgtgatg caacaacgta ggcacaaatt gcacgttggc tggatggcgt  1620

gctgggatgg cgtgcctact ataagtattg aattttacca tagcttccca tctacatcaa  1680

actcaaagga aag                                                      1693


<210> SEQ ID NO 35
```

<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 35
tcagcaatag tgcattacca gag 23

<210> SEQ ID NO 36
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 36
cgcctaagtg aagaaggggt a 21

<210> SEQ ID NO 37
<211> LENGTH: 1693
<212> TYPE: DNA
<213> ORGANISM: S.chacoense
<220> FEATURE:
<223> OTHER INFORMATION: 23ACT promoter

<400> SEQUENCE: 37
tcagcaatag tgcattacca gagtaagacg tgactcaatt tgagaatagc aaagagctcc 60
tcctgttcgc ttctccaatt acaataatca agaatggaga aatatagcaa caatcgtttt 120
gttgatttta aagtgcgagt gttacaatct ctattattcc tctaattcgc cttttcaaat 180
ataattcaag gagtcttgag cttgatcttg aatttgtcta tgaacttggt cttggattca 240
atgactaatt tagagcttgt tctagaatca gaattaaatt aattttttta atagatatta 300
aaaatatttt tctctttcta aaataatctt aattttaaaa gtacattgat acttgctctt 360
tttcataatt tgactctcaa aagcactttt gacaaatatt tgtcaaacac aatttgctta 420
tgaaaatcac ttttcaaaca aattagtcaa acacaaattg tttttttttt caaagacagt 480
tttttggaaa gctattttaa aaaagtcctt ttaaaaataa gtaattttta acagcaatgc 540
caaatagact ctcataatct aacaaaggta tgagagtggg ggcttgagga tgtgatggtc 600
aagtagtagg cattgggggc gttaggtggg tagggagtat ataataaata tacaatatta 660
tttatagaac ttatttttcc aaccttttat taaataagtc atttttctta ttttttaata 720
acttattttt caaaagaata attatttttc tccataccat acgacaaatg cacttaattg 780
tgcatttatt tgagattttt ttcttcgaga ttttcctcta aagttttagc tgaactagaa 840
cacacgccat taggttcctt gttagtttca atccaacaca caccttagcc caacactatt 900
tattttatca actcatactt attcccaaca cataactagg gaaagcgtat gattaaacac 960
atattcgatt tggatgctgc tatttaattt gtattcattt ttttaatata tttttcacac 1020
ggttactcat ttcaaataat tttaggtata tggtatttga aattagttgt gacaaatcta 1080
acttcaaatg caatatttaa attttatatg attgaagttt ggttattttt atcaaactca 1140
agttattcta tccaaagttc atacacgtat aactaacata aaagcaatac aaaaataatt 1200
aaactatttt tttaatatta attataaata tatatttatt aattaatata ttgtcaaact 1260
aatatgtgat agtttaggtt tgaaacttac actctcaata gtttaggtat gaaactcaaa 1320
aaaaggggat agtttaggtg tgtttttgac acttatctct attttaattg atgtttttta 1380
ctcaatacaa agtgtaaaaa acaatttttt gttttttttg taatttgttg tttaaaataa 1440
ttatagataa ttttatggtt ataaattatt tcattaaaca gttagcatct atgctctcta 1500
aatttgagca tgtactagta gacacttaaa cttgtttaaa caatagacac atatctacct 1560
agcataatac acgtgtgatg caacaacgta ggcacaaatt gcacgttggc tggatggcgt 1620
gctgggatgg cgtgcctact ataagtattg aattttacca tagcttccca tctacatcaa 1680
actcaaagga aag 1693

<210> SEQ ID NO 38
<211> LENGTH: 1689
<212> TYPE: DNA
<213> ORGANISM: S.tuberosum
<220> FEATURE:
<223> OTHER INFORMATION: 23ACT promoter A

<400> SEQUENCE: 38
tcagcaatag tgcattacca gagtaagacg tgactcaatt tgagaatagc aaagagctcc 60
tcctgttcgc ttctccaatt acaataatca agaatggaga aatatagcaa caagcgtttt 120
gttgatttta aagtgcgagt gttacaatct ctattattcc tctaattcgc cttttcaaat 180
ataattcaag gagtcttgag cttgatcttg aatttgtcta tgaacttggt cttggattca 240
atgactaatt tagagcttgt tctagaatca gaattaaatt aattttttta atagatatta 300
aaaatatttt tctctttcta aaataatctt aattttaaaa gtacattgat gcttgctctt 360
tttcataatt tgactctcaa aagcactttt gacaaatatt tgtcaaacac aatttgctta 420
tgaaaatcat ttttcaaaca aattagtcaa acacaaattg tttttttttt caaagacagt 480
tttttggaaa gctattttaa aaaagtcctt ttaaaaataa gtaattttta acagcaatgc 540
caaatagact ctcataatct aacaaaggta tgagagtggg ggcttgagga tgtgatggtc 600
aagtagtagg cattgggggc gttaggtggg tagggagtat ataataaata tacaatatta 660
tttatagaac ttatttttcc aaccttttat taaataagtc atttttctta ttttttaata 720
acttattttt caaaagaata attatttttc tccataccat acgacaaatg cacttaattg 780
tgcatttatt tgagattttt ttcttcgaga ttttcctctg aagttttagc tgaactagaa 840
cacacgccat taggttcctt gttagtttca atccaacaca caccttagcc caacactatt 900
tattttatca actcatactt attcccaaca cataactagg gaaagcgtat gattaaacac 960
atattcgatt tggatgctgc tatttaattt gtattcattt ttttaatata tttttcacat 1020
ggttactcat ttcaaataat tttaggtata tggtatttga aattagttgt gacaaatcta 1080
acttcaaatg caatatttaa attttatatg attgaagttt ggttattttt atcaaactca 1140
agttattcta tccaaagttc atacacgtat aactaacata aaagcaatac aaaaataatt 1200
aaactatttt tttaatatta attataaata tatatttatt aattaatata ttgtcaaact 1260
aatatgtgat agtttaggtt tgaaacttac actctcaata gtttaggtat gaaactcaaa 1320
aaaaggggat agtttaggtg tgtgacactt atctctattt taattgatgt tttttactcg 1380
atacaaagtg taaaaaaacaa ttttttgttt tttttgtaat ttgttgttta aaataattat 1440
agataatttt atggttataa attatttcat taaacagtta gcatctatgc tctctaaatt 1500
tgagcatgta ctagtagaca cttaaacttg tttaaacaat agacacatat ctacctagca 1560
taatacacgt gtgatgcaac aacgtaggca caaattgcac gttggctgga tggcgtgctg 1620
ggatggcgtg cctactataa gtattgaatt ttaccatagc ttcccatcta catcaaactt 1680
aaaggaaag 1689

<210> SEQ ID NO 39
<211> LENGTH: 1676
<212> TYPE: DNA
<213> ORGANISM: S.tuberosum
<220> FEATURE:
<223> OTHER INFORMATION: 23ACT promoter B

<400> SEQUENCE: 39
tcagcaatag tgcattacca gagtaagacg tgactcaatt tgagaatagc aaagagctcc 60
tcctgttcgc ttctccaatt acaataatca agaatggaga aatatagcaa caatcgtttt 120
gtagatttta aagtgcgagt gttacagtct ctattattcc tctgattcgt cttttcaaat 180
ataattcaag gagtcttgag cttgatcttg aatttgtcta tgaacttggt cttggattca 240
atgactaatt tagagcttgt tctagaatca gaattaaatt aattttttta atagatatta 300
agaatatttt tctctttcta aaataatctt aattttaaaa gtacattgat acttgctctt 360
tttcataatt tgactctcaa aagcactttt gacaaatatt tgtcaaacac aatttgctta 420
tgaaaatcac ttttcaaaca aattagtcaa acacaaattg ttttttttc aaagacagtt 480 ttttggaaag ctattttaaa aaagtccttt taaaaataag taatttttaa cagcaatgcc 540
aaatagactc tcataatcta acaaaggtat gagagtgggg gcttgaggat gtgatggtca 600
agtagtaggc attgggggcg ttaggtgggt agggagtata caataaatat acaatattat 660
ttatagaact tatttttcca accttttatt aaataagtca tttttcttat tttttaataa 720
cctatttttc aaaaaaataa ttatttttct ccataccata cgacaaatgc acttaattgt 780
gcatttattt gagatttttt tcttcgagat tttcctctga agttttagct gaactagaac 840
acacgccatt aggttccttg ttagtttcaa tccaacacac accttagccc aacactattt 900
attttatcaa ctcatactta ttcccaacac aaaactaggg aaagcgtatg attaaacaca 960
tattcgattt ggatgctgct atttaatttg tattcatttt tttaatacat ttttcacacg 1020
gttactcatt tcaaataatt ttaggtatat ggtatttgaa attagtttga caaaatctaa 1080
cttcaaatgc aatatttaaa ttttatatga ttgaagtttg gttattttta tcaaactcaa 1140
gttattctat ccaaagttca tacacgtata actaacataa aagcaataca aaaataatta 1200
aactattttt ttaatattaa ttataaatat atatttatta attaatatat tgtcaaacta 1260
atatgtgata gtttaggttt gaaacttaca ctctcaatag tttaggtatg aaactcaaaa 1320
aaagaggata gtttaggtgt gtttttgaca cttatctcta ttttaattga tgttttttac 1380
tcgatacaaa gtgtaaaaaa caatttattt tttttgtaat ttgttgttta aaataattat 1440
agataatttt atggttataa attatttcat taaacagtta gcatctatgc tctctaaatt 1500
tgagcatgta ctagtagaca cttaaacttg tttaaacaat agacacatat ctacctagca 1560
taatacacat gtgatgcaac aacgtaggca caaattgcac gttggctgga tggcgtgcct 1620
actataagta ttgaatttta ccatagcttc ccatctacat caaacttaaa ggaaag 1676

<210> SEQ ID NO 40
<211> LENGTH: 1676
<212> TYPE: DNA
<213> ORGANISM: S.tuberosum
<220> FEATURE:
<223> OTHER INFORMATION: 23ACT promoter

<400> SEQUENCE: 40
tcagcaatag tgcattacca gagtaagacg tgactcaatt tgagaatagc aaagagctcc 60
tcctgttcgc ttctccaatt acaataatca agaatggaga aatatagcaa caatcgtttt 120

```
gtagatttta aagtgcgagt gttacagtct ctattattcc tctgattcgt cttttcaaat    180
ataattcaag gagtcttgag cttgatcttg aatttgtcta tgaacttggt cttggattca    240
atgactaatt tagagcttgt tctagaatca gaattaaatt aattttttta atagatatta    300
agaatatttt tctctttcta aaataatctt aattttaaaa gtacattgat acttgctctt    360
tttcataatt tgactctcaa aagcactttt gacaaatatt tgtcaaacac aatttgctta    420
tgaaaatcac ttttcaaaca aattagtcaa acacaaattg tttttttttc aaagacagtt    480
ttttggaaag ctattttaaa aaagtccttt taaaaataag taatttttaa cagcaatgcc    540
aaatagactc tcataatcta acaaaggtat gagagtgggg gcttgaggat gtgatggtca    600
agtagtaggc attgggggcg ttaggtgggt agggagtata caataaatat acaatattat    660
ttatagaact tatttttcca acctttttatt aaataagtca tttttcttat tttttaataa    720
cctatttttc aaaaaaataa ttatttttct ccataccata cgacaaatgc acttaattgt    780
gcatttattt gagatttttt tcttcgagat tttcctctga agttttagct gaactagaac    840
acacgccatt aggttccttg ttagtttcaa tccaacacac accttagccc aacactattt    900
attttatcaa ctcatactta ttcccaacac aaaactaggg aaagcgtatg attaaacaca    960
tattcgattt ggatgctgct atttaatttg tattcatttt tttaatacat ttttcacacg   1020
gttactcatt tcaaataatt ttaggtatat ggtatttgaa attagtttga caaaatctaa   1080
cttcaaatgc aatatttaaa ttttatatga ttgaagtttg gttattttta tcaaactcaa   1140
gttattctat ccaaagttca tacacgtata actaacataa aagcaataca aaaataatta   1200
aactattttt ttaatattaa ttataaatat atatttatta attaatatat tgtcaaacta   1260
atatgtgata gtttaggttt gaaacttaca ctctcaatag tttaggtatg aaactcaaaa   1320
aaagaggata gtttaggtgt gtttttgaca cttatctcta ttttaattga tgtttttttac   1380
tcgatacaaa gtgtaaaaaa caatttattt tttttgtaat ttgttgttta aaataattat   1440
agataatttt atggttataa attatttcat taaacagtta gcatctatgc tctctaaatt   1500
tgagcatgta ctagtagaca cttaaacttg tttaaacaat agacacatat ctacctagca   1560
taatacacat gtgatgcaac aacgtaggca caaattgcac gttggctgga tggcgtgcct   1620
actataagta ttgaatttta ccatagcttc ccatctacat caaacttaaa ggaaag        1676
```

<210> SEQ ID NO 41
<211> LENGTH: 1445
<212> TYPE: DNA
<213> ORGANISM: Solanum chacoense
<220> FEATURE:
<223> OTHER INFORMATION: 23DOX promoter

<400> SEQUENCE: 41

```
gggtccgact ttttgttttt aagaaattgc acattcgaag gatatttttg tccaaagtgg     60
aaatattgtg taaaaaatgt gtatttattg tgattttgaa tgttttgtag ggtaatagga    120
cgcacgcaaa gttaaggtgt ctttttgaaa atcttggaca acttcaagta tcacttaatg    180
ttttttctca aaatctaatt tactttcgta aactatgtgt cagatcaaaa tttaacaaat    240
tcaaaaggaa tgagtaataa atagctctta caaatcacca tttttcgtct tcttcacact    300
caaaattttt ctcaatgaaa aaatgtgatt gattataatt agctcttaca catacttttg    360
ggttctattt atttagattt gataaaaaga tatatcaaga aaacttcaaa tagaaaaaca    420
atataataag taaattcaag caatagatct tgaaaaatta aattttaaaa aaggtgaatg    480
```

```
agatattttt ttaacaaaag ctttttatta tgattatgat gatgtagtca aagcagaaga    540

aaagaaaagg gggtgggtgg ggggtctggg gctgaaaaga agaggaaaaa ggtggggctg    600

ggggctgggc taaagtaagg ctggcaatgg aaccgggagg taccggtatc ggttccgtac    660

ctcccggttc cgatccgtta ccggctccat ctcggttccg gatagtaccg gttcgatccg    720

gtattgtgtc ggtctgggag gggtaacggg acggaaactg ggatttaccg gtctgtcccg    780

gtccggttag tcccggttcc agtccggttc gttcagtttt ttttttttaa tcttaaattt    840

taaattatag ccgttgagag ccattgagca acgggttttg ggcgccacca acggctcttt    900

cacccccata actccccttt ataattaata ataaggataa atttactaat taaatgtaaa    960

attattcatt aatttcataa aattgacaag tattattgaa catctcaaaa taatatagtg   1020

aacaactact ccatcagtcc ctatttgtcc aattatccct tttcacttgt ggattaaatc   1080

aaaaaagaat aaatttttcc ctgttatgct atcgattaat taatttgaaa aagatagaac   1140

ttcttaaaaa tttaaatttt ttattttctc tattttataa ttaataggga taaattatta   1200

aatccactat gtcaaatact gtatttttaa taaatatgtt aatttaaaag caaatggaat   1260

atatagacca catatttcct catttttaaa gtaaaaatct tgatatttgt tcacatgatg   1320

aaatagttca cacccatttc ccattatata tagaccacca atttcctcat ttttaaagta   1380

aaaacttaaa aagtgtttct tctttctttt ttctctttgc tcatattcta aaaagtattt   1440

catca                                                                1445
```

<210> SEQ ID NO 42
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 42

```
gggtccgact ttttgttttt                                                  20
```

<210> SEQ ID NO 43
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 43

```
caatggcaat tgtggaatca                                                  20
```

<210> SEQ ID NO 44
<211> LENGTH: 1592
<212> TYPE: DNA
<213> ORGANISM: S.chacoense
<220> FEATURE:
<223> OTHER INFORMATION: 23DOX promoter A

<400> SEQUENCE: 44

```
gggtccgact ttttgttttt aagaaattgc acattcgaag gatatttttg tccaaagtgg     60

aaatattgtg taaaaaatgt gtatttattg tgattttgaa tgttttgtag ggtaatagga    120

cgcacgcaaa gttaaggtgt ctttttgaaa atttgggaca acttcaagta tcacttaatg    180

tttttttctc aaaatctaat ttacttttgt aaactatgag tcagatcaaa atttaacaaa    240

ttcaaaagga atgagtaata aatagctctt acaaatcacc atttttcatc ttcttcacac    300

tcaaaatttt tctcaatgaa aaaatgtgat tgattataat tagctcttac acatactttt    360
```

gggttctatt tatttagatt tgataaaaag atatatcaag aaaacttcaa atagaaaaac 420
aatataataa gtaaattcaa gcaatagatc ttgaaaaatt aaattttaaa aaaggtgaat 480
gagatatttt tttaacaaaa gctttttatt atgattatga tgatgtagtc aaagcagaag 540
aaaagaaaag ggggtgggtg ggggtctggg gctgaaaaga agaggaaaaa ggtggggctg 600
ggggctgggc taaagtaagg ctggcaacgg aaccgggagg taccggtatc agttccgatc 660
cgttaccggc ttcatctcgg ttccggatag taccggttcg atccggtatt gtgtcggtct 720
gggaggggta acgggacgga aactgggatt taccggtttg tcccggtccg gttagtcccg 780
gttccagtcc ggttcgttca gttttttttt taatcttaaa ttttaaatta tagccgttga 840
gagccattga gcaacgggtt ttgggcgcca ccaacggctc tttcaccccc ataactcccc 900
tttataatta ataataagga taaatttact aattaaatgt aaaattattc attaatttca 960
taaaattgac aagtattatt gaacatctca aaataatata gtgaacaact actccatcag 1020
tccctatttg tccaattttc ccttttcact tgtggattaa atcaaaaaag aataaatttg 1080
tccctgttat gctatcgatt aattaatttg aaaaagatag aacttcttaa aaatttaaat 1140
tttttatttt ctctatttta taattaatag ggataaatta ttaaatccac tatgtcaaat 1200
actgtatttt aaataaatat gttaatttaa aagcaaatgg aatattgttg aagggaagga 1260
gtaaaaatct tgatatttgt tcacatgatg aaatagttca cacccatttc ccattatata 1320
tagaccacat atttcctcat ttttaaagta aaaatcttga tatttgttca catgatgaaa 1380
tagtacgttc acacccattt cccatgatat atagaccaca tatttcctca tttttaaagt 1440
aaaaatcttg atatttgttc acatgatgaa atagttcaca cccatttccc attatatata 1500
gaccacctat ttcctcattt ttaaagtaaa aacttaaaag tgtttcttct ttcttttttc 1560
tctttgctca tattctaaaa agtatttcat ca 1592

<210> SEQ ID NO 45
<211> LENGTH: 1593
<212> TYPE: DNA
<213> ORGANISM: S.chacoense
<220> FEATURE:
<223> OTHER INFORMATION: 23DOX promoter B

<400> SEQUENCE: 45
gggtccgact ttttgttttt aagaaattgc acattcgaag gatatttttg tccaaagtgg 60
aaatattgtg taaaaaatgt gtatttattg tgattttgaa tgttttgtag ggtaatagga 120
cgcacgcaaa gttaaggtgt ctttttgaaa atctgggaca acttcaagta tcacttaatg 180 tttttctca aaatctaatt tactttcgta aactatgtgt cagatcaaaa tttaacaaat 240
tcaaaaggaa tgagtaataa atagctctta caaatcacca tttttcgact tcttcacact 300
caaatttttt ctcaatgaaa aaatgtgatt gattataatt agctcttaca catacttttg 360
ggttctattt atttagattt gataaaaaga tatatcaaga aaacttcaaa tagaaaaaca 420
atataataag taaattcaag caatagatct tgaaaaatta aattttaaaa aaggtgaatg 480
agatattttt ttaacaaaag ctttttatta tgattatgat gatgtagtca aagcagaaga 540
aaagaaaagg gggtgggtgg ggggtctgga gctgaaaaga agaggaaaaa ggtggggctg 600
ggggctgggc taaagtaagg ctggcaacgg aatcgggagg taccggtatc ggttccgatc 660
cgttaccggc tccatctcgg ttccggatag taccggttcg atccggtatt gtgtcggtct 720
gggaggggta acgggacgga aactgggatt taccggtttg tcccggtccg gttagtcccg 780

-continued

```
gttccagtcc ggttcgttca gttttttttt ttaatcttaa attttaaatt atagccgttg    840

agagccattg agcaacgggt tttgggcgcc accaacggct ctttcacccc cataactccc    900

ctttataatt aataataagg ataaatttac taattaaatg taaaattatt cattaatttc    960

ataaaattga caagtattat tgaacatctc aaaataatat agtgaacaac tactccatca   1020

gtccctattt gtccaatttt cccttttcac ttgtggatta aatcaaaaaa gaataaattt   1080

ttccctgtta tgctatcgat taattaattt gaaaaagata gaacttctta aaaatttaaa   1140

tttttatttt tctctatttt ataattaata gggataaatt attaaatcca ctatgtcaaa   1200

tactgtattt ttaataaata tgttaattta aaagcaaatg gaatattgtt gaagggaagg   1260

agtaaaaatc ttgatatttg ttcacatgat gaaatagttc acacccattt cccattatat   1320

atagaccaca tatttcctca tttttaaagt aaaaatcttg atatttgttc acatgatgag   1380

atagtacgtt cacacccatt tcccatgata tatagaccac atatttcctc atttttaaag   1440

taaaaatctt gatatttgtt cacatgatga aatagttcac acccatttcc cattatatat   1500

agaccaccta tttcctcatt tttaaagtaa aaacttaaaa gtgtttcttc tttctttttt   1560

ctctttgctc atattctaaa aagtatttca tca                                1593


<210> SEQ ID NO 46
<211> LENGTH: 32
<212> TYPE: DNA
<213> ORGANISM: Artificial Sequence
<220> FEATURE:
<223> OTHER INFORMATION: Artificially synthesized primer sequence

<400> SEQUENCE: 46

taaaattatt cattaatttc ataaaattga ca                                   32


<210> SEQ ID NO 47
<211> LENGTH: 955
<212> TYPE: DNA
<213> ORGANISM: S.tuberosum
<220> FEATURE:
<223> OTHER INFORMATION: 23DOX promoter A

<400> SEQUENCE: 47

taaaattatt cattaatttc ataaaattga caaatattgt tgaacatctc aaaataatat     60

agtggacaac tactccatcc atccctattt gtccaatttt tcctttttat ttgtctattt    120

tcacaaatca agaaagaata attttttccg tattatgcca ttgattaatt aatttgaaaa    180

agatagaact tcttgaaaat tttaaatttt tatttctcta ctttataatt aataggaata    240

aattattaaa cccactatgt caaatattat atttttaata aatatgttaa tttaaaagca    300

gtaattagaa ccgagggaat attgttgaag ggatggagta aaaatcttga tatttgtgtt    360

agggttttgc cctggttttc ttaccataat ttgagattta ttttttctta aagaaaagac    420

aaaacactac cataaatgtt tttacttttt ctgaaagaaa aatataatat tctttcatat    480

ttggtttatt ctttcctttt aggaaaatgt ttatggagta gctagttctt ttctagtagg    540

aaaggtttta ggactctata aatataggtt tgtttcttct aacacaataa taacaataac    600

atccacaatg tagtttttta agaatttagt ttatgaggag attttctcct aaacatattt    660

atgcttttta atagtagttt tcaatatgta ggtcgtttga ccaaaccata ttaataatat    720

atctttagta tgtttttatt tatcgtctgt tttgtcaacc atatgatttg caattgtacg    780

cttccgcatg acgccctatt caccttcatg acccaacaat ttgttcacat gatgaaataa    840

ttcacccatt tcccattata tatagaccac ctatttcctc atttttaagt aaaaactttg    900
```

aagtgtttct tctttctttt ttctctttgt tcatattcta aaaaatattt catca 955

<210> SEQ ID NO 48
<211> LENGTH: 955
<212> TYPE: DNA
<213> ORGANISM: S.tuberosum
<220> FEATURE:
<223> OTHER INFORMATION: 23DOX promoter B

<400> SEQUENCE: 48
taaaattatt cattaatttc ataaaattga caaatattgt tgaacatctc aaaatagtat 60
agtggacaac tactccatcc atccctattt gtccaatttt tcctttttat ttgtctattt 120
tcacaaatca agaaagaata attttttccg tattatgcca ttgattaatt aatttgaaaa 180
agatagaact tcttgaaaat tttaaatttt tatttctcta ctttataatt aataggaata 240
aattattaaa cccactatgt caaatattat atttttaata aatatgttaa tttaaaagca 300
gtaattagaa ccgagggaat actgttgaag ggatggagta aaaatcttga tatttgtgtt 360
agggttttgc cctggttttc ttaccataat ttaagattta tttttcttta aagaaaagac 420
aaaacactac cataaatgtt tttacttttc ctgaaagaaa aatataatat tctttcatat 480
ttggtttatt ctttcctttt aggaaaatgt ttatggagta gctagttctt ttctagtagg 540
aaaggtttta ggactctata aatataggtt tgtttcttct aacacaataa taacaataac 600
atccacaatg tagtttttta agaatttagt ttatggggag attttctcct aaacatattt 660
atgcttttta atagtagttt tcaatatgta ggtcgtttga ccaaaccata ttaataatat 720
atctttagtg tgtttttatt tatcgtctga tttgtcaacc atatgatttg caattgtacg 780
ctttcgcatg acgccctatt caccttcata acccaacaat ttgttcacat gatgaaatag 840
ttcacccatt tcccattata tatagaccac ctatttcctc atttttaagt aaaaactttg 900
aagtgtttct tctttctttt ttctctttgt tcatattcta aaaaatattt catca 955

<210> SEQ ID NO 49
<211> LENGTH: 955
<212> TYPE: DNA
<213> ORGANISM: S.tuberosum
<220> FEATURE:
<223> OTHER INFORMATION: 23DOX promoter A

<400> SEQUENCE: 49
taaaattatt cattaatttc ataaaattga caaatattgt tgaacatctc aaaataatat 60
agtggacaac tactccatcc atccctattt gtccaatttt tcctttttat ttgtctattt 120
tcacaaatca agaaagaata attttttccg tattatgcca ttgattaatt aatttgaaaa 180
agatagaact tcttgaaaat tttaaatttt tatttctcta ctttataatt aataggaata 240
aattattaaa cccactatgt caaatattat atttttaata aatatgttaa tttaaaagca 300
gtaattagaa ccgagggaat attgttgaag ggatggagta aaaatcttga tatttgtgtt 360
agggttttgc cctggttttc ttaccataat ttgagattta tttttcttta aagaaaagac 420
aaaacactac cataaatgtt tttacttttt ctgaaagaaa aatataatat tctttcatat 480
ttggtttatt ctttcctttt aggaaaatgt ttatggagta gctagttctt ttctagtagg 540
aaaggtttta ggactctata aatataggtt tgtttcttct aacacaataa taacaataac 600
atccacaatg tagtttttta agaatttagt ttatgaggag attttctcct aaacatattt 660
atgcttttta atagtagttt tcaatatgta ggtcgtttga ccaaaccata ttaataatat 720

-continued

```
atctttagta tgtttttatt tatcgtctgt tttgtcaacc atatgatttg caattgtacg    780

cttccgcatg acgccctatt caccttcatg acccaacaat ttgttcacat gatgaaataa    840

ttcacccatt tcccattata tatagaccac ctatttcctc atttttaagt aaaaactttg    900

aagtgtttct tctttctttt ttctctttgt tcatattcta aaaaatattt catca         955
```